(12) United States Patent
Simunovic et al.

(10) Patent No.: US 9,615,593 B2
(45) Date of Patent: Apr. 11, 2017

(54) METHODS AND APPARATUSES FOR THERMAL TREATMENT OF FOODS AND OTHER BIOMATERIALS, AND PRODUCTS OBTAINED THEREBY

(71) Applicants: North Carolina State University, Raleigh, NC (US); Industrial Microwave Systems, L.L.C., Morrisville, NC (US); The United States of America, as Represented by the Secretary of Agriculture, Washington, D.C., Washington, DC (US)

(72) Inventors: Josip Simunovic, Raleigh, NC (US); Kenneth R. Swartzel, Raleigh, NC (US); Van-Den Truong, Raleigh, NC (US); Gary Dean Cartwright, Apex, NC (US); Kandiyan Puthalath Sandeep, Cary, NC (US); David L. Parrott, Raleigh, NC (US); Pablo Coronel, Cary, NC (US)

(73) Assignees: North Carolina State University, Raleigh, NC (US); Industrial Microwave Systems, L.L.C., Morrisville, NC (US); The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/832,650

(22) Filed: Aug. 21, 2015

(65) Prior Publication Data

US 2016/0165909 A1    Jun. 16, 2016

Related U.S. Application Data

(63) Continuation of application No. 11/274,044, filed on Nov. 14, 2005, now abandoned.

(Continued)

(51) Int. Cl.
*A23B 7/01*   (2006.01)
*A23L 3/005*  (2006.01)
(Continued)

(52) U.S. Cl.
CPC .............. *A23B 7/01* (2013.01); *A23L 3/001* (2013.01); *A23L 3/005* (2013.01); *A23L 3/01* (2013.01);
(Continued)

(58) Field of Classification Search
CPC ... A23B 7/01; A23L 3/005; A23L 3/01; A23L 3/002; A23L 3/22; A23L 3/225; A61L 2/10
See application file for complete search history.

(56) References Cited

U.S. PATENT DOCUMENTS 3,830,945 A    8/1974   Scharfman
3,889,009 A    6/1975   Lipoma
(Continued)

FOREIGN PATENT DOCUMENTS

AU    20055304583    5/2012
CA    2558260        9/2009
(Continued)

OTHER PUBLICATIONS

Notice of Intent to Grant corresponding to European Patent Application No. 05 826 078.7 dated Feb. 23, 2016.
(Continued)

*Primary Examiner* — Erik Kashnikow
*Assistant Examiner* — Chaim Smith
(74) *Attorney, Agent, or Firm* — Jenkins, Wilson, Taylor & Hunt, P.A.

(57) ABSTRACT

Methods and apparatuses for thermally treating flowable materials using electromagnetic radiation, and foods and materials obtained thereby. Also provided are methods of continuous flow thermal treatment of biomaterials, apparatuses for performing the same, and products prepared using the methods and/or apparatuses.

26 Claims, 42 Drawing Sheets

Related U.S. Application Data

(60) Provisional application No. 60/627,499, filed on Nov. 12, 2004, provisional application No. 60/664,762, filed on Mar. 24, 2005.

(51) Int. Cl.
    *A23L 3/01*     (2006.01)
    *A23L 3/22*     (2006.01)
    *A61L 2/10*     (2006.01)
    *A23L 3/00*     (2006.01)

(52) U.S. Cl.
    CPC ............... *A23L 3/22* (2013.01); *A23L 3/225* (2013.01); *A61L 2/10* (2013.01); *A23V 2002/00* (2013.01)

(56) References Cited

U.S. PATENT DOCUMENTS

| | | | |
|---|---|---|---|
| 4,015,341 A | 4/1977 | McKinney et al. | |
| 4,091,119 A | 5/1978 | Bach | |
| 4,170,073 A | 10/1979 | Ignatowicz | |
| 4,430,806 A | 2/1984 | Hopkins et al. | |
| 4,640,020 A | 2/1987 | Wear et al. | |
| 4,808,425 A | 2/1989 | Swartzel et al. | |
| 4,808,783 A | 2/1989 | Stenstrom | |
| 4,975,246 A | 12/1990 | Charm | |
| 5,039,947 A | 8/1991 | Kraszewski et al. | |
| 5,135,122 A | 8/1992 | Gross et al. | |
| 5,205,050 A | 4/1993 | Masaaki et al. | |
| 5,230,160 A | 7/1993 | Gross et al. | |
| 5,290,583 A | 3/1994 | Reznik et al. | |
| 5,672,316 A | 9/1997 | Knapp | |
| 5,697,291 A | 12/1997 | Burgener et al. | |
| 5,852,882 A | 12/1998 | Kendal et al. | |
| 5,863,580 A | 1/1999 | Reznik | |
| 5,934,997 A | 8/1999 | Nelson et al. | |
| 5,962,054 A | 10/1999 | Kozempel et al. | |
| 5,976,592 A | 11/1999 | Polato | |
| 5,998,774 A | 12/1999 | Joines | |
| 6,087,642 A | 7/2000 | Joines | |
| 6,121,594 A | 9/2000 | Joines | |
| 6,231,908 B1 | 5/2001 | Lelieveld et al. | |
| 6,248,986 B1 | 6/2001 | Tran et al. | |
| 6,265,702 B1 | 7/2001 | Drozd | |
| 6,346,693 B1 | 2/2002 | Kasevich | |
| 6,406,727 B1 | 6/2002 | Hamid-Samimi et al. | |
| 6,546,646 B1 | 4/2003 | Thomas | |
| 6,583,395 B2 | 6/2003 | Furtlehner | |
| 6,624,396 B2 | 9/2003 | Witt et al. | |
| 6,797,929 B2 | 9/2004 | Drozd | |
| 8,742,305 B2 | 6/2014 | Simunovic et al. | |
| 2001/0035407 A1 | 11/2001 | Drozd et al. | |
| 2003/0205576 A1 | 11/2003 | Drozd et al. | |
| 2004/0081730 A1 | 4/2004 | Drozd et al. | |
| 2004/0191382 A1 | 9/2004 | Cooper et al. | |
| 2006/0151533 A1 | 7/2006 | Simunovic et al. | |
| 2011/0036246 A1 | 2/2011 | Simunovic et al. | |

FOREIGN PATENT DOCUMENTS

| | | |
|---|---|---|
| CA | 2583856 | 8/2013 |
| CA | 2 812 925 | 7/2015 |
| CN | 628761 | 6/2010 |
| EP | 1809565 B1 | 8/2016 |
| GB | 1 222 208 | 2/1971 |
| JP | A S58-058050 | 3/1983 |
| JP | A H07-184613 | 7/1995 |
| JP | H09-150045 | 6/1997 |
| MX | 308179 | 3/2013 |
| NZ | 553749 | 12/2011 |
| WO | WO 95/10943 | 4/1995 |
| WO | WO0036879 | 6/2000 |
| WO | WO0143508 | 6/2001 |
| WO | WO0184889 | 11/2001 |
| WO | WO 02/08678 A1 | 1/2002 |

OTHER PUBLICATIONS

Office Action corresponding to European Patent Application No. 05 826 078.7 dated Sep. 28, 2015.
Office action corresponding to the Canadian Patent Applicaton No. 2,890,728 dated May 6, 2016.
Decision to grant a European patent pursuant to Article 97(1) EPC for European Patent Application No. 05826078.7 dated Jul. 7, 2016.
Bogracheva et al., "The Granular Structure of C-Type Pea Starch and Its Role in Gelatinization," Biopolymers, vol. 45, pp. 323-332 (1998).
Brody, A.L., "Aseptic vs Hot-Fill Packaging for Polyester Bottles," FoodTechnology, vol. 55, No. 11, pp. 76-78 (Nov. 2001).
Campanella & Pelegi, "Determination of the Yield Stress of Semi-Liquid Foods from Squeezing Flow Data," J. Food Sci., vol. 52, p. 215 (1987).
Charm, "The Direct Determination of Shear Stress-Shear Rate Behavior of Foods in the Presence of a Yield Stress," J. Food Sci., vol. 28, pp. 107-113 (1962).
CIE (1976). Colorimetry: official recommendations of the International Commission on Illumination Paris: Commission Internationale de l'Éclairage [International Commission on Illumination], CIE No. 15 (E-1.3.1).
Coronel et al., "Aseptic Processing of Sweetpotato Purees Using a Continuous Flow Microwave System," Journal of Food Science, vol. 68, pp. 1976-1981 (2003).
Coronel et al., "Aseptic Processing of Sweetpotato Purees Using a Continuous Flow Microwave System," Journal of Food Science, vol. 70, No. 9, pp. E1-E6 (2005).
Coronel et al., "Dielectric properties of pumpable food materials at 915 MHz," International Journal of Food Properties, vol. 11, pp. 508-518 (2008).
De Kee et al., "Research Note New Method for the Determination of Yield Stress," J. Texture Stud., vol. 10, pp. 281-288 (1980).
Decision of Granting Patent Right for Invention corresponding to Chinese Patent Application No. 200580038640.0 dated Feb. 12, 2010.
Definition of fluid, Oxford English Dictionary on line, retrieved on Aug. 26, 2010. Retrieved from the internet <URL: U http://dictionary.oed.com/cgi/entry/50086884?query_type=word &queryword=flu id&fi rst= 1&max_to_show= 1O&sort_ type=alpha&s earch_id=2TA4-nDBVK7-8364&result_place=1 &casejd=2TA4-xlgCpF-8365&p=1 &d=1 &sp=1 &qt=1 &ct=0 &ad=1 &print=1 >.
Developments in Sedimentology, Allen John R.L., Elsevier Scientific Publishing Company, pp. 72 and 73, 1982, no month given.
Difco (1998) Difco Manual, 11th edition. Difco Laboratories, Division of Becton Dickinson and Company, Sparks, Maryland, United States of America.
European Search Report corresponding to European Patent Application Serial No. Mar. 22, 2011.
Examiner's Answer corresponding to U.S. Appl. No. 11/274,044 dated Apr. 10, 2013.

(56) References Cited

OTHER PUBLICATIONS

Fasina et al., "Thermal and Dielectric Properties of Sweetpotato Puree," International Journal of Food Properties, vol. 6, pp. 461-472 (2003).
International Search Report and the Written Opinion of the International Searching Authority, or the Declaration corresponding to PCT Application No. PCT-US05-41479 dated Nov. 27, 2006.
Interrogation Notice corresponding to Japanese Patent Application No. dated Jan. 19, 2013. (Translation).
Interview Summary corresponding to U.S. Appl. No. 12/855,388 dated Jan. 16, 2014.
Interview Summary corresponding to U.S. Appl. No. 11/274,044 dated Dec. 19, 2011.
Kyereme et al., "Modeling the Temperature Effect on the Flow Behavior of Sweet Potato Puree," Journal of Food Process Engineering vol. 22, pp. 235-247 (1999).
Lopez, A. (1987) A complete course in cannning and related processes. Book, III. Processing procedure for canned products. Baltimore, MA. The Canning Trade. p. 96.
Missaire et al,. "Research Note Yield Stress of Structured and Unstructured Food Suspensions," J. Texture Stud., vol. 21, pp. 479-490 (1990).
Nakayama et al., "Pipe Transportation of Minced Fish Paste," J. Food Sci., vol. 45, pp. 844-847 (1980).
New Zealand Examination Report corresponding to New Zealand Patent Application No. 553749 dated May 9, 2011.
Notice of Allowance corresponding to Canadian Patent Application 2,812,925 dated Nov. 7, 2014.
Notice of Allowance corresponding to Canadian Patent Application No. 2,583,856 dated Jan. 1, 2013.
Notice of Allowance corresponding to U.S. Appl. No. 12/855,388 dated Jan. 22, 2014.
Notification Concerning Transmittal of International Preliminary Report on Patentability (Chapter I of the Patent Cooperation Treaty) corresponding to a PCT Application. No. PCT/US2005/041479 dated May 24, 2007.
Office Action corresponding to European Patent Application No. 05 826 078.7 dated May 14, 2012.
Office Action corresponding to Japanese Patent Application No. 2007-541456 dated Sep. 20, 2011.
Office Action corresponding to U.S. Appl. No. 12/855,338 dated Jul. 2, 2013.
Office Communication corresponding to Australian Patent Application No. 2005304583 dated May 5, 2010.
Office Communication corresponding to Canadian Patent Application No. 2,583,856 dated Apr. 20, 2012.
Office Communication corresponding to Canadian Patent Application No. 2,812,925 dated Mar. 18, 2014.
Office Communication corresponding to Chinese Patent Application No. 200580038640.0 dated Apr. 10, 2009. (Translation).
Office Communication corresponding to Japanese Patent Application No. 2007-541456 dated Jul. 27, 2010.
Office Communication corresponding to Korean Patent Application No. 10-2007-7010479 dated Aug. 30, 2012.
Office Communication corresponding to Korean Patent Application No. 10-2007-7010479 dated May 29, 2013.
Office Communication corresponding to Korean Patent Application No. 10-2013-7010479 dated May 27, 2013.
Office Communication corresponding to Mexican Patent Application No. MX/a/2007/003066 dated Oct. 1, 2012.
Office Communication corresponding to New Zealand Patent Application No. 553749 dated Jan. 14, 2011.
Office Communication corresponding to New Zealand Patent Application No. 553749 dated Sep. 10, 2010.
Office Communication corresponding to U.S. Appl. No. 11/274,044 dated Jan. 12, 2010.
Office Communication corresponding to U.S. Appl. No. 11/274,044 dated May 11, 2009.
Office Communication corresponding to U.S. Appl. No. 11/274,044 dated May 23, 2011.
Office Communication corresponding to U.S. Appl. No. 11/274,044 dated May 31, 2012.
Office Communication corresponding to U.S. Appl. No. 11/274,044 dated Sep. 1, 2010.
Office Communication corresponding to U.S. Appl. No. 12/855,388 dated Nov. 5, 2012.
Office Communication pursuant to Rules 70(2) and 70a(2) corresponding to European Patent Application No. 05 826 078.7 dated Apr. 8, 2011.
Official Action corresponding to the U.S. Appl. No. 10/333,584 dated Jan. 11, 2007.
Ofoli et al., "A Generalized Rheological Model for Inelastic Fluid Foods," J. Texture Stud., vol. 18, pp. 213-230 (1987).
Qiu & Rao Role of Pulp Content and Particle Size in Yield Stress of Apple Sauce, J. Food Sci., vol. 53, pp. 1165-1170 (1988).
Sipahioglu & Barringer, "Dielectric Properties of Vegetables and Fruits as a Function of Temperature, Ash, and Moisture Content," Journal of Food Science, vol. 68, pp. 234-239 (2003).
Steffe (1996) Rheological Methods in Food Process Engineering, Second Edition. Freeman Press, East Lansing, Michigan, United States of America.
Summons corresponding to European Patent Application No. 05 826 078.7 dated Feb. 18, 2015.
Swartzel, "Arrhenius Kinetics as Applied to Product Constituent Losses in Ultra High Temperature Processing," Journal of Food Science, vol. 47, pp. 1886-1891 (1982).
Swartzel, "Equivalent-Point Method for Thermal Evaluation of Continuous-Flow Systems," Journal of Agricultural and Food Chemistry, vol. 34, p. 397 (1986).
Tajchakavit et al. "Enhanced destruction of spoilage microorganisms in apple juice during continuous flow microwave heating," Food Research International, vol. 31, No. 10, pp. 713-722 (1998).
Toledo et al., "Relationship Between Composition, Stability and Rheological Properties of Raw Comminuted Meat Batters," J Food Sci., vol. 42, pp. 725-727 (1977).
Truong (1992) In: Hill WA, Bonsi CK and Loretan PA (Eds.). Sweetpotato Technology for the 21st Century. Proceedings of the International Symposium, Jun. 2-6, 1991, Tuskegee, Alabama, pp. 389-399.
Truong et al., "Texturization of Sweetpotato Puree with Alginate: Effects of Tetrasodium Pyrophosphate and Calcium Sulfate," Journal of Food Science, vol. 60, pp. 1054-1059, 1074 (1995).
Turner & Danner, "Circular No. 21—Acceptance of an Improved Frozen Sweet Potato Puree," Alabama Agricultural Experimental Station (1957).
Woolfe (1992) Sweet potato: an untapped food resource. Cambridge University Press, Cambridge, United Kingdom.
Office Action corresponding to Canadian Patent Application No. 2,890,728 dated Dec. 22, 2016.

METHODS AND APPARATUSES FOR THERMAL TREATMENT OF FOODS AND OTHER BIOMATERIALS, AND PRODUCTS OBTAINED THEREBY

CROSS-REFERENCE TO RELATED APPLICATIONS

This application a continuation of U.S. patent application Ser. No. 11/274,044, filed Nov. 14, 2005, herein incorporated by reference in its entirety, which is based on and claims priority to United States Provisional Application Ser. No. 60/627,499, filed Nov. 12, 2004, and U.S. Provisional Application Ser. No. 60/664,762, filed Mar. 24, 2005, the disclosures of each of which are herein incorporated by reference in their entireties.

TECHNICAL FIELD

The presently disclosed subject matter relates to methods and apparatuses for thermally treating flowable materials using electromagnetic radiation, and foods and materials obtained thereby. More particularly, the presently disclosed subject matter relates to methods of continuous flow thermal treatment of biomaterials, apparatuses for performing the same, and products prepared using the methods and/or apparatuses.

BACKGROUND

In order to be sold to the public, food often needs to be treated to minimize microbial growth that can occur between the time that the foodstuffs are harvested and they are purchased by the consumer. There are several general methods that are commercially available for this purpose, the most widespread of which is to heat the material to appropriate temperatures for sufficient lengths of time to kill or otherwise inactivate any microorganisms and/or spores that could germinate and grow at the storage temperature that may be present within the food. For example, milk is typically pasteurized in order to reduce the levels of bacteria that are normally found in the milk, which allows milk to be stored safely longer than it would be otherwise in the absence of the pasteurization process.

Generally, indirect heating methods are used in which the biomaterials are passed through a chamber that is heated to temperatures in excess of 60° C. for some heat sensitive pasteurizations to 100° C. and up to 150° C. to render materials commercially sterile. The presence of the biomaterials within the heated chambers results in the temperature of the biomaterials increasing until they reach substantially the same temperature as the surrounding chamber. However, many foodstuffs and other biomaterials are negatively impacted by the application of heat, either in terms of taste, aesthetic appearance, nutrient levels, or other characteristics so that the ways in which this material can be treated are limited. Additionally, many biomaterials exposed to a heated surface will burn on to the surface causing reduced heat flow, increased run times and can produce off flavors within the product as run time increases and heated material builds up and flakes off into the product.

For example, the utilization of sweet potatoes in the food industry often involves processing of the roots into purees that can be subsequently frozen or canned to allow year-round availability of the produce. The sweet potato puree (SPP) can be used as an ingredient in various products, including baby food, casseroles, puddings, pies, cakes, bread, restructured fries, patties, soups and beverages (Truong, 1992; Truong et al., 1995; Woolfe, 1992).

Preservation of SPP by freezing is a well-established method, but the frozen puree requires considerable investment in frozen distribution and storage as well as a lengthy and poorly controlled defrosting treatment prior to use. Canned puree typically requires excessive thermal treatment, especially when processed in institutional-size packages, provides poor utilization of storage space, and presents a difficulty in handling, opening, and dispensing of the product, as well as disposing of the emptied packages. Due to the poor heat penetration characteristic of the puree, canned sweet potatoes are retorted for over 2 hours at 121° C., resulting in product quality within a can that varies drastically from the can center to the wall edges. Particularly at the edges, the product is often severely over-processed, resulting in dark discoloration and burnt flavor. Thus, the useful can size is frequently limited to can size number 10 (i.e., a volume of about 13 cups), and this size limitation is a major obstruction to the wider applications of canned sweetpotato puree in the food processing industry.

Other thermal processing technologies such as scraped surface heat exchangers or flash sterilization treatment also have limitations in that SPP is characterized by low thermal diffusivity (Smith et al., 1982). Fasina et al. (2003) reported that SPP has a thermal diffusivity of the order of $3 \times 10^{-7}$ m$^2$/s and a thermal conductivity of the order of 0.54 W/m·K. The low thermal diffusivity of SPP leads to very long periods of heating when conventional thermal processing methods are used in order to achieve required sterilization levels, which in turn causes degradation of the nutrients in SPP and poor product quality.

Thus, there exists a long-felt and continuing need in the art for effective methods to thermally treat foods and other biomaterials. The presently disclosed subject matter addresses this and other needs in the art.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides processes for thermally treating a flowable material while passing the flowable material as a continuous stream through a thermal treatment apparatus. In some embodiments, the process comprises (a) passing a flowable material continuously through a conduit, wherein at least a portion of the conduit is transparent to electromagnetic radiation; (b) heating the flowable material by exposing the at least a portion of the conduit that is transparent to electromagnetic radiation; and (c) mixing the flowable material within the conduit to provide for thermal equalization in at least a portion of the flowable material. In some embodiments, the flowing occurs at a constant flow rate. In some embodiments, the flowing occurs at a constant heating power input or at a constant mass mean temperature at the heating exit for the flowing biomaterial.

In some embodiments, the flowable material is selected based on at least one of rheological, dielectric, and thermophysical properties, or combinations thereof, of the flowable material. In some embodiments, the flowable material is a biomaterial. In some embodiments, the biomaterial is a food biomaterial. In some embodiments, the food biomaterial is selected based on at least one of rheological, dielectric, and thermophysical properties, or combinations thereof, of the food biomaterial.

In some embodiments of the presently disclosed subject matter, the heating results in an average bulk temperature increase rate in the flowable material of at least 1 degree Fahrenheit per second or 0.5 degrees Celsius per second. In some embodiments, one or more additional heating steps are employed. In some embodiments, the one or more additional heating steps precedes, accompanies, or follows the heating that results in an average bulk temperature increase rate in the flowable material of at least 1 degree Fahrenheit per second or 0.5 degrees Celsius per second. In some embodiments, the heating is substantially free of heating by contacting the flowable material with a surface having a temperature that exceeds a maximum temperature level of the flowable material itself.

In some embodiments of the presently disclosed subject matter, the electromagnetic radiation has a wavelength of about $1 \times 10^{-4}$ meters or greater. In some embodiments, the electromagnetic radiation has a frequency of about $3 \times 10^{12}$ waves per second or less.

In some embodiments of the presently disclosed subject matter, the mixing precedes, accompanies, or follows the heating. In some embodiments, the mixing is accomplished by altering a cross-sectional geometry of the flow. In some embodiments, the mixing occurs passively, actively, or both actively and passively. In some embodiments, the mixing is accomplished by using any combination of passive, active, or both passive and active mixing devices which serve to increase physical contact and heat exchange between regions of the flowable material having a higher temperature level and regions of the flowable material with a lower temperature level, which would not occur in the absence of the mixing devices. In some embodiments, the mixing provides at least a 10% reduction in temperature distribution variability (standard deviation) across the flowable material when compared to temperature distribution variability (standard deviation) across the flowable material in the absence of the mixing devices. In some embodiments, the process comprises placing the mixing devices at a location selected from the group consisting of one or more points of entry, one or more points within, one or more exits, and combinations thereof, of the portion of the conduit that is exposed to the electromagnetic radiation.

In some embodiments of the presently disclosed subject matter, the flowable biomaterial is not subjected to a heated surface thereby providing a heater section without burned on biomaterials and yielding beneficial process run times relative to indirect heating systems.

In some embodiments, the heating and the mixing provide a sufficient temperature for a sufficient time to accomplish one of sterilization and pasteurization of the flowable material.

In some embodiments, the process further comprises packaging the flowable material for refrigerated storage. In some embodiments, the process further comprises aseptically packaging the flowable material.

In some embodiments of the presently disclosed subject matter, the flowable biomaterial contact surface is sterilized prior to introduction of the flowable biomaterial. In some embodiments, the process comprises holding the flowable material at a predetermined temperature for a predetermined length of time, and cooling, packaging and hermetically sealing the flowable material under aseptic conditions in a sterilized package. In some embodiments, the flowable material is filled at a predetermined temperature level into a non-sterile package under one of atmospheric and increased pressure conditions in order to achieve concurrent sterilization of package surfaces in contact with the flowable material and then hermetically sealing the package.

The presently disclosed subject matter also provides a product produced by the processes disclosed herein.

The presently disclosed subject matter also provides a commercially sterile food or other biomaterial having one or more quality attributes that is preserved to a greater extent as compared to a reference food or other biomaterial that has been sterilized using a thermal treatment method comprising contacting of the reference food or other biomaterial with a surface whose temperature is consistently higher than a predetermined treatment temperature for the reference food or other biomaterial. In some embodiments, the one or more quality attributes are preserved for at least 12 weeks of storage at about 25° C. In some embodiments, the one or more quality attributes is selected from the group consisting of nutrient content, color, texture, flavor and general appearance. In some embodiments, the food or other biomaterial is one of hermetically packaged, shelf stable, and both hermetically packaged and shelf stable. In some embodiments, the food or other biomaterial is sweet potato or white (e.g., Irish) potato.

The presently disclosed subject matter also provides a commercially sterile food or other biomaterial having one or more quality attributes that is preserved to a greater extent as compared to a reference food or other biomaterial that has been sterilized using a thermal treatment method comprising contacting of the reference food or other biomaterial with a surface whose temperature is consistently higher than a predetermined treatment temperature for the reference food or other biomaterial, wherein: (i) the food or other biomaterial is one of hermetically packaged, shelf stable, and both hermetically packaged and shelf stable; (ii) the food or other biomaterial is sweet potato or white (e.g., Irish) potato; and (iii) the volume of food or other biomaterial in the package exceeds a volume of food or other biomaterial that can be accommodated in a Type 10 can. In some embodiments, no additional acid component has been added to the package.

The presently disclosed subject matter also provides a thermally treated food or other biomaterial having a quality profile comprising one or quality attributes that substantially matches a quality profile of an untreated food or other biomaterial of the same type, wherein the thermally treated food or other biomaterial is commercially sterile and shelf stable. In some embodiments, the quality attribute is selected from the group consisting of nutrient content, color, texture, flavor and general appearance. In some embodiments, the food or other biomaterial is hermetically packaged. In some embodiments, the food or other biomaterial is sweet potato or white (e.g., Irish) potato.

The presently disclosed subject matter also provides a thermally treated food or other biomaterial having a quality profile comprising one or quality attributes that substantially matches a quality profile of an untreated food or other biomaterial of the same type, wherein: (i) the thermally treated food or other biomaterial is commercially sterile and shelf stable; (ii) the food or other biomaterial is sweet potato or white (e.g., Irish) potato; and (iii) the volume of food or other biomaterial in the package exceeds a volume of food or other biomaterial that can be accommodated in a Type 10 can. In some embodiments, no additional acid component is added to the package.

The presently disclosed subject matter also provides apparatuses for thermally treating a flowable material. In some embodiments, the apparatus comprises (a) a conduit for receiving a flowable material, wherein at least a portion of the conduit is transparent to electromagnetic radiation; (b) a device for providing electromagnetic radiation to at least a portion of the conduit; and (c) a mixing structure disposed within or along the conduit to provide for thermal equalization in at least a portion of the flowable material. In some embodiments, the electromagnetic radiation can be provided at a wavelength of about $1 \times 10^{-4}$ meters or greater. In some embodiments, the electromagnetic radiation can be provided at a frequency of about $3 \times 10^{12}$ waves per second or less.

In some embodiments of the presently disclosed subject matter, the mixing structure comprises an altered cross-sectional geometry of the conduit. In some embodiments, the mixing structure comprises one or more passive mixing structures, one or more active mixing structures, or both. In some embodiments, the apparatus comprises any combination of passive, active, or both passive and active mixing structures which serve to increase physical contact and heat exchange between regions of a flowable material having a higher temperature level and regions of the flowable material with a lower temperature level, which would not occur in the absence of the mixing structures. In some embodiments, the mixing structures provide at least a 10% reduction in temperature distribution variability (standard deviation) across the flowable material when compared to temperature distribution variability (standard deviation) across the flowable material in the absence of the mixing structures.

In some embodiments of the presently disclosed subject matter, the apparatus comprises mixing structures at a location selected from the group consisting of one or more points of entry, one or more points within, one or more exits, and combinations thereof, of the portion of the conduit that is transparent to electromagnetic radiation. In some embodiments, the apparatus comprises a control device for controlling a flow through the conduit at a constant flow rate. In some embodiments, the apparatus comprises a control device for controlling a flow through the conduit at a volumetric flow rate of at least 0.25 gallons per minute. In some embodiments, the apparatus comprises a control device for controlling a power level of the device for providing electromagnetic radiation such that heating of a flowable material in the conduit can occur at an average bulk temperature increase rate in the flowable material of at least 1 degree Fahrenheit per second or 0.5 degrees Celsius per second. In some embodiments, the apparatus comprises a control device for controlling a power level of the device for providing electromagnetic radiation such that heating of a flowable material in the conduit occurs at a higher rate than heating of the conduit, such the heating of the flowable material is substantially free of heating by contacting the flowable material with a surface of the conduit having a temperature that exceeds a maximum temperature level of the flowable material itself. In some embodiments, the apparatus comprises a control device for controlling a power level of the device for providing electromagnetic radiation such that the power level can be maintained constant. In some embodiments, the apparatus comprises a control device for controlling a power level of the device for providing electromagnetic radiation such that the power level can be preset automatically or manually adjusted to a level predetermined to provide a predetermined thermal treatment of the flowable biomaterial at a predetermined mass flow rate. In some embodiments, the apparatus comprises a packaging device for one of packaging the flowable material for refrigerated storage, aseptically packaging the flowable material, and both packaging the flowable material for refrigerated storage aseptically packaging the flowable material. In some embodiments, the apparatus comprises a hold tube adapted for fluid communication with the conduit. And in some embodiments, the apparatus is capable of having the flowable biomaterial product contact surface rendered commercially sterile prior to the introduction of the flowable biomaterial.

Accordingly, it is an object of the presently disclosed subject matter to provide a method for thermally treating a flowable material. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description of the presently disclosed subject matter and non-limiting Examples.

BRIEF DESCRIPTION OF THE DRAWINGS

FIG. 26A depicts the decrease in the dynamic viscosity ($\eta^*$) of all carrot puree samples with increasing frequency, showing pseudoplastic behavior. FIG. 26B depicts the frequency dependency of the mechanical spectra of carrot puree with G' higher than G", indicating that the material can be classified as a weak gel. Small strain oscillatory tests applied to the samples in these figures allowed the evaluation of both the dynamic or complex viscosity and gel strength of the tested materials without disrupting the structural networks. These non-destructive rheological tests were performed using the same stress-controlled rheometer (Reologica Instruments AB, Lund, Sweden) as the high shear rate ramps in FIG. 5, except that the sample was subjected to gently oscillatory sweep at frequencies of 0.01 to 20 Hz.

FIG. 27A depicts the decrease in the dynamic viscosity ($\eta^*$) of all carrot puree samples with increasing frequency. FIG. 27B depicts the frequency dependency of the mechanical spectra of carrot puree with G' higher than G", indicating that the material can be classified as a weak gel. FIGS. 27A and 27B also show disrupting of the bonding and gel networks as indicated by significant decreases in both $\eta^*$ and G'. Severe disruptions of the consistency and gel strength of the carrot puree were observed with heating time beyond 30 minutes.

FIG. 28A depicts the decrease in dynamic viscosity ($\eta^*$) of all green pea puree samples with increasing frequency, showing pseudoplastic behavior. FIG. 28B shows that the green pea puree can be considered a weak gel since its mechanical spectra exhibited frequency dependency with G' higher than G".

FIGS. 29A and 29B show that in contrast to carrot puree, $\eta^*$ and G' of the green pea puree initially decreased upon heating to 75-110° C., as compared to the unheated sample, and then significantly increased at higher temperatures (120-130° C.). This trend was also exhibited among the samples heated up to 125° C. and re-circulated for 6 hours.

DETAILED DESCRIPTION

I. General Considerations

Figure 1:
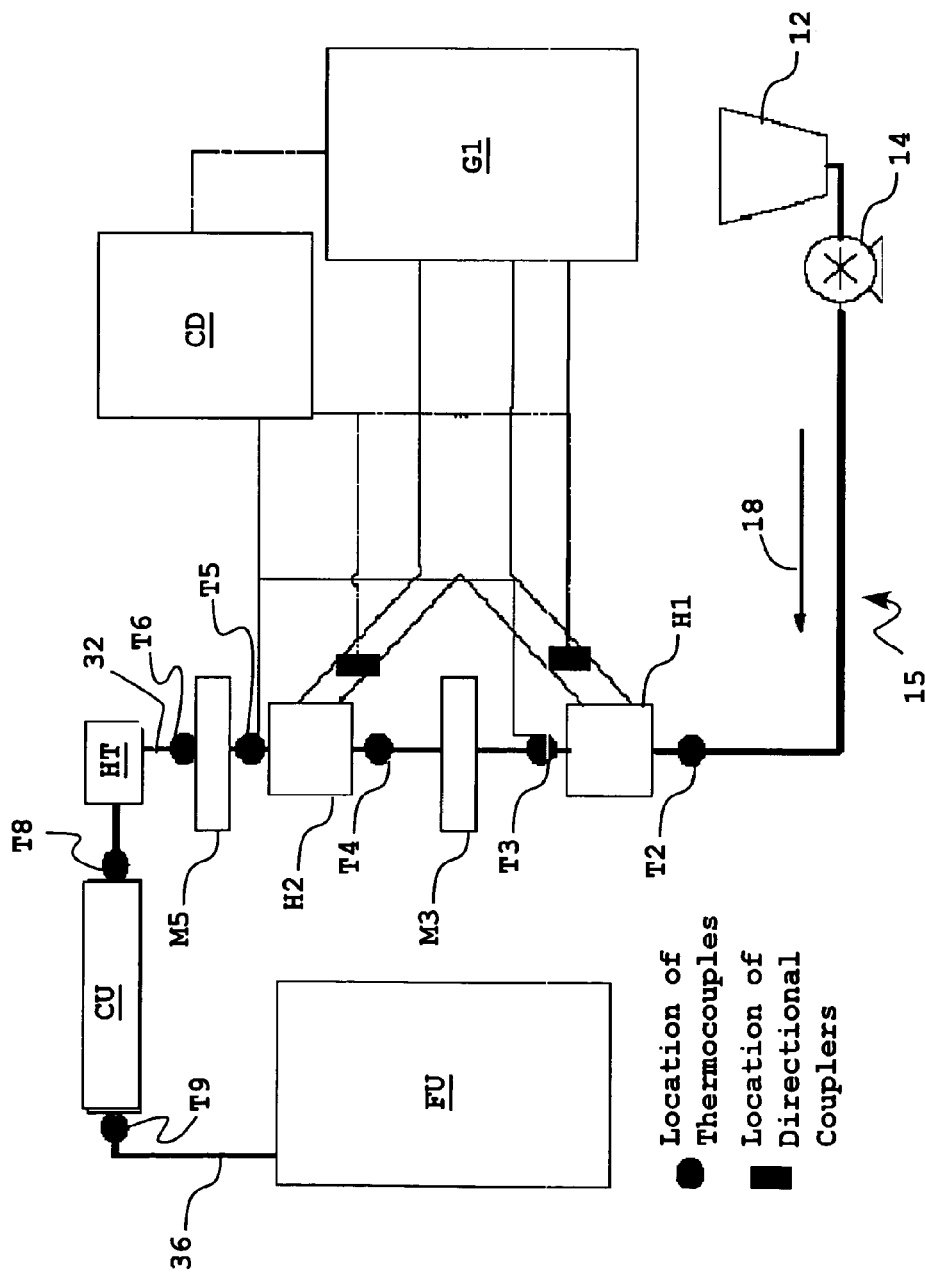
FIG. 1 is a schematic diagram of one embodiment of the thermal treatment system disclosed herein.

Continuous flow microwave heating is one of the emerging technologies in food processing, offering fast and efficient heating. Uniform heating of dairy products using this technology has been shown in previous tests (Coronel et al. 2003). The heating of food products using microwaves is governed by the dielectric properties of the material. The dielectric properties of sweetpotato puree (SPP), as reported in *Fasina* et al., 2003, are within a similar range as other products that have been identified as promising for processing using continuous flow microwave heating systems (Coronel et al., 2004). In some embodiments, the presently disclosed subject matter represents the first disclosure related to an aseptically packaged and shelf-stable vegetable puree processed by a continuous flow microwave heating system and methods for preparing the same.

The presently disclosed subject matter provides processes as well as a family of new products. The processes described are unique combinations of material (pumpable food or other biomaterial) transport, exposure to electromagnetic energy, and temperature control via active or passive temperature equalization. The mentioned temperature equalization provides a secondary means of thermal equalization by preceding, accompanying, or following a rapid temperature-increase stage achieved by the exposure of the flowing food or other biomaterial to the electromagnetic energy field (radio frequency or microwave frequency range) during pumping through a chamber or a tube made of a microwave (MW) and/or radio frequency (RF) transparent material.

The exposure to the electromagnetic energy field during material transport (pumping) through the MW and/or RF energy-transparent flow-through chamber or tube can be effected in a single or multiple stages, provided that at least one of the heating stages results in an average bulk temperature increase rate of at least 1 degree Fahrenheit per second or 0.5 degrees Celsius per second.

In some embodiments, the material being treated is transported (pumped) through the transparent chamber/tube through which this minimum temperature increase rate is effected at a volumetric flow rate of at least 0.25 gallons per minute, however different flow rates can be employed.

The mechanical temperature equalization step can be effected by using any combination of static or active mixing devices, which serve to increase physical contact and heat exchange between the continuously flowing material regions having a higher temperature level and material regions or streams with a lower temperature level that would not normally occur without the introduction of these mixing elements. Mechanical temperature equalization steps can be implemented via any individual or combinations of treatments or devices preceding, concurrent, or subsequent to the above described exposure to the electromagnetic energy field. The mechanical mixing stage typically delivers at least a 10% reduction in the temperature distribution variability (standard deviation) across the material flow when compared to the variability (standard deviation) of temperature distribution without the implemented (active or passive, preceding, concurrent, and subsequent) mixing elements; at the points of entry, points within, and/or at the exit of the electromagnetic-energy exposure stage (MW and/or RF-transparent chamber/tube).

The disclosed processes are also unique regarding the absence of heated surfaces implemented to achieving the temperature increases needed for sterilization. That means that under normal processing conditions temperatures of any and all surfaces that processed materials are directly contacting never exceed the maximum temperature level within the product mass itself.

All listed treatments and devices are implemented prior to the confirmation (by measurement) of the appropriate temperature and/or time-temperature history levels required for the achievement of commercial sterility. Following the described procedures, the food or other biomaterial can either be (a) held at a predetermined temperature level or range for a predetermined length of time (typically using a hold-tube section of an aseptic processing system), cooled and packaged and hermetically sealed under aseptic conditions into a previously and separately sterilized package; (b) filled hot (at a predetermined temperature level) into a non-sterile package under either atmospheric or increased pressure conditions in order to achieve concurrent sterilization of package surfaces in contact with the food or other biomaterial being sterilized as well as the material itself. In this instance the package is hermetically sealed while the contained product is still hot.

In either case, the resulting hermetically packaged, shelf stable, commercially sterile product comprises a food or other biomaterial with unique chemical and physical properties: quality attributes such as nutrient content, color, texture, flavor and general appearance are preserved to a much higher extent than when these products are sterilized using any other commercially available method (in-pack sterilization, hot-filling using conventional/indirect continuous flow heating methods including tube in tube heat exchangers, scraped surface heat exchangers, as well as other types of heat exchangers implementing hot-surface conventional heat exchange principles). The one or quality attributes can be preserved to in some embodiments at least a 5% greater extent, in some embodiments at least a 10% greater extent, in some embodiments at least a 15% greater extent, in some embodiments at least 20% greater extent, in some embodiments at least a 25% greater extent, and in some embodiments at least 30% greater extent or more as compared to a reference food or other biomaterial that has been sterilized using a thermal treatment method comprising contacting of the reference food or other biomaterial with a surface whose temperature is consistently higher than a predetermined treatment temperature for the reference food or other biomaterial.

The presently disclosed subject matter provides new processes utilizing a combination of available and newly developed processing elements to achieve the rapid food and other biomaterial sterilization while minimizing quality loss and maximizing nutrient retention compared with the products sterilized using conventional thermal processing (either batch or continuous). The obtained package sizes and ranges of the obtained products can range from a single-serving size to packages containing very large quantities (for example, 100 gallons or more). The product quality is uniformly high throughout the package size range, making the process and generated products compatible with a wide range of potential processed materials and markets, including further processing, institutional distribution (restaurants, cafeterias, hospitals, etc.) as well as export markets for either direct consumption or further processing into other value-added products.

The present disclosure defines the conditions of thermal process and treatment delivery for the production of thermally treated, shelf stable, commercially sterile food and other biomaterial products. The products and materials processed by the described methods can be either high acid or low acid. The presently disclosed subject matter provides the most significant advantages when applied to viscous foods and other biomaterials with high contents of carbohydrates and/or proteins.

The presently disclosed subject matter also introduces active and/or static mixing elements as a means of temperature equalization prior to, during, and/or subsequent to heating by a single-stage or multiple exposure to electromagnetic (microwave and/or radio frequency or any combination of frequencies covering the range defined as radio frequency and/or microwave) energy during continuous flow transport through a transparent flow-through chamber or tube.

The present technology to achieve the temperature levels and temperature level distribution necessary to achieve rapid sterilization for the production of shelf-stable, commercially sterile products relies primarily on heat exchange via indirect heating and contact of the food or other biomaterial with heated surfaces. This results in low rates of heat exchange and low rates of bulk material temperature increase and necessitates extended times of exposure to hot surfaces and associated extended degradation of quality attributes such as nutrient content, flavor, color, general appearance and texture. Often biomaterials are burned on to the heat exchange surface rendering reduced heat transfer and process run times. Flaking of burned on materials can also yield end product off flavors. In a very limited number of cases, more rapid heat delivery can be achieved by direct contact of the material processed with superheated steam via steam injection into the product or infusion of product into a superheated steam environment. In both cases, composition of material is negatively affected and there is a need for subsequent removal of added water from the product. Additionally, these methods are applicable only to a small and narrow group of products with very high coefficients of thermal diffusivity allowing the rapid heat dissipation necessary to achieve the needed rapid heat-up. For thicker, more viscous or homogeneous materials with suspended solid particles these methods are not applicable.

In some embodiments, one of the elements of the presently disclosed subject matter is a group of viscous or weak gel materials with a high carbohydrate content and/or high protein content and products demonstrating shear thinning with a yield stress obtained by implementing the disclosed sterilization procedure; specifically shelf-stable high carbohydrate and/or protein content products.

The unique characteristics of these products can vary from material to material but there are several common elements:
the products are in a pumpable state in order to achieve the continuous transportation mode throughout the processing and packaging stages
the retained quality attributes and characteristics of the sterilized, shelf stable products obtained by implementing the presently disclosed subject matter are closer to the original material attributes and characteristics than is the case with products and materials obtained by any other currently available processing and preservation procedure. These attributes and characteristics can be the rate of protein degradation/denaturation (minimized); rate of color, viscosity, texture, flavor, and/or nutrient content retention (maximized) and/or the rate of undesirable chemical and physical changes outside of criteria outlined above (minimized). Depending on the processed material, these criteria can refer to the retention of various chemical constituents such as thermo-sensitive vitamins (vitamin C/ascorbic acid; β-carotene/vitamin A; thiamine; etc.) or naturally occurring pigments and/or antioxidants (chlorophylls, carotenoids, anthocyanins, etc.)
the high level of retained attributes and characteristics is uniform throughout the packaged environment (i.e., the variability and the range of these characteristics is minimal in all points within the package), regardless of the package size and shape (which is not the case with the currently available similar shelf stable products)

Recently, much has been learned about the new sophisticated devices for delivery of rapid heating treatments to the continuously flowing streams of foods and other biomaterials. Treatments like rapid heating using ohmic, electroheating, radio frequency, and microwave energy all claim the speed and efficiency required to deliver the desired level and rate of heat to the processed materials.

Possibly the most sophisticated and advanced family of devices of this type are the patented cylindrical microwave heaters/reactors, produced by Industrial Microwave Systems of Morrisville, N.C., United States of America. These devices are constructed using precise modeling and fabrication of proprietary focusing structures that are carefully matched to a selected target material in order to achieve a uniform heating rate and uniform temperature distribution in the material exiting the heater/reactor exposure cavity.

Unfortunately, this precise coupling of the design to a selected set of material properties, while presenting a very clear and impressive technical advantage in the theoretical sense, also presents the most significant shortcoming of this technology in the practical application sense; and may have, over time, become the largest hurdle in its wider industrial and commercial implementation.

The reasons for this are multiple. While the achievement of a theoretically perfect (uniform) temperature distribution for a single material under a single tightly defined set of conditions would be desirable, such well defined material property sets and tightly defined sets of conditions are rarely encountered in the real world of food and other biomaterial processing.

The alternative of investing in a number of separate and individual reactor/heater devices, each requiring a disassembly and re-assembly of a process line in order to accommodate a narrowly defined material from a possibly very wide range that a processor could target, would be very costly and cumbersome.

Property and process parameter conditions that should be considered in the implementation of continuous flow microwave and/or radio frequency treatment are numerous, and can be inter-dependent on other conditions such as temperature, implemented shear rates, and accompanying physical and chemical changes occurring in the material during the process, including but not limited to the following:

Dielectric properties (properties determining the rate and efficiency of conversion of microwave energy into heat) of the material are dependent on temperature, composition, and accompanying physical and chemical changes. Foods and other biomaterials are well-known for their variability of composition so even when the treatment is perfectly matched to a certain set of material properties, natural variations due to growing conditions, cultivation practices, types of cultivar, season, presence or absence of pests as well as local and seasonal climate can affect the composition of the materials and therefore the resulting match and efficiency and quality of microwave and/or RF treatment.

Design of the focused applicator devices is typically centered on a single or a narrow range of dielectric properties (assumed on the basis of a single or a narrow temperature range of exposure during processing). However, temperature differences achieved during heating far exceed the ranges assumed in the design of processing elements. This leads in some cases in reduction in energy coupling efficiency as well as reduced temperature uniformity and expanded (in some cases drastically) temperature distribution variabilities for product types and temperature ranges not taken into account during the design.

Flow distribution of product during and subsequent to heating is dependent on temperature range, volumetric and mass flow rates, and physical properties of transported material such as viscosity and texture. In most cases these properties are both temperature and shear rate dependent. In addition to the typical cases of laminar and turbulent flow profiles there is an infinite number of intermediate and unique flow distribution scenarios including channeling of material caused by local heating and reduction of viscosity due to increased temperature and shear rates. This all adds up to an extremely complex set of encountered and potential conditions which cannot be reasonably addressed and incorporated into a well-controlled sterilization process using a selected narrow set of conditions for heating model approach.

Sterilized foods and other biomaterials undergo an overwhelming number and variety of chemical and physical changes during exposure to the sterilization level thermal treatments. These include the uptake and release of water from various biopolymer and macromolecule structures present in the foods and other biomaterials (water associated with protein, carbohydrate and polysaccharide molecules). This water can be bound and released based on a variety of conditions, including, but not limited to pH, temperature, concentration of solutes or solids, ionic strength of the environment, etc. Additional changes affecting the dielectric, flow and heat dissipation behavior of the processed material include unfolding and denaturation of proteins, formation and breakdown of gels (such as pectin and starch based gels), changes in physical state such as melting and/or solidification of lipid constituents. Finally, chemical changes and reactions affect not only the physical and especially dielectric properties but also result in generation (exothermic) or consumption (endothermic) of thermal energy, additionally resulting in associated temperature increases and/or reductions in the material, unrelated to the heating process and method itself.

Taken together, all of the listed and additional factors and parameters can limit the application of narrowly defined and targeted focusing devices to a few cases where either these changes are non-existent or minimal or where the thermal diffusivity properties or the natural flow turbulence are so high as to provide a concurrent temperature equalization effect with the flow. Unfortunately, these materials are typically of low value, falling short of justifying the cost of investment in a sophisticated, high cost sterilization equipment such as RF or MW heating units, and can be easily and more economically processed by other available means.

Furthermore, currently available modeling and simulation techniques and computing equipment can only provide an approximation of the listed changes and variations. Very valuable information and understanding can be gained from these models as their sophistication increases and more elements are integrated into simulations. However, they still currently fall short of providing a sufficient, comprehensive basis to address all elements and parameters needed to interpret these complex processes appropriately.

The presently disclosed subject matter thus presents a practical solution to these concerns. By incorporating the additional mixing and temperature equalization devices into the process under a wider set of operating conditions and much wider target range of potential materials while maintaining the use of a single type or construction design of energy focusing device, at least two advantages can be achieved. For example, by implementation of static or active mechanical mixing as an approach for temperature equalization preceding, accompanying, or following the heating via exposure to an electromagnetic energy field, the presently disclosed subject matter provides a practical strategy for expanding the range of targeted processed products, temperature range, flow rate, and distribution conditions, and can additionally accommodate and equalize effects from all parameters and events in the above list; and (b) when combined with active or static mixing, the methods and implementation of the expensive focusing structures is not as critical for the rapid achievement of sterilization-level temperatures at acceptable uniformity and distribution conditions. Stated another way, the apparatuses and methods described herein can expand the range of applicability of alternative focused and non-focused methods of electromagnetic energy exposure and delivery of rapid sterilization rates and effects.

A large number and variety of foods and other biomaterials are compatible with the disclosed processes and apparatuses. Pureed and homogenized fruits can be treated to the appropriate temperature levels (95-100° C.) for sterilization preservation of high-acid materials and either filled hot or cooled and filled under aseptic conditions.

Preliminary data has been generated by the co-inventors for more than 50 different foods and materials using the recirculated heating technique to evaluate and illustrate the temperature distributions encountered and the need to address these distributions by static or active mixing during the process.

The disclosures of the following patents and patent publications are incorporated herein by reference in their entireties: U.S. Pat. Nos. 6,797,929; 6,583,395; 6,406,727; 6,265,702; 6,121,594; 6,087,642; and 5,998,774; U.S. Patent Application Publications 20030205576 and 20010035407; and PCT International Patent Application Publications WO 0143508; WO 0184889; and WO 0036879.

II. Definitions

While the following terms are believed to be well understood by one of ordinary skill in the art, the following definitions are set forth to facilitate explanation of the presently claimed subject matter.

Following long-standing patent law convention, the terms "a", "an", and "the" refer to "one or more" when used herein, including in the claims.

As used herein, the term "about", when referring to a value or an amount, for example, relative to another measure, is meant to encompass variations of in some embodiments ±20%, in some embodiments ±10%, in some embodiments ±5%, in some embodiments ±1%, and in some embodiments ±0.1% from the specified value or amount, as such variations are appropriate.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed in some embodiments as a "p-value". Those p-values that fall below a user-defined cutoff point are regarded as significant. In some embodiments, a p-value less than or equal to 0.05, in some embodiments less than 0.01, in some embodiments less than 0.005, and in some embodiments less than 0.001, are regarded as significant.

The presently disclosed subject matter provides a continuous flow method for thermally treating a flowable material. As used herein, the term "flowable material" refers to any material that can be flowed from one point to another in a substantially uniform manner. For example, in some embodiments, a flowable material can be moved from one place to another under laminar flow. In some embodiments, a flowable material comprises a highly viscous/semi-solid material that is shear thinning or shear thickening characterized with a yield stress.

In some embodiments the biomaterial is selected based on the rheological, dielectric, and thermophysical properties of the biomaterial. In some embodiments, the biomaterial has one or more characteristics selected from the group consisting of high starch content, high protein content, high solids content, a high viscosity (for example, a viscosity at about 25° C. that renders conventional thermal treatment processes undesirable), and low thermal conductivity (for example, (less than 1 W/m·K). In some embodiments, the biomaterial includes thick vegetable purees, weak gels of biomaterials, and the like. Representative flow properties and yield stress of thick/viscous foods or biomaterials including sweet potato puree are presented in Tables 1 and 2.

TABLE 1

Flow Properties of Various Food Biomaterials at 25° C.

| Food Product | Solid (%) | Consistency coefficient (K) | Flow behavior index (n) | Yield stress (Pa) |
| --- | --- | --- | --- | --- |
| Sweetpotato puree A[1] | 16 | 18.8 | 0.39 | 89 |
| Sweetpotato puree B[2] | 20 | 13.39 | 0.25 | 10 |
| Baby food, banana (Gerber) | 15 | 28 | 0.59 | 28 |
| Baby food, peach | 16 | 1.4 | 0.6 | 13 |
| Pear puree | 18 | 2.3 | 0.49 | 3.5 |
| Pear puree | 45.7 | 35.5 | 0.48 | 33.9 |
| Apple sauce | 11 | 11.6 | 0.34 | 11.6 |
| Apple sauce | 18 | 34 | 0.42 | 34 |
| Tomato paste | 30 | 208 | 0.27 | 206 |

[1]Co-inventors' data reported in Coronel et al., 2004.
[2]Reported in Kyerreme et al., 1999.

TABLE 2

Yield Stress of Fluid Foods

| Product | $\sigma_o$ (Pa) | Measurement Method | Source |
| --- | --- | --- | --- |
| Ketchup | 22.8 | extrapolation | Ofoli et al., 1987 |
| Mustard | 34.0 | extrapolation | Ofoli et al., 1987 |
| Miracle Whip | 54.3 | extrapolation | Ofoli et al., 1987 |
| Apricot puree | 17.4 | extrapolation | Ofoli et al., 1987 |
| Milk chocolate | 10.9 | extrapolation | Ofoli et al., 1987 |
| Minced fish paste | 1600-2300 | extrapolation | Nakayama et al., 1980 |
| Mayonnaise | 24.8-26.9 | stress to initiate flow | De Kee et al., 1980 |
| Ketchup | 15.4-16.0 | stress to initiate flow | De Kee et al., 1980 |
| Tomato paste | 83.9-84.9 | stress to initiate flow | De Kee et al., 1980 |
| Raw meat batter | 17.9 | extrapolation | Toledo et al., 1977 |
| Tomato puree | 23.0 | stress decay | Charm, 1962 |
| Applesauce | 58.6 | stress decay | Charm, 1962 |
| Tomato paste | 107-135 | squeezing flow | Campanella & Pelegi, 1987 |
| Ketchup | 18-30 | squeezing flow | Campanella & Pelegi, 1987 |
| Mustard | 52-78 | squeezing flow | Campanella & Pelegi, 1987 |
| Mayonnaise | 81-91 | squeezing flow | Campanella & Pelegi, 1987 |
| Applesauce | 45-87 | squeezing flow | Campanella & Pelegi, 1987 |
| Applesauce | 46-82 | vane method | Qui & Rao, 1988 |
| Ketchup | 26-30 | vane method | Missaire et al., 1990 |
| Spaghetti sauce | 24-28 | vane method | Missaire et al., 1990 |
| Tomato puree | 25-34 | vane method | Missaire et al., 1990 |
| Pumpkin filling | 20 | vane method | Missaire et al., 1990 |
| Applesauce | 38-46 | vane method | Missaire et al., 1990 |
| Baby food, pears | 49 | vane method | Missaire et al., 1990 |
| Baby food, peaches | 25 | vane method | Missaire et al., 1990 |
| Baby food, carrots | 71 | vane method | Missaire et al., 1990 |

See also Steffe, 1996.

As used herein, the term "thermally treating" and grammatical variants thereof refer to exposing a flowable material (for example, a biomaterial) to conditions whereby the temperature of all of the flowable material, either over time or upon exposure to electromagnetic radiation with mixing, is increased to an appropriate level to effect the treatment. In some embodiments, a thermal treatment is designed to pasteurize or sterilize a biomaterial.

As used herein, the terms "pasteurization" and "pasteurized" refer to treatments sufficient to kill sufficient pathogenic microorganisms contained within the biomaterial being treated to render the biomaterial edible or otherwise administrable to a subject without threat of infection by, for example, *Salmonella, Listeria*, or other pathogenic microorganisms. Pasteurization can be thought of as a treatment that, for all practical purposes, renders pathogenic microorganisms into a state in which they are incapable of reproducing or growing under refrigerated conditions. Pasteurization methods cause in some embodiments at least a four log cycle reduction, in some embodiments at least a six log cycle reduction, and in some embodiments at least a nine log cycle reduction, of bacteria in the product.

As used herein, the term "ultrapasteurization" refers to pasteurization that results in a pasteurized product with a salable shelf life under ambient or refrigerated conditions (e.g., 4° C. or less, but above freezing) greater than that obtainable using previously known pasteurization methods. See e.g., U.S. Pat. No. 4,808,425 (the disclosures of all patents cited herein are incorporated herein in their entireties). As used herein, the phrase "salable shelf life" refers to an amount of time that a product can be stored and/or available for sale to a consumer before some characteristic that changes during storage alters the product to an extent that would make the product unappealing to the consumer. Representative characteristics that can change during storage of a product include, but are not limited to color levels, viscosity levels, taste characteristics, aromas, and microbial levels. Thus, ultrapasteurization methods produce extended salable shelf life products: for example, products having shelf lives of in some embodiments more than 10 days, in some embodiments more than 14 days, in some embodiments 4 to 6 weeks, and in some embodiments up to 36 weeks or more.

In some embodiments, ultrapasteurization refers to a) sterilizing the contact surface area of the processing unit prior to introduction of the biomaterial, b) providing a thermal treatment to the biomaterial greater than that normally associated with pasteurization but less than would be considered commercially sterile, although treatments in the range of the commercially sterile range can be used, c) packaging in an Extended Shelf Life (ESL) filler and/or aseptic filler and d) maintaining the product under refrigeration during storage. Ultrapasteurized product is not considered a low-acid shelf stable product requiring a no rejection letter from the US Food and Drug Administration allowing production but must be refrigerated and has a limited shelf life.

In some embodiments, the thermal treatment results in a biomaterial that is shelf stable. As used herein, the term "shelf stable" refers to a biomaterial that can be stored for extended periods of time at room temperature without spoilage or microbial growth when compared to the same biomaterial that had not been thermally treated as described herein. A shelf stable biomaterial can be stored at room temperature for in some embodiments more than 10 days, in some embodiments more than 14 days, in some embodiments 4 to 6 weeks, and in some embodiments up to 36 weeks or more without spoilage or microbial growth. It is not uncommon for shelf stable commercially sterile product to have shelf lives of one year or greater.

Shelf stable and commercially sterile can be used interchangeably for the purpose of the presently disclosed subject matter. Elements include a) sterilizing the contact surface area of the processing unit prior to introduction of the biomaterial, b) providing a thermal treatment to the biomaterial that eliminates the risks, within statistical limits, for the growth of microorganisms and their spores, at ambient temperatures c) packaging in hermetically sealed containers using an aseptic filler and d) maintaining the product at ambient temperature during distribution storage. Low-acid shelf stable product requires a no rejection letter from the US Food and Drug Administration allowing production.

It should be noted that "shelf stable" and "salable shelf life" are not necessarily interchangeable terms. For example, a product can be shelf stable for a period of time that exceeds its salable shelf life. Given that certain changes that can occur to a product over time are unrelated to microbial growth and can negatively affect a salable shelf life, a given product's salable shelf life is typically shorter than the time period during which is it otherwise shelf stable.

The term "aseptic packaging" or packaged in an aseptic filler means to the exclusion of microorganisms and their spores other than those carried by the product itself. Aseptic packaging fillers are pre-sterilized prior to production runs. In some embodiments, the aseptic packaging material is pre-sterilized prior to the introduction of heat-treated biomaterial.

By the term "biomaterial", it is meant that any material that includes a biological component, such as a protein, starch, or sugar. Representative biomaterials are those amenable to processing using a thermal process, such as a continuous flow thermal process. In some embodiments, a biomaterial is a food or a food product.

The term "biomaterial" is also meant to refer to solid or fluid materials or products that are susceptible to deviations from a standard quality or characteristic if exposed to certain environmental conditions, or if not properly treated so as to reach the standard characteristic or quality. In some embodiments, "biomaterial" refers to a food material. The term "biomaterial" is thus also meant to include a material or product that is to be ingested by or introduced into a consumer.

Foods and other biomaterials, for example, are susceptible to deviations from a standard quality or characteristic. Microbial growth in the food or other biomaterial contained in a package can occur if, among other things, the food or other biomaterial in the package is not properly refrigerated or is not thermally treated to a sufficient level to kill microbes and their spores within the food or other biomaterial. Microbial growth produces deviations in a characteristic in the food or other biomaterial from a standard characteristic. For example, microbial growth can produce gases within a package containing a food or other biomaterial. The gases, mainly carbon dioxide produced by microbial metabolic processes, represent a deviation from a standard characteristic of the food or other biomaterial in a like package in that no such gases should be present in a standard quality food or other biomaterial in a like package. Further, the microbial growth itself can represent a deviation for the standard, that is, no microbial growth.

Other examples of a "biomaterial" include pharmaceuticals, blood and blood products, and personal health products like shampoo. While personal health care products like shampoo are not meant to be ingested by a consumer, they usually include a biological component like a protein.

By the term "characteristic", it is meant a feature of the biomaterial or of the package for a biomaterial. Particularly, the term "characteristic" is meant to describe a feature of the biomaterial or of the package of biomaterial that determines whether or not the biomaterial or package is suitable for use by and/or ingestion by a consumer. The term "quality attribute" can include any characteristic disclosed herein that might be desirable for a given biomaterial. The term "quality profile" can thus refer to any combination of characteristics, or quality attributes, disclosed herein that might be desirable for a given biomaterial.

By the term "standard characteristic", it is meant, then, a characteristic of the biomaterial and/or package for a biomaterial which indicates that the biomaterial and/or package for a biomaterial is suitable for use by a consumer. In some embodiments, the term "standard characteristic" can mean a standard or a quality level for a given characteristic against which unknown characteristics can be compared.

For example, the characteristic and the standard characteristic of the biomaterial can each comprise a characteristic of the composition of the biomaterial. As used herein, a "characteristic" can be a "quality attribute", which is intended to refer to a characteristic of the biomaterial that when varied affects the desirability of the treated biomaterial for the consumer. Representative quality attributes include, but are not limited to, nutrient content, color, texture, flavor, general appearance, fat content, water composition, and combinations thereof.

As used herein, the term "thermal equalization" refers to a condition whereby the temperature of a biomaterial is substantially uniform through a chosen region (for example, a cross section). Thus, "thermal equalization" is a state wherein the temperature distribution variability across the chosen region is minimized. While it is not required that the temperature of the chosen region be within any set number of degrees, thermal equalization can encompass temperature variability of in some embodiments not more than 20° C., in some embodiments not more than 15° C., in some embodiments not more than 10° C., in some embodiments not more than 8° C., in some embodiments not more than 6° C., in some embodiments not more than 5° C., in some embodiments not more than 3° C., and in some embodiments not more than 1° C. Alternatively, thermal equalization can be expressed in terms of a percent variability through a chosen region (for example, a cross section). Thus, a percent variability can encompass in some embodiments less than a 20%, in some embodiments less than a 15%, in some embodiments less than a 10%, in some embodiments less than an 8%, in some embodiments less than a 5%, in some embodiments less than a 3%, in some embodiments less than a 2%, and in some embodiments less than a 1% difference between the highest and the lowest temperatures present within the chosen region.

In some embodiments, thermal equalization encompasses temperature differences that are small enough such that the minimum temperature is sufficient to accomplish the goals of the thermal treatment without negatively affecting characteristics of interest of the biomaterial at any site within the chosen region.

In some embodiments, mixing the flowable material facilitates thermal equalization. In some embodiments, mixing is accomplished by static or dynamic change of shape, profile and/or area size of the cross-section of the flow-through region of a conduit, preceding, concurrent or subsequent to heating/exposure to electromagnetic energy. Shape can refer to the cross-sectional geometry of the conduit, which can be varied from round to elliptical to triangular etc.; change in profile can refer to the inclusion of inserts such as single or multiple mixing bars, shafts, or other such protrusions; and size of the area can refer to an increase or decrease in the flow-through diameter of the conduit as well as variations in the flow-through area by having different cross sections and/or attachments to the mixing bars or static flow obstructions.

As is well known in the art, by the term "hermetically sealed", it is meant any sealing process wherein a package including a material (e.g., a biomaterial) is sealed to the exclusion of microbes and their spores. In the case of a biomaterial, the biomaterial is treated prior to sealing, whether thermally or otherwise, to remove microbes and their spores. An appropriately treated biomaterial that is appropriately hermetically sealed in a package will likely remain fit for ingestion or other use by a consumer for an extended period of time, assuming other appropriate storage conditions are implemented as necessary. Thus, the term "hermetically sealed package" or alternatively, the term "hermetically packaged" can be further defined as a package having a seal that keeps a biomaterial contained within the package fit for ingestion or other use by a consumer for an extended period of time.

By the term "sterilizing", "sterilization", and grammatical variants thereof, it is meant that the product is free of viable organisms or spores capable of growing under any conditions (can not be isolated and grown under optimum laboratory conditions.) In some embodiments a commercial sterile product is desired. By the term "commercially sterile" it is meant the condition achieved by application of heat, sufficient, alone or in combination with other ingredients and/or treatments to render the product free of microorganisms and/or spores capable of growing in the product at conditions at which the product is intended to be held during distribution and storage non-refrigerated, ambient temperatures. Commercially sterile products may have spores that could germinate and grow under some conditions but not storage conditions intended for the product. In no case would any spores that grow in the commercially sterile product be pathogenic.

By the term "thermal property", it is meant any property of a flowable material (e.g., a biomaterial) that is related to the way the material (e.g., biomaterial) accepts or releases heat. Examples include, but are not limited to, thermal conductivity, or rate of heat penetration, rate of cooling, temperature, and combinations thereof. Representative thermal properties include rate of temperature changes, including rate of heat penetration and rate of cooling.

The methods of the presently disclosed subject matter can be employed in continuous flow treatment. As used herein, "continuous flow treatment" refers to methods in which a continuous stream of product is maintained in the treatment apparatus being used. Continuous flow thermal processing equipment can comprise heating, holding, and cooling sections, in which a continuous stream of product is maintained.

The equivalent point method can be used for evaluating thermal treatments be applied in practicing the presently disclosed subject matter when continuous flow treatment is used. This method describes the total thermal treatment received by a product in continuous flow equipment. Procedures for using the equivalent point method for analyzing the thermal effects on products during continuous flow heating have been previously outlined (Swartzel, 1982; Swartzel, 1986; U.S. Pat. No. 4,808,425) and are known to those skilled in the art.

In some embodiments, the presently disclosed subject matter utilizes that portion of the electromagnetic spectrum associated with microwaves and with radio reception (i.e., radio waves having a frequency of from about 500 Kilohertz (KHz) to about 110 Megahertz (MHz); or radio waves with wavelengths from about 1 meter to $10^4$ meters). In particular, the presently disclosed subject matter uses high frequency electromagnetic radiation. As used herein, the phrase "high frequency electromagnetic radiation" (HFER) refers to electromagnetic radiation understood by those in the art to include radio frequencies and microwaves. Thus, HFER can have a frequency of about $3\times10^{12}$ waves per second or less, in some embodiments, from about 15 MHz to about 300 GHz. HFER can have wavelengths of about $1\times10^{-4}$ meters or greater, and in some embodiments from about 1 millimeter to about 20 meters. Alternating currents generate electromagnetic waves of a desired frequency and wavelength, which travel at a speed characteristic of the media in which they are traveling. The wavelength ($\lambda$) of a particular wave in a given flowable material (e.g., a biomaterial) is determined from knowledge of the frequency f, which remains constant (a function of the generator), and v, which depends on the velocity of the wave in the product.

In some embodiments, the presently disclosed subject matter involves microwave heating. The frequencies employed for microwave heating encompass the entire range classified as microwaves. Only four specific frequency bands are used for industrial heating applications in the United States. These four bands were allocated by the Federal Communications Commission and are called the Industrial-Scientific-Medical or ISM frequencies. These bands are at frequencies of 915 MHz, 2450 MHz, 5800 MHz, and 24,125 MHz. Users of industrial microwave equipment are permitted to generate unlimited power on these four bands, chosen so that they do not interfere with radar and communications. While the presently disclosed subject matter can incorporate the application of ISM frequency heating, the presently disclosed subject matter is not limited to these selected frequencies.

The presently disclosed subject matter utilizes HFER to produce heat within the products being treated, causing microbial destruction without loss of product functionality, and yielding reduced or eliminated product deposition on surfaces in direct contact with the biomaterial. Microbial inactivation using electromagnetic waves can be due to thermal effects, as in conventional heating processes, can include thermal effects resulting from unknown interactions between biochemical constituents of microbes and an electromagnetic field, and combinations thereof. See e.g., Adey, 1989. However, electromagnetic waves producing heat generally yield microbial destruction at a level similar to that produced using conventional heat only. See e.g., Goldblith, 1975.

In the presently disclosed subject matter, HFER is converted to heat as it interacts with flowable materials (e.g., biomaterials). Absorption of electromagnetic energy increases the kinetic energy of the molecules of the absorbing medium, and increases the temperature of the absorbing medium. Because heat is generated within the product being heated, contact with heated surfaces acting as heat transfer surfaces is not required. Thus, fouling or burning of biomaterials in contact with heated surfaces is reduced or eliminated when using HFER treatment. In continuous flow equipment, this allows extended process run-times and yields greater efficiency by achieving higher through-put of product before cleaning of equipment is required, while producing product with good functional characteristics and eliminating burned flaked off material that had adhered to the heat exchanger wall yielding potentially off flavors.

Most continuous flow treatment processes using indirect heat exchangers are designed to maximize turbulent, high-shear flow in order to achieve efficient heat transfer throughout the flowable material (e.g., biomaterial). In HFER heating, particulate matter heats at the same rate as liquids, allowing continuous flow treatment apparatuses to be designed with less concern about the flow characteristics of the biomaterial. Shear stress on the proteins can be reduced, and the need to make highly homogeneous liquids from biomaterials can be eliminated. Thus, low shear pumps can be employed in practicing the presently disclosed subject matter in continuous flow apparatuses.

HFER heating is distinguished from ohmic heating in that the heater design and controls are not dependent on the specific electrical conductivity of the material being heated. For example, different biomaterials can have sufficiently different electrical conductance such that it is extremely difficult to heat them with the same ohmic heater, while a HFER process and apparatus in accordance with the presently disclosed subject matter should be able to heat each product equally efficiently. HFER heating does not create free radicals and the resulting deterioration of flavor as is found when high energy ionizing radiation is used to treat various biomaterials.

Any method for generating electromagnetic waves of the desired frequencies can be used to carry out the presently disclosed subject matter. Any commercial or industrial generator capable of producing high frequency radio waves or microwaves can be used. Generators can be added in parallel or in series to increase production or temperature. Generators can be harmonically suppressed or otherwise structured to meet standards for desired electromagnetic emissions.

In apparatus used for practicing the methods of the presently disclosed subject matter, structures which are interposed between the product to be treated and the HFRW generator are constructed of material that is transparent to electromagnetic radiation. As used herein, the phrase "transparent to electromagnetic radiation" refers to a characteristic of a material whereby electromagnetic radiation (for example, radio frequencies or microwaves) substantially passes through the material. Similarly, the terms "radiolucent" and "microwave transparent" refer to material that is permeable to radio waves and microwaves, respectively. For example, in a continuous flow apparatus as exemplified in FIG. 1, the conduit carrying the biomaterial adjacent to the HFRW generator is manufactured of material that is radiolucent or microwave transparent. As used herein, the term "radiolucent" refers to a material that is essentially transparent to radio waves of the frequency used in the methods of the presently disclosed subject matter; while the material can be permeable to electromagnetic waves of other frequencies, this is not required. Similarly, the term "microwave transparent" refers to a material that is essentially transparent to microwaves. Examples of suitable radiolucent and/or microwave transparent materials include polytetrafluoroethylene (e.g., the products marketed as TEFLON™ or HOSTAFLON™), and polycarbonate resins such as LEXAN™, or glass (e.g., KIMAX™ tempered glass process pipe). As would be apparent to one skilled in the art, the use of radiolucent and/or microwave transparent materials is required only to the extent necessary to allow sufficient exposure of the biomaterial to the HFER.

In continuous flow apparatus used with methods of the presently disclosed subject matter, any device for establishing a continuous stream of flowable material (e.g., biomaterial) can be used to carry out the presently disclosed subject matter. An exemplary pump that can be used to establish the stream is a positive displacement pump, though a positive displacement pump (timing pumps) are generally needed to precisely define the holding time of a product stream in a holding section. Positive displacement pumps can be used in combination with other pumping devices, such as centrifugal pumps.

Upon a review of the present disclosure, it will be apparent to one skilled in the art that an adequate flow of flowable material through the apparatus must be produced so that the flowable materials are conveyed through the treatment apparatus at an adequate rate. Representative devices for producing a flow of flowable material (e.g., a biomaterial) include, but are not limited to, gravity flow conduits and pumps such as SINE PUMPS™ (Sine Pumps, Curacao, Netherlands Antilles), auger type pumps, or combinations thereof. Reversible thermal set carrier medium gels can also be used (e.g., methylcellulose solutions).

Using the methods and apparatuses of the presently disclosed subject matter, it is possible to treat biomaterials from temperatures below 40° F. (but above freezing) up to temperatures above 160° F., but below cooking temperatures. The product can then be held at the final temperature for a period of time adequate to destroy harmful and spoilage bacteria, as discussed below.

An optional preheating step can be employed prior to HFER treatment to preheat the flowable material (e.g., biomaterial) to a temperature between about 120° F. and 155° F. Preheating systems can comprise, but are not limited to, conventional heating systems such as plate, swept, tube heat exchangers, ohmic systems, steam injection, hot water injection, hot fluid food injection, etc.

In some embodiments, the total thermal treatment received by a flowable material (e.g., a biomaterial) during the process must be sufficient to reduce the microbiological population in the product to an acceptable level. Proper thermal treatment can be facilitated by presetting the holding times. The term "holding time", as used herein, has its ordinary meaning as used in the industry.

In some embodiments, the thermal treatment is sufficient to produce a product having a shelf life of about four weeks to about thirty-six weeks under ambient or refrigerated conditions, and in some embodiments a product having a shelf life of about eight weeks to about thirty-six weeks under ambient or refrigerated conditions. The term "refrigerated," as used herein, means stored at or below a temperature of 4° C. but above freezing.

To produce uniformly treated flowable material (e.g., biomaterial), each unit of the flowable material (e.g., biomaterial) should receive substantially the same thermal treatment. This can be accomplished in accordance with the presently disclosed subject matter by exposing each unit of flowable material (e.g., biomaterial) to the same HFER energy and mixing, with other conditions being substantially uniform.

Following thermal treatment the product can then be cooled using conventional cooling systems such as, but not limited to, plate heat exchangers, swept surface heat exchangers, liquid nitrogen injection, $CO_2$ gas injection or injection of other inert gases, or immersion in a water bath.

Elements of continuous flow apparatus are interconnected by a product line formed of any conventional sanitary material, such as stainless steel tubing.

To obtain a product with reduced quantities of microorganisms, the treatment apparatus can be sterilized before the biomaterial is passed therethrough. Sterilizing can be accomplished by passing hot water under pressure through the treatment apparatus, as is known in the art, so that hot water is contacted to those surfaces which contact the product at a temperature and pressure and for a time sufficient to sterilize these surfaces. Any other method of sterilization of treatment apparatuses can also be used.

Unpackaged flowable material (e.g., biomaterial) can be aseptically packaged after treatment. "Aseptically packaged" means packaged to the exclusion of microorganisms other than those carried by the material itself, if any. Equipment suitable for aseptically packaging biomaterial, such as the TETRA PAK™ TBA/9, the TETRA PAK™ TR7-ESL, the TETRA PAK™ Model AB-3-250 (all available from Tetra-Pak Inc., Vernon Hills, Ill., United States of America), and the Evergreen EQ-4 (Evergreen Packaging Equipment, Cedar Rapids, Iowa, United States of America), is commercially available. Also useful in carrying out this step is equipment which packages the product to the substantial exclusion of microorganisms, known in the industry as "clean fillers," but the greater exclusion of microorganisms provided by aseptic fillers makes aseptic fillers preferable, particularly in view of the ability of *Listeria* and certain other microorganisms to grow under refrigerated conditions.

A homogenization step for unpackaged flowable biomaterial can optionally be included, but generally is not required. The term "homogenization" as used herein, means to subject a product to physical forces to reduce particle size. Such procedures are known in the art, and can be carried out on different types of equipment. In some embodiments, this homogenizing step is carried out with homogenizing equipment at total pressures of from about 500 pounds per square inch (p.s.i.) to about 3,000 p.s.i.

Figure 37:
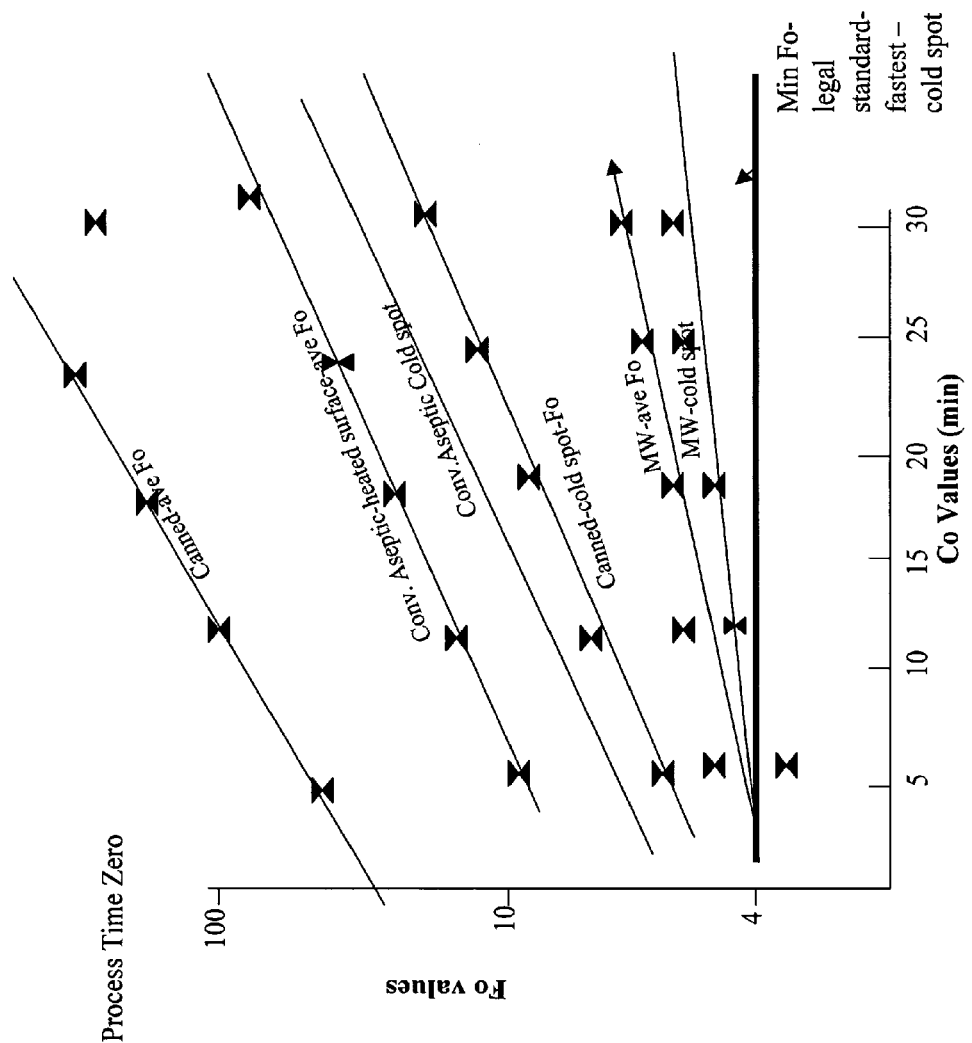
FIG. 37 is a schematic plot comparing Fo values and Co values of a MW-based process as disclosed herein versus conventional aseptic processing and canning approaches.

Referring now to FIG. 37, another description of a quality profile is provided, which pertains in part to concept of what can be shown for time zero. Particularly, FIG. 37 shows that the MW technique is very uniform, both in cold spot and average (bulk) heating. The Co values correlate to quality factors-design with Ea values (z values in the quality constituent range). Thus, this industry standard can be used to represent the quality changes (for the example, the quality profile) in the product at time zero. The cold spot is also shown for an aseptic conventional flow product (for example, purees typically flow as laminar flow-thus 2× can optionally be used-fastest to bulk). It is thus believed that there is a large difference between meeting the minimum legal Fo for the cold spot and the bulk that is exposed for a MW-based process as disclosed herein versus conventional aseptic processing and canning approaches. For example, to get the cold spot in a canning approach (2 hours of heating—#10 can) to the minimum Fo value the bulk would be 80 min. Also, for canning vegetable purees, the retorting time required for can size no. 10 is 165 minutes at 121 C (Lopez 1987), the Fo values should be longer time periods.

With respect to shelf life, it is believed that the presently disclosed product are within the industry standards for usable product (for example, based on viscosity, color, aroma and trained sensory evaluation and remains shelf stable through 18 months as compared to usable canned and aseptic, traditional, on the market). However, referring to FIG. 37, it is believed that by starting at time zero with much higher bulk (average) quality retention (based on the Co value-which can also be shown as a ratio of 100% time zero raw to, for example, 95% time zero processed quality retention) and assuming the same kinetic degradation of quality in all three methods stored at ambient temperature, one might see 30-50% loss at time zero for the bulk in conventional canned product and conventional aseptically processed product. Thus, if it assumed that the difference stays the same over storage, the quality at the 18 months level should be still satisfactory for a product as disclosed herein, while poor for the canned and for a conventional aseptic method.

FIG. 37 is thus believed to demonstrate the MW advantages over the canned and conventional aseptic methods. Additional advantages of a MW approach as disclosed herein include space requirements, e.g., <1 foot MW heating tube vs. 250 ft for conventional technology.

III. Apparatuses

III.A. Treatment Apparatuses

Figure 9:
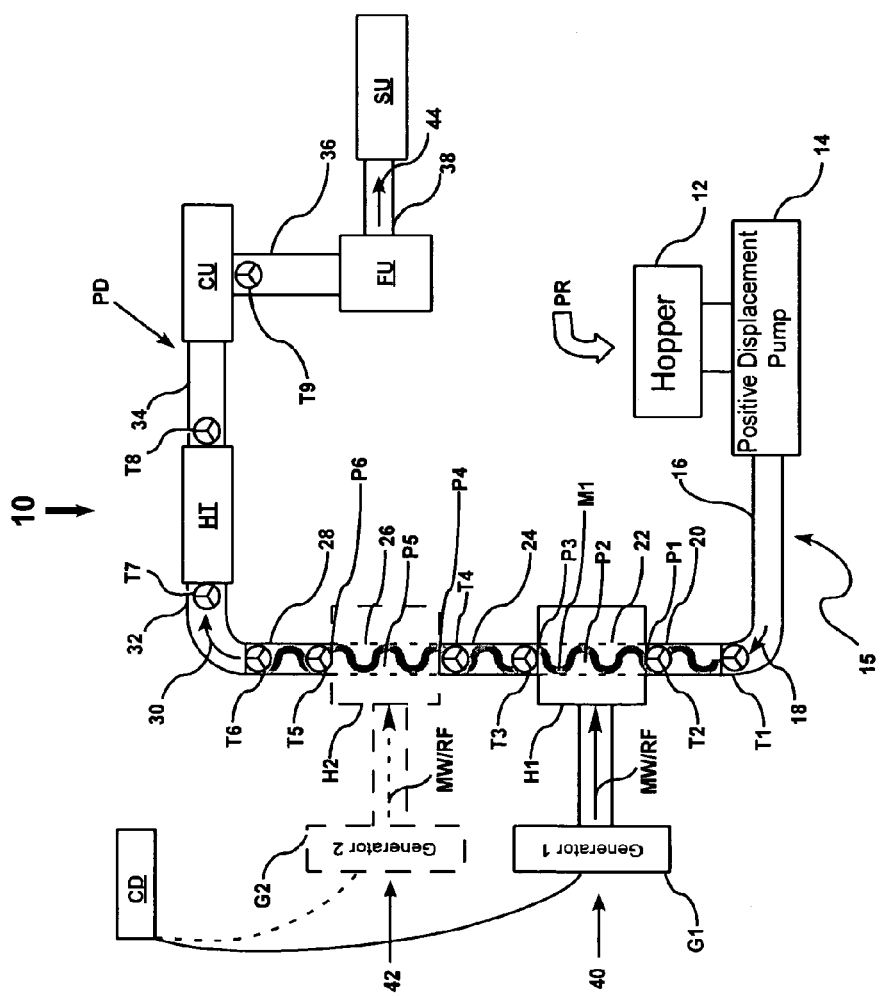
FIGS. 9 and 10 are schematic views depicting aspects of representative embodiments of the presently disclosed apparatuses used to thermally treat biomaterials.
Figure 10:
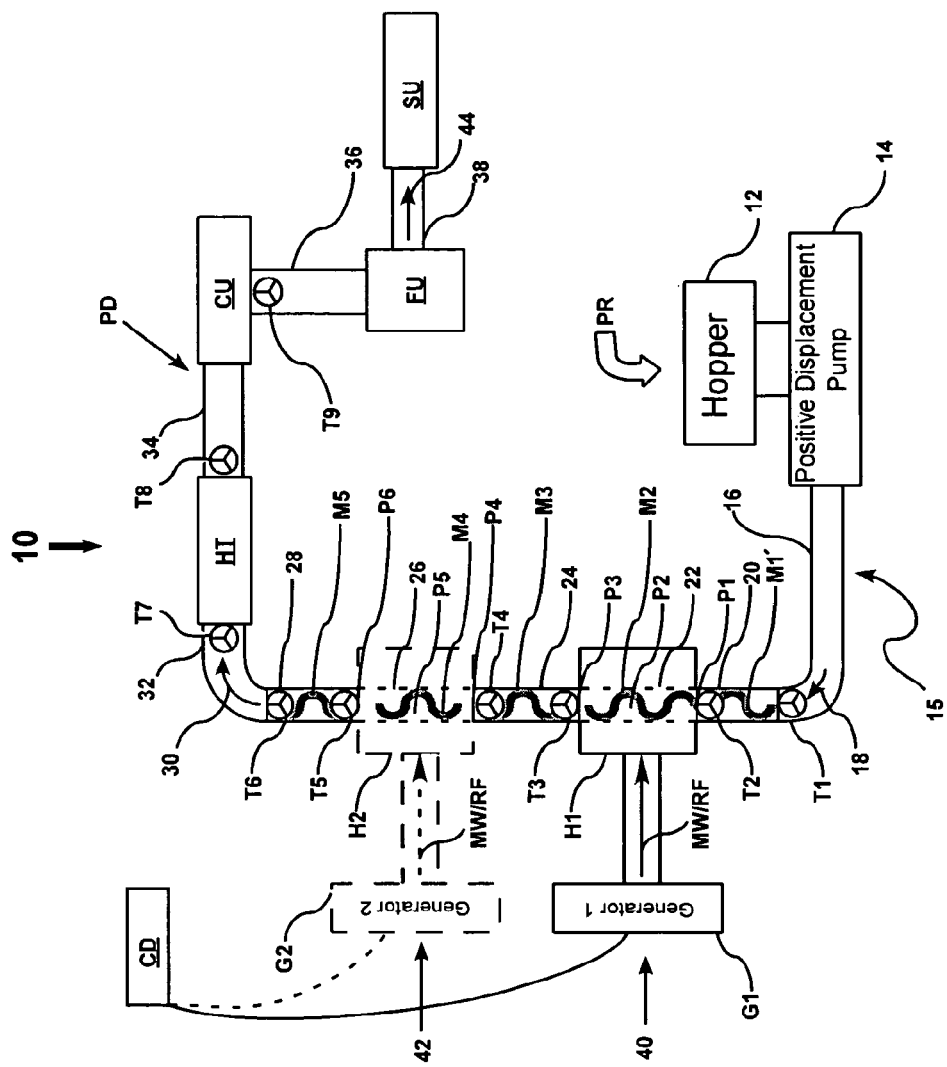

Referring now to the Figures, where like reference numerals refer to like parts throughout, an apparatus for thermally treating a flowable material is generally referred to as 10. Referring now to FIGS. 1, 9 and 10, apparatus 10 comprises hopper 12, into which a biomaterial preparation PR is loaded. Hopper 12 is in flow (or fluid) communication with pump 14, and pump 14 is controlled to provide a flow of biomaterial preparation PR through apparatus 10. The direction of flow in FIGS. 1, 9 and 10 is indicated by arrows 18, 30, and 44.

Continuing with FIGS. 1, 9 and 10, apparatus 10 can comprise a conduit 15 for receiving a flowable material, such as preparation PR. Conduit 15 comprises a series of conduit sections 16, 20, 22, 24, 26, 28, 32, 34, 36, and 38. Conduit sections 22 and 26 are transparent to electromagnetic radiation e.g., MW and/or RF radiation). Apparatus 10 also includes one or more of temperature sensors T1, T2, T3, T4, T5, T6, T7, T8, and T9, which are used to monitor temperatures throughout apparatus 10, as described herein below.

Continuing with FIGS. 1, 9 and 10, apparatus 10 comprises device 40 and 42 for providing electromagnetic radiation to at least a portion of conduit 15. Devices 38 and 40 comprise generators G1 and G2, respectively, and heaters H1 and H2, respectively, and provide any desired form of electromagnetic radiation, such as but not limited to microwave (MW) radiation and radio frequency (RF) radiation. Device 42 is show in dashed lines in that it is optionally included in apparatus 10 as shown in FIGS. 9 and 10. Devices 40 and 42 are positioned to provide electromagnetic radiation to conduit sections 22 and 26, as show by arrows MW/RF (arrow shown in dashed lines for device 42).

Continuing with FIG. 9, a mixing structure M1 is disposed within or along conduit sections 20, 22, 24, 26, and 28 to provide for thermal equalization in at least a portion of the flowable preparation PR. Referring particularly to FIG. 10, apparatus 10 comprises mixing structures M1', M2, M3, M4, and M5 at a locations including but not limited to one or more points of entry (e.g., P1, P4), one or more points within (P2, P5), one or more exits (P3, P6), and combinations thereof, of sections 22 and 26 of conduit 15 that is transparent to electromagnetic radiation.

In some embodiments, mixing structures M1, M1', M2, M3, M4, and M5 can comprise an altered cross-sectional geometry of conduit sections. In some embodiments mixing structures M1, M1', M2, M3, M4, and M5 can comprise one or more passive mixing structures, one or more active mixing structures, or both. Indeed, in some embodiments, mixing structures M1, M1', M2, M3, M4, and M5 can comprise any combination of passive, active, or both passive and active mixing structures which serve to increase physical contact and heat exchange between regions of preparation PR having a higher temperature level and regions of preparation PR with a lower temperature level, which would not occur in the absence of the mixing structures. In some embodiments, mixing structures M1, M1', M2, M3, M4, and M5 can provide at least a 10% reduction in temperature distribution variability (standard deviation) across flowable preparation PR when compared to temperature distribution variability (standard deviation) across flowable preparation PR in the absence of the mixing structures.

Referring again to FIGS. 1, 9 and 10, apparatus 10 can comprise a control device CD. Control device CD can control flow through conduit 15. The flow rate can be a constant flow rate, for example, a volumetric flow rate of at least 0.25 gallons per minute. Control device CD can control a power level of devices 40 and/or 42 for providing electromagnetic radiation. For example, the power level can be controlled such that heating of a flowable material in the conduit can occur at an average bulk temperature increase rate in the flowable material of at least 1 degree Fahrenheit per second or 0.5 degrees Celsius per second. Control device CD can control a power level of devices 40 and/or 42 for providing electromagnetic radiation such that heating of preparation PR in conduit 15 occurs at a higher rate than heating of conduit 15, such the heating of preparation PR is substantially free of heating by contacting preparation PR with a surface of conduit 15 having a temperature that exceeds a maximum temperature level of flowable preparation PR itself. Control device CD can control a power level of devices 40 and/or 42 such that the power level can be maintained constant. Control device CD can control a power level of devices 40 and/or 42 such that the power level can be preset automatically or manually adjusted to a level predetermined to provide a predetermined thermal treatment of the flowable biomaterial at a predetermined mass flow rate. These variables can be predetermined by one of ordinary skill in the art after a review of the present disclosure, depending of the biomaterial of interest.

Figure 15:
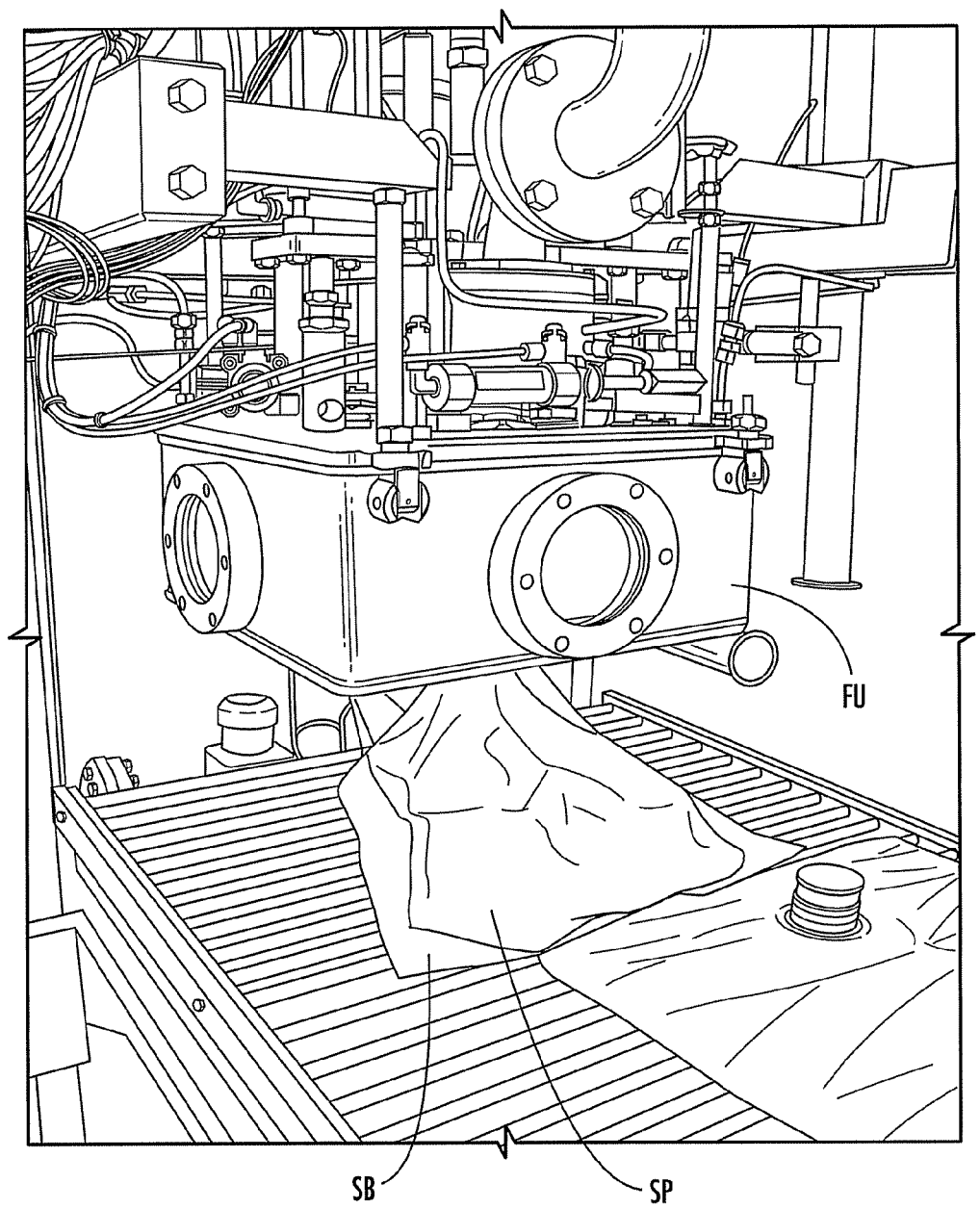
FIG. 15 is a drawing showing the filling of the sterilized product under aseptic fill conditions into a previously sterilized bag. The product was subsequently proven to be shelf stable and viable microbe-free after a 4-month storage under ambient temperature storage conditions.
Figure 16:
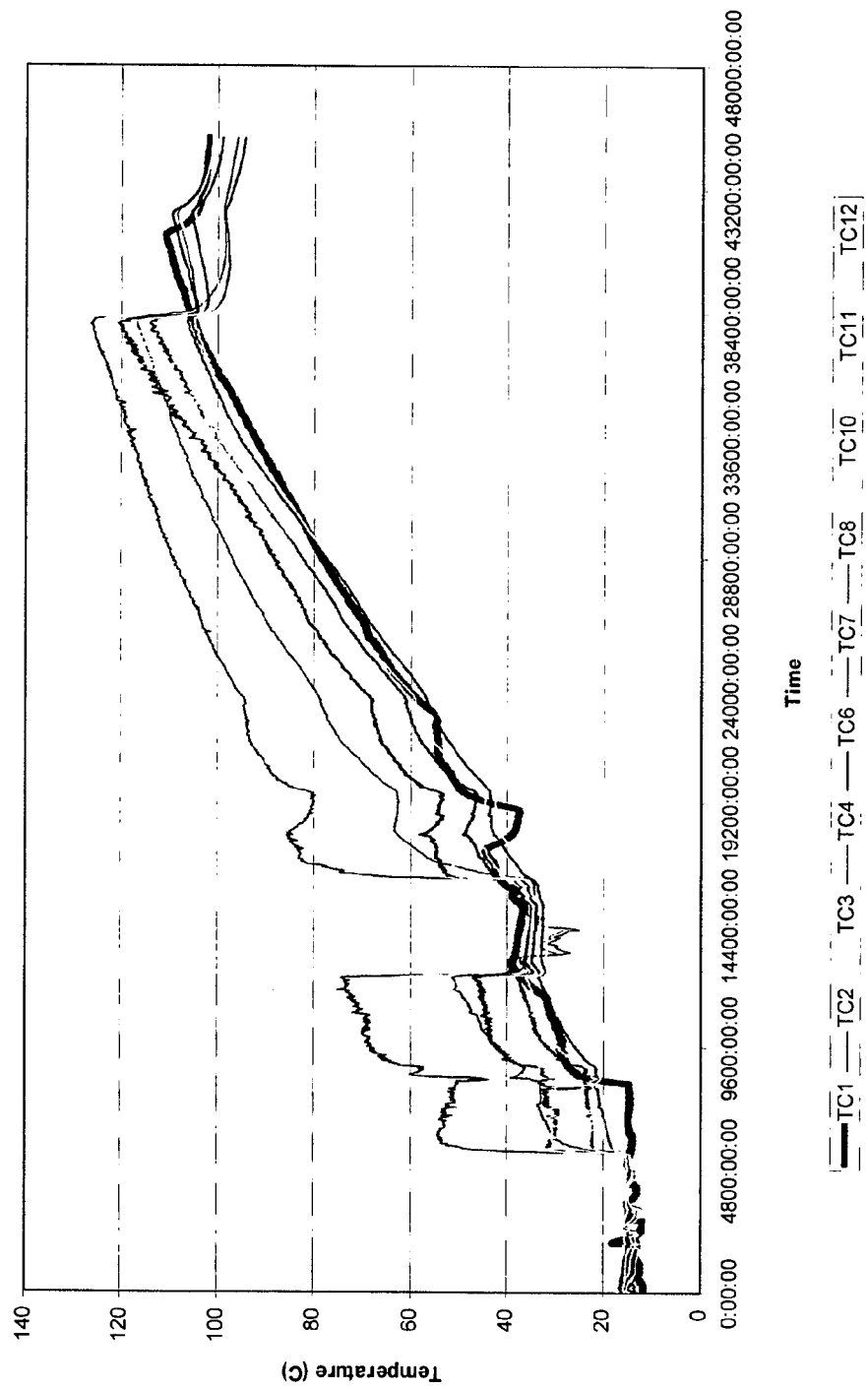
FIG. 16 is a graph of the temperature measurements acquired during a recirculated, incremental heating run of an extremely viscous, poorly thermally conductive vegetable homogenate: sweetpotato puree.

Continuing with reference to FIGS. 1, 9 and 10, apparatus 10 can comprise a packaging device PD for one of packaging flowable preparation PR for refrigerated storage, aseptically packaging flowable preparation PR, and both packaging flowable preparation PR for refrigerated storage and aseptically packaging flowable preparation PR By way of example, packaging device of apparatus 10 can comprise a hold tube HT adapted for flow (or fluid) communication with conduit 15, such as by conduit section 32; a cooling unit CU adapted for flow (or fluid) communication with hold tube HT, such as by conduit section 34; filling unit FU adapted for flow (or fluid) communication with cooling unit CU, such as by conduit section 36; and storage unit SU adapted for flow (or fluid) communication with cooling unit CU, such as by conduit section 38. Optionally, storage unit SU is a refrigerated storage unit. Optionally, surfaces of hold tube HT, cooling unit CU, filling unit FU, and storage unit SU that will contact preparation PR are rendered commercially sterile prior to the introduction of flowable preparation PR. Control device CD can provide appropriate control signals for packaging device PD and components thereof. FIG. 15 is a drawing showing the filling of sterile bag SB with a sweet potato preparation SP, via a filling unit FU.

Figure 13C:
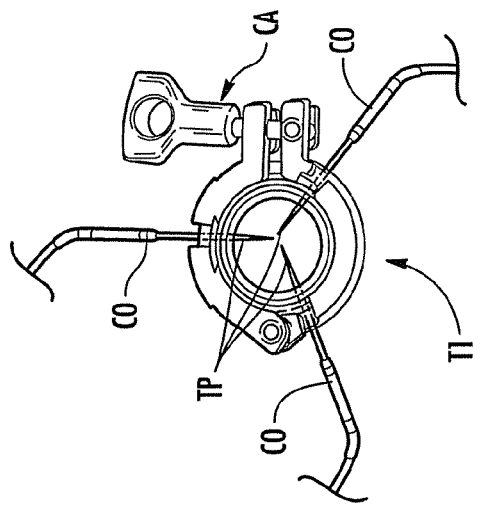
FIGS. 13A-13C area drawings of a tool for measurement and monitoring of cross-sectional temperature distributions. The tool is a combination of single or several multi-point thermocouple probes providing cross-sectional coverage of the area perpendicular to the direction of material flow. Positioning and utilizing such sensing and monitoring tools at key locations (heater entry and exit and mixing element entry and exit) has been used to test and document the uniformity and/or its absence and illustrate the efficiency of a variety of mixing implements and tools in achieving temperature equalization.
Figure 13B:
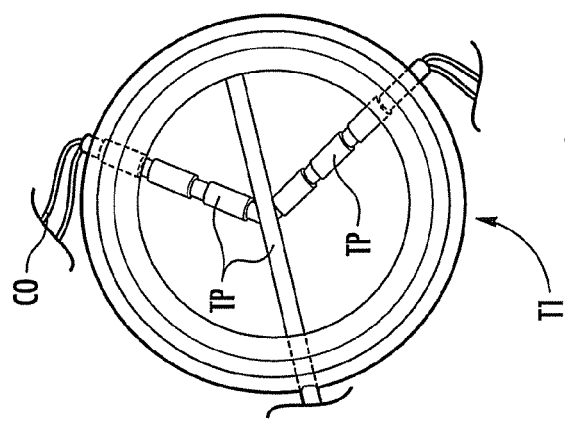
Figure 13A:
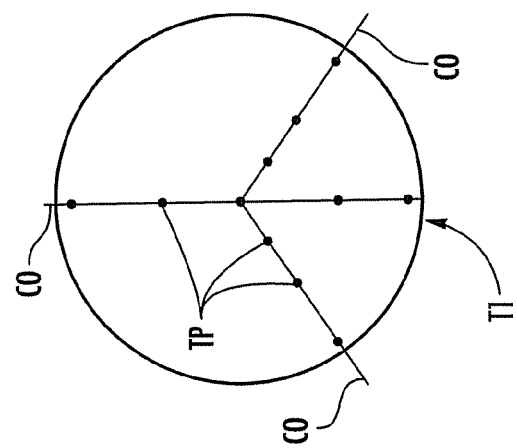

Referring now to FIGS. 13A-13C, a temperature sensor T1 is disclosed. Temperature sensor T1 is used for measurement and monitoring of cross-sectional temperature distributions. Temperature sensor T1 can comprise combination of single or several multi-point thermocouple probes TP providing cross-sectional coverage of the area perpendicular to the direction of material flow (see FIGS. 9 and 10). Temperature probes TP are operatively connected to couplers CO, which are then in communication with control device CD (see FIGS. 9 and 10). In the embodiment shown in FIG. 13C, temperature sensor T1 further comprises a clamp assembly CA that can be used to facilitate mounting of temperature sensor T1. Positioning and utilizing such sensing and monitoring tools at key locations (heater entry and exit and mixing element entry and exit) has been used to test and document the uniformity and/or its absence and illustrate the efficiency of a variety of mixing implements and tools in achieving temperature equalization in accordance with the presently disclosed subject matter.

Figure 14A:
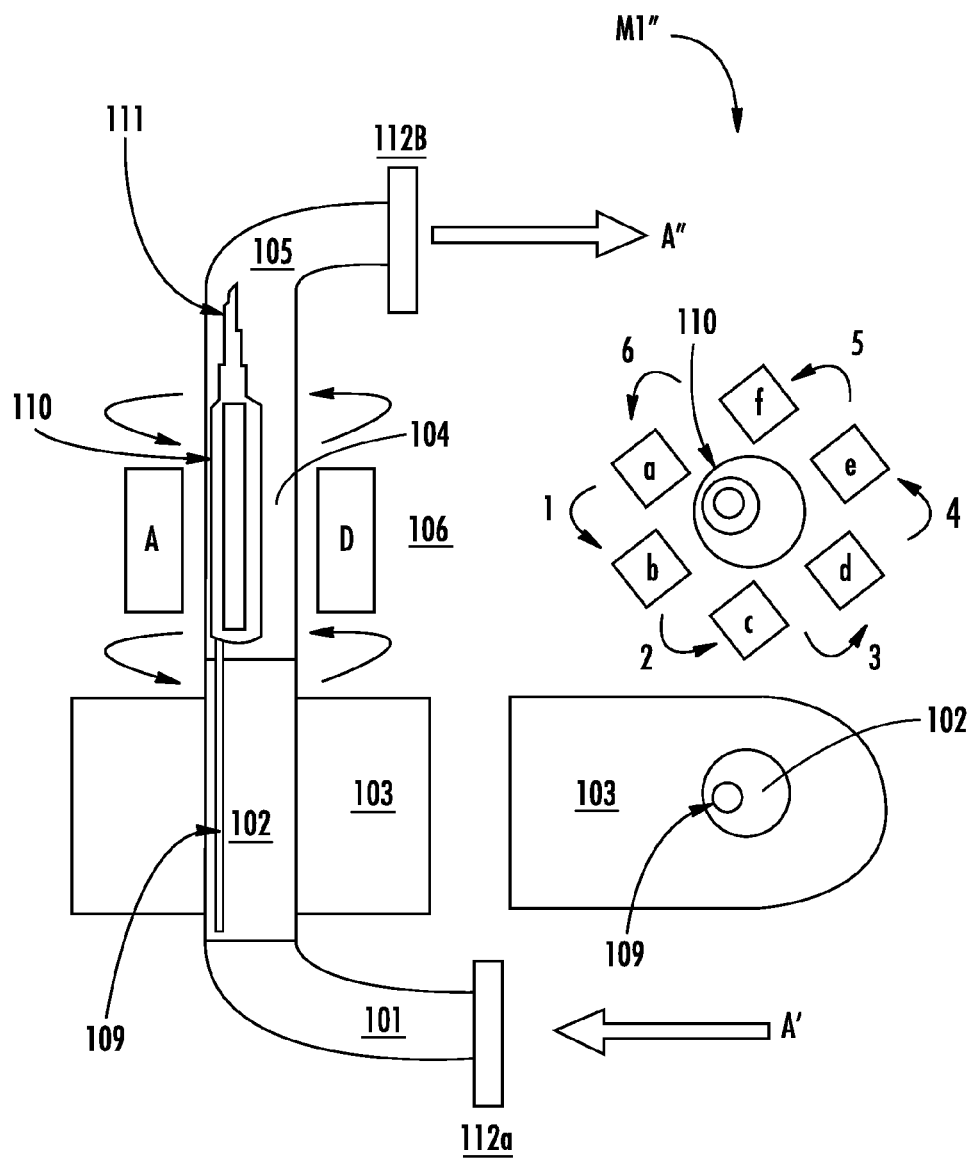
FIGS. 14A and 14B are schematic diagrams of an exemplary mixing device, with a capability to provide the mechanical mixing effect in all previously listed target locations (preceding, concurrent and/or subsequent to heating) at the same time and using the same device—this can be achieved by extending the mixing element throughout these regions. The mixing element is fabricated from a MW or RF-transparent material and provides a concurrently rotating and orbiting movement within the exposure region, ensuring that no configuration is static and minimizing the likelihood of overheating and/or runaway heating within the transparent tube or chamber.
Figure 14B:
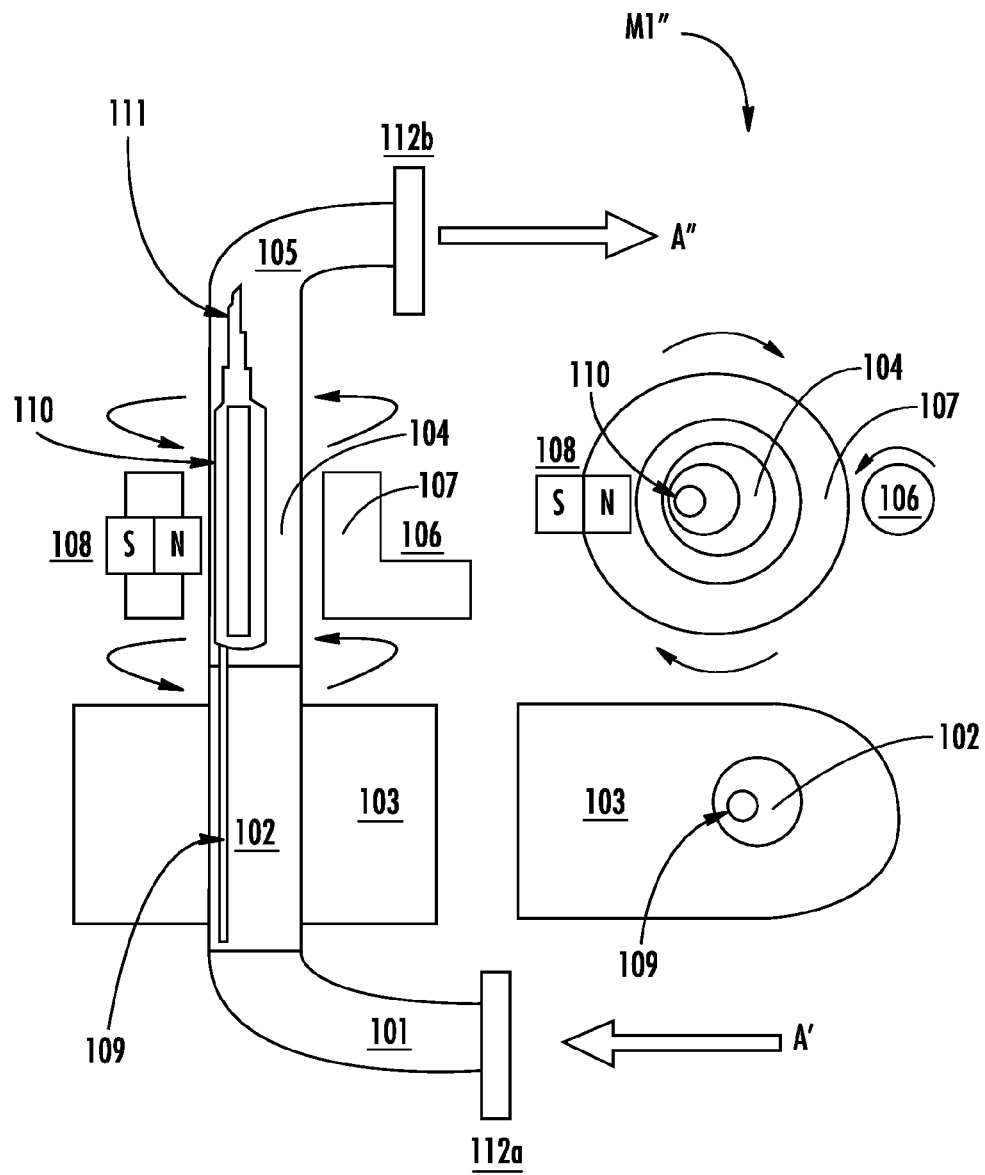

FIGS. 14A and 14B are schematic diagrams of an exemplary mixing device, referred to as M1". Mixing device M1" can provide mechanical mixing effects in all previously listed target locations (preceding, concurrent and/or subsequent to heating, see FIGS. 9 and 10) at the same time and using the same device. M1" comprises a mixing element, and mechanical mixing effects can be achieved by extending the mixing element throughout these regions. The mixing element is fabricated from a MW or RF-transparent material and provides a concurrently rotating and orbiting movement within the exposure region, ensuring that no configuration is static and minimizing the likelihood of overheating and/or runaway heating within the transparent tube or chamber.

With reference first to FIG. 14A, the material to be heated A' enters the heating segment through a stainless steel elbow-shaped tube 101, continues through a microwave transparent tube segment 102 where it undergoes heating delivered by microwaves using either a focusing structure of a microwave applicator or a simpler microwave exposure region design 103, and mixing with a single or multiple microwave-transparent polymer (such as but not limited to TEFLON®, polyether ether ketone (PEEK), polysulfone, TPX® polymethylpentene (PMP), polycarbonate, or ULTEM® polyetherimide) mixing elements 109. Material A' exits the microwave exposure region and enters first the straight stainless steel tube segment 104 containing the cylindrical ferromagnetic mixer core 110 encased either in stainless steel or TEFLON®. The single or multiple mixing element(s) 109 are attached to the bottom of the ferromagnetic core at the edge of its cylindrical perimeter. A stainless steel spacer element 111 is attached to the top of the cylindrical ferromagnetic core and maintains the vertical position of the cylindrical core and the element taking advantage of the upwardly moving push of the incoming material and the centrifugal pulling force of one of the four to eight externally radially-positioned electromagnets a-d. Electromagnets a-d are switched on one at a time and the power is cycled (steps 1-6 are repeated continuously). Power and control can be provided in any suitable manner, such as but not limited to through a control device CD, as shown in FIGS. 9 and 10. This results in a radial and rotational movement of ferromagnetic mixer core 110 and a rotating as well as orbiting movement of single or multiple mixer element(s) 109. This provides the mixing action within the microwave exposure region without obstructing the focused microwave energy distribution for any length of time at any individual point along its path: the radial position of the mixing element(s) as well as their position along the internal perimeter of the straight stainless steel tube portion of the flow path constantly change. The rate of the change of this position and therefore the rate of mixing action can be controlled by increasing or decreasing the speed of electromagnet switching steps 1 through 6. Cylindrical ferromagnetic mixer core 110 as well as stainless steel spacer element 111 provide additional mixing for the flowing material which finally enters an elbow stainless steel tube element 105 and exits the heating/mixing process segment A". Optionally, single or multiple temperature monitoring fixtures (e.g. temperature sensors T1 et seq. as disclosed herein) can be used at the heater/mixer entry 112a and the exit 112b locations to monitor and confirm the achieved temperature increases and distributions.

Turning now to FIG. 14B, material to be heated A' enters the heating segment through stainless steel elbow-shaped tube 101, continues through microwave transparent tube segment 102 where it undergoes heating delivered by microwaves using either a focusing structure of a microwave applicator or a simpler microwave exposure region design 103, and mixing with a single or multiple microwave-transparent polymer (including but not limited to TEFLON®, polyether ether ketone (PEEK), polysulfone, TPX® polymethylpentene (PMP) or ULTEM® polyetherimide) mixing elements 109. The material exits the microwave exposure region and enters first the straight stainless steel tube segment 104 containing the cylindrical ferromagnetic mixer core 110 encased either in stainless steel or TEFLON®: the single or multiple mixing element(s) 109 are attached to the bottom of the ferromagnetic core at the edge of its cylindrical perimeter. A stainless steel spacer element 111 is attached to the top of the cylindrical ferromagnetic core and maintains the vertical position of the cylindrical core and the element taking advantage of the upwardly moving push of the incoming material and the centrifugal pulling force of the externally positioned strong permanent magnet 108. Strong permanent magnet 108 is affixed to a perimeter of a donut-shaped stage 107 which is driven to rotate around the stainless steel tube through a sprocket, belt or clutch-friction type interface with an electromotor-driven rotating element 106. The orbiting motion of permanent magnet 108 results in a radial and rotational movement of ferromagnetic mixer core 110 and a rotating as well as orbiting movement of mixer element(s) 109. This provides the mixing action within the microwave exposure region without obstructing the focused microwave energy distribution for any length of time at any individual point along its path: the radial position of the mixing element(s) as well as their position along the internal perimeter of the straight stainless steel tube portion of the flow path constantly change. The rate of the change of this position and therefore the rate of mixing action can be controlled by increasing or decreasing the speed of electromagnet switching steps 1 through 6. Cylindrical ferromagnetic mixer core 110 as well as stainless steel spacer element 111 provide additional mixing for the flowing material which finally enters elbow stainless steel tube element 105 and exits the heating/mixing process segment A". Optionally, single or multiple temperature monitoring fixtures can be used at heater/mixer entry 112a and exit 112b locations to monitor and confirm the achieved temperature increases and distributions.

III.B. Microwave and/or Radio Frequency Transparent Tubes

The presently disclosed subject matter can employ a composite integrated design for a microwave transparent composite tube and a sanitary fitting that addresses heretofore known causes of flow-through tube failures during microwave thermal processing of foods, beverages, chemicals and biomaterials.

The advent of new microwave (MW) and other non-contact heating (for example, radio frequency (RF)) technologies has created a need for flow-through devices and assemblies that could be used in these systems under conditions of relatively high temperature and pressure, very high energy density and throughput per unit area; high chemical and physical stresses ranging from chemically aggressive processed material components to physical stresses of high pressure, expansion, torsion and vibration and impact.

The characteristics of a flow-through device or cavity to be used for the continuous flow thermal treatment of foods, beverages, chemicals, and other biomaterials can be numerous and highly specific. They can be categorized into the following desirable characteristics:
1. Extremely high microwave transparency (very low value of dielectric loss factor and tangent) under commonly occurring operational conditions
2. Capability to withstand sterilization level temperatures without degradation or property change
3. Capability to withstand sterilization level pressures without degradation or property change
4. Capability to withstand sterilization level temperatures at sterilization level pressures without degradation or property change
5. Capability to withstand chemically aggressive components of processed materials without degradation or property change
6. Capability to withstand dimensional, expansional, thermal, vibrational and impact stresses regularly encountered during the process without degradation or property change
7. Compliance with FDA, USDA and pharmaceutical regulations for food or other biomaterial—contact surface
8. Compliance with 3A design requirements for in-place cleaning and sanitation Additional characteristics that can appear in some embodiments include the following:
1. Visible light transparency or translucency—to identify imperfections in material that could later lead to depositions and/or failures—also to identify undesired boiling/flashing of the processed material during the actual process and post-process identification of deposits or defects caused during the run.
2. High gloss, smooth and slick, non-stick, pinhole-free material contact surface
3. Capability for quick and easy insertion and removal from the microwave or RF focusing structure (radiator/concentrator/reactor/heater)
4. Capability for integration into existing food, beverage, chemical, and biomaterial processing lines (typically by using standard aseptic interfacing components and standards, such as tri-clamp or other sanitary types of fittings)

The lack of readily and commercially available devices that would appropriately address some or all of these issues and considerations has evolved into one the major hurdles in implementing advanced microwave and RF technologies for continuous thermal processing of foods, beverages, chemicals, and other biomaterials.

Previously, four types of assemblies/tubes were considered:

Type 1: Composite (three-piece) TEFLON® tubes consisting of semi-transparent linear, extrusion-drawn TEFLON® tube piece fitted at each end with a stainless steel crimp-on collar fitting/sanitary interface (Tri-clamp). These assemblies have been typically used as tank liquid-level view-ports for chemically aggressive or high-temperature contents. The assemblies were obtained commercially and subsequently tested in our labs and pilot plants.

Type 2: Composite (three-piece) glass or ceramic tubes consisting of a smooth-bore ceramic or glass tube fitted at each end with a stainless steel screw-on or glue-on collar fitting/sanitary interface (Tri-clamp). These assemblies have been specifically fabricated according to microwave fabricator's orders and specifications and subsequently tested in our pilot plants.

Type 3: Single piece glass or ceramic tubes consisting of a smooth-bore ceramic or glass tube with machined or molded end fittings comprising sanitary interfaces (Tri-clamp). These assemblies have been specifically fabricated per microwave fabricator's orders and specifications but have not been available for testing.

Type 4: Single piece tubes consisting of a machined smooth-surface advanced plastic tube with machined or molded end fittings comprising sanitary interfaces (tri-clamp). These assemblies have been specifically fabricated in the North Carolina State University Instrument Shop according to chosen specifications and have been thoroughly tested. Fabrication materials included Ultem 1000 (polyetherimide), polysulphone, polymethylpentene (TPX), and PEEK (polyetheretherketone), or other suitable microwave-transparent polymers.

The following desirable characteristics were identified for each of the four considered designs—failure modes are also indicated for each type to further illustrate the need for an appropriate alternative solution provided by the current invention:

Type 1: Smooth, non-stick surface
MW transparency
FDA, USDA, Pharma-compliant
Readily available on open market
Temperature resistance
Resistance to most aggressive chemicals
    Typical failure mode: pressure deformation at operating temperatures Type 2: Smooth, non-stick surface
MW transparency
FDA, USDA, Pharma-compliant
Temperature and pressure resistance
Resistance to most aggressive chemicals
    Typical failure modes: thermal stress fractures at interface of steel and ceramic due to different thermal expansion rates, impact fractures, and adhesive breakdown Type 3: Smooth, non-stick surface
FDA, USDA, Pharma-compliant
Temperature and pressure resistance
Resistance to most aggressive chemicals
    Anticipated failure modes: thermal stress fractures, impact fractures Type 4: Temperature and pressure resistance
Inexpensive, one piece design
FDA, USDA, Pharma-compliant
    Typical failure modes: material deposits due to non-smooth surface, localized overheating at deposit locations, stress fractures at weak interfaces (clamp fittings)

Referring now to FIGS. 11A-11E, a set of schematic views of tubes are presented. Representative materials are generally shown through the use of shading, which can be summarized as follows: solid shading, crimp-on stainless steel sanitary fitting; gray shading, PTFE/extruded PTFE; tight horizontal and vertical cross-hatching, Ultem, polysulphone, or PEEK sleeve; diagonal cross-hatching, MW-transparent high grade (alumia) ceramic; wide horizontal lines, machined PTFE semi-cylinders; close horizontal lines, multiple layers of thick PTFE film.

Figures 11A, 11B, 11C, 11D, 11E:
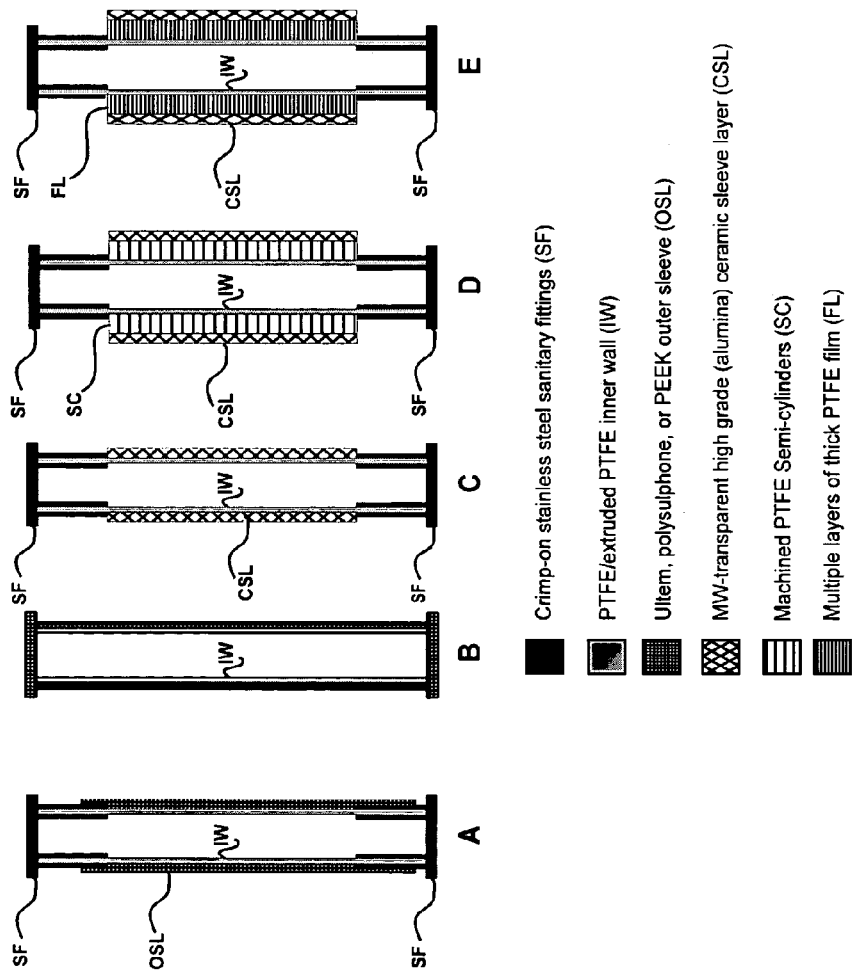
FIGS. 11A-11I are schematic view of examples of microwave and RF-transparent flow-through tubes/chambers and methods for preparing the same.
Figure 11F:
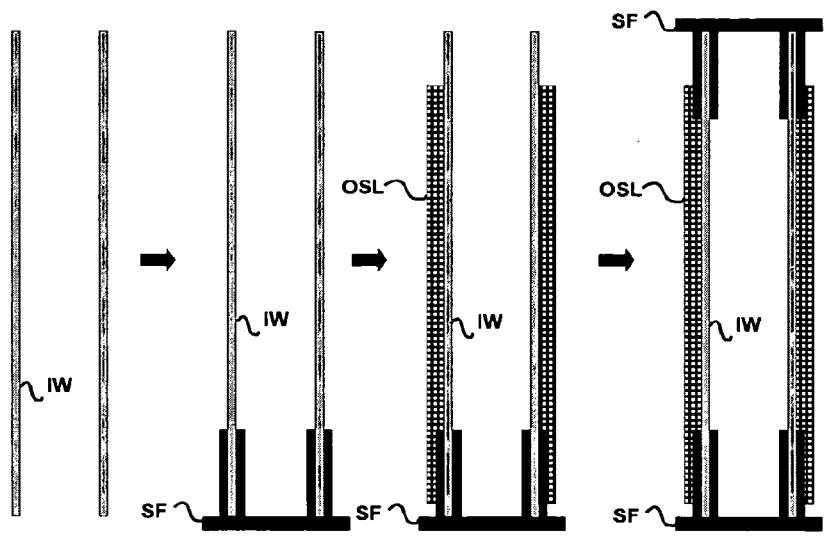

Referring now to FIGS. 11A and 11F, in some embodiments a tube in accordance with the presently disclosed subject matter comprises a constricting cylindrical sleeve OSL fabricated from temperature and pressure resistant materials from Type 4 tube assemblies (polyetherimide/Ultem, polysulphone, polymethylpentene (TPX), or PEEK) overlaid over the pressure-susceptible TEFLON® (or other smooth-surface compliant and microwave transparent material) tube segment inner wall IW of assembly Type 1. This design yields a smooth product-contact surface—TEFLON®, thereby reducing the occurrence of product deposition failure, a multi-fold increase in pressure resistance characteristics (Ultem, polysulphone, polymethylpentene (TPX) or PEEK) and a high resistance to stress fracture failures at sanitary interface points SF (clamp fittings made of stainless steel). This would result in a four-piece tube assembly (TEFLON® inner wall IW; Ultem, polysulphone, polymethylpentene (TPX), or PEEK sleeve and two crimp-on stainless steel sanitary clamp fittings SF).

Referring now FIG. 11B, in some embodiments a tube in accordance with the presently disclosed subject matter comprises a single-piece machined tube fabricated from one of the advanced polymers used in the production of Type 4 tube assemblies (Ultem, polysulphone, polymethylpentene (TPX), or PEEK) with the internal bore surface 1W coated with TEFLON® (or other smooth-surface compliant and microwave transparent material) to provide the smooth product contact surface. Such assembly could remain somewhat susceptible to stress fractures at sanitary clamp interfaces, but this is manageable with appropriate monitoring.

In addition to these representative embodiments, numerous derivative designs can be assembled, for example, involving additional microwave and/or radio frequency transparent (MWRFT) layers or sleeves, alternative materials for crimped sanitary fittings, and combinations of machined, extruded, and crimped components.

Disclosed herein are representative MWRFT tube assemblies with a smooth product-contact surface, thereby reducing the occurrence of product deposition failures, a multi-fold increase in pressure and physical resistance characteristics a high resistance to stress fracture failures at sanitary interface points (clamp fittings made of stainless steel). The representative tubes address the high incidence of MWRFT flow-through tube assembly failure. A high incidence of these failures is one of the hurdles to a wider application of continuous-flow microwave heating/sterilization technologies.

Figure 11G:
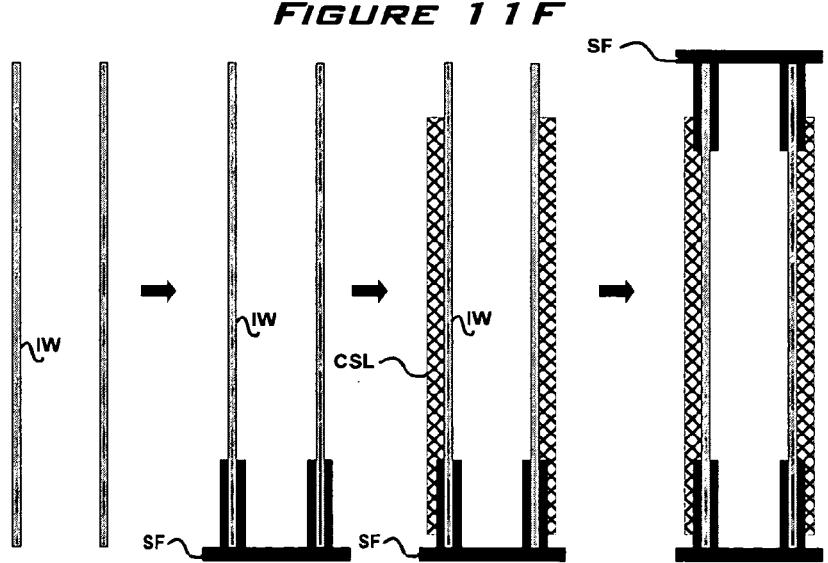

Referring now to FIGS. 11C and 11G, in some embodiments, the MWRFT composite tubes employ a high-grade alumina ceramic sleeve CSL as the external MWRFT layer, instead of a MWRFT high-grade polymer. This layer can also provide pressure protection to the internal extruded TEFLON® tube layer 1W. FIGS. 11C and 11G illustrate the components of a representative embodiment and an exemplary assembly sequence for the same, including clamp fittings SF, which optionally comprise stainless steel.

An embodiment of the MWRFT composite tube of FIGS. 11C and 11G has been constructed and experimentally tested under semi-industrial production conditions (60 KW heater unit, 1-2 gal/min flow rate with temperature increases ranging from 100 to 140° C.). This embodiment performed far better than any other previously tested tube assembly. In one instance, the tube was used for 14 consecutive runs yielding a total of greater than 50 hours of intermittent run time.

In previous testing, other tube assemblies often failed after one or two uses. Furthermore, the tube failure modes experienced with the assembly according to FIGS. 11C and 11G were never catastrophic: i.e., these tubes never breached during a processing run and no process materials escaped from the processing system (as opposed to certain previous assemblies where leaks were frequently caused by a variety of cracks, holes, and tears caused by pressure, temperature, and deposit formation and/or overheating).

However, even the tube assemblies of FIG. 11C eventually failed after a period of use. Thus, monitoring of the period of use is advisable. Tube failure can be caused by particle-containing suspensions of processed materials, subsequent internal tube wall deposits, overheating, and localized fouling of the internal tube surface(s) and resulting flavor and/or color defects in the processed material. The deposit formed on the internal surface of the flow-through tube. If the deposit is severe enough and has been subjected to extended overheating, the tube surface can be permanently damaged rendering the tube assembly unusable. In some instances, only one component of the assembly (the internal extruded TEFLON® tube IW) failed, but the entire assembly often needs to be discarded. Occasionally, external layer CSL of high-grade ceramic alumina can be reused, but the cost of the re-assembly with the new elements can be significant.

Tube failure can also be caused by cold shock upon heater turn-off. In this case, the failure occurs when upon completion of the heating run while both internal and external tube layers are heated up to and above 130-140° C., power to the MW heater is switched off but the process pump continues to pump the cold product through the tubing, causing the cold shock and cracking of the external layer of the tube assembly at the top/hot end. Even when only one of the components fails (e.g., the external ceramic tube), the whole assembly typically needs to be discarded due to the procedure used in the assembly.

Figure 11H:
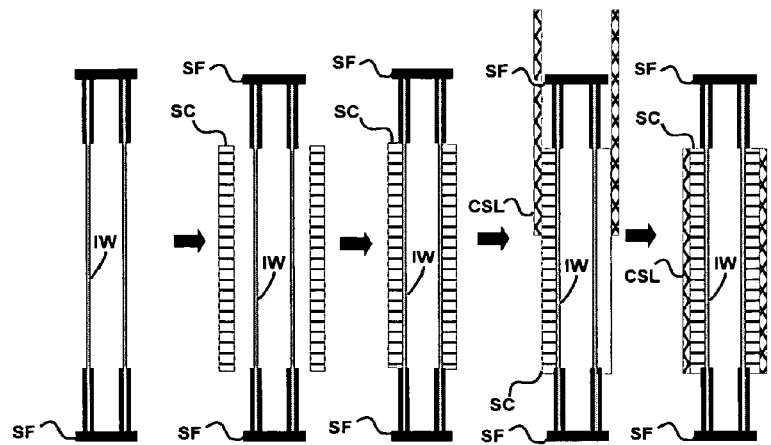

Therefore two additional objectives for constructing embodiments of the tube assembly are as follows:
1. Modify the assembly sequence and process in order to simplify the removal and replacement of one of the failed components as well as re-assembly of the tube including the new replacement element(s)
2. Thermally insulate the external ceramic tube layer in order to protect it from overheating as well as the sudden cooling caused by the power turn-off and the resulting immediate contact with the process material at low temperatures Both of these objectives have been met by the embodiments of the presently disclosed subject matter depicted in FIGS. 11D and 11H, and FIGS. 11E and 11I. As shown in FIGS. 11D and 11H, a pre-fabricated, commercially available three-piece extruded TEFLON® sight-port 1W was covered with a precision-machined TEFLON® tube SC cut longitudinally along the length into two identical semi-cylindrical pieces. The two halves were pressed against the internal tube IW of TEFLON® as an external layer of high-grade ceramic tubing CSL was pulled over the stainless steel clamps SF and around the two tube halves SC comprising machined TEFLON®. This ensured appropriate pressure and temperature protection for the internal TEFLON® tube IW, thermal protection to the external ceramic layer CSL as well as ease of assembly, disassembly, and parts replacement for repeated use of undamaged components.

Figure 11I:
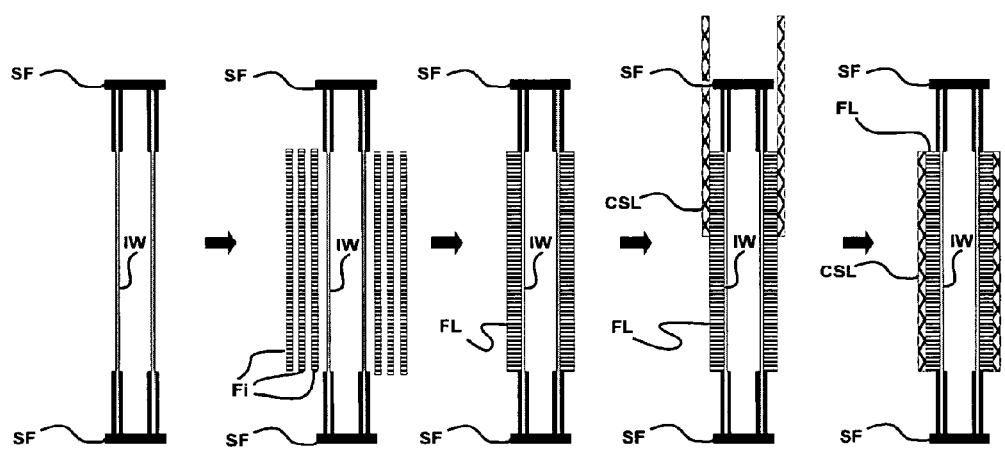

FIGS. 11E and 11I illustrate another embodiment of the tube assembly. A pre-fabricated, commercially available three-piece extruded TEFLON® sight-port 1W is covered by winding a thick TEFLON® film FL around its external perimeter until the external diameter of the tube and multiple film layers reaches a thickness close to the external diameter of stainless steel clamps SF. The wound layers of thick TEFLON® film FL are held pressed against the internal tube IW of TEFLON® as an external layer of high-grade ceramic tubing CSL is pulled over stainless steel clamps SF and around the multiple layers of TEFLON® film FL. This also ensures appropriate pressure and temperature protection for the internal TEFLON® tube IW, thermal protection to the external ceramic layer as well as ease of assembly, disassembly and parts replacement for repeated use of undamaged components.

In addition to the embodiments specifically described hereinabove, numerous derivative designs can be assembled, for example, involving additional MWRFT layers or sleeves, alternative materials for crimped sanitary fittings, and combinations of machined, extruded, and crimped components.

Summarily, disclosed herein is a MWRFT tube assembly with a smooth product-contact surface, thereby reducing the occurrence of product deposition failures, a multi-fold increase in pressure and physical resistance characteristics, and a high resistance to stress fracture failures at sanitary interface points (clamp fittings made of stainless steel). The disclosed tubes address the high incidence of MWRFT flow-through tube assembly failures due to a variety of factors. A high incidence of these failures is one of the hurdles to a wider application of continuous-flow microwave heating/sterilization technologies.

EXAMPLES

The following Examples have been included to illustrate modes of the presently disclosed subject matter. Certain aspects of the following Examples are described in terms of techniques and procedures found or contemplated by the present co-inventors to work well in the practice of the presently disclosed subject matter. These Examples illustrate standard practices of the co-inventors. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Preparation of Sweetpotato Puree (SPP)

Beauregard cultivar sweetpotatoes were prepared in the Fruit and Vegetable Pilot Plant, Department of Food Science, North Carolina State University (Raleigh, N.C., United States of America), for testing in a 5 kW microwave unit, color, and rheological analyses, and measurement of dielectric properties. The roots were cured at 30° C. at 85-90% relative humidity for seven days stored at 13-16° C. and 80-90% relative humidity, and the puree was prepared as previously described (Truong et al. 1994). Roots were washed, lye-peeled in boiling solution (104° C.) of 5.5% NaOH for 4 minutes, and thoroughly washed in a rotary-reel sprayed washer to remove separated tissue and lye residue. Peeled roots were hand-trimmed and cut into approximately 0.95 cm thick slices using a commercial slicer (Louis Allis Co. Slicer, Milwaukee, Wis., United States of America). The slices were steam-cooked for 20 minutes in a thermoscrew cooker (Rietz Manufacturing Co., Santa Rosa, Calif., United States of America) and comminuted in a hammer mill (Model D, Fitzpatrick Co., Chicago, Ill., United States of America) fitted with a 0.15 cm screen. The puree was filled into polyethylene bags, frozen and stored at −20° C. until used.

For test runs in a 60 kW microwave unit, frozen sweetpotato puree from Beauregard cultivar was purchased from Bright Harvest Sweetpotato Company, Inc. (Clarksville, Ark., United States of America). All of the puree samples used in the Examples had moisture contents of 80-82%.

Example 2

Measurement of Dielectric Properties

An open coaxial dielectric probe (HP 85070B; Agilent Technologies, Palo Alto, Calif., United States of America) was used with an automated network analyzer (HP 8753C; Agilent Technologies) to measure the dielectric properties of the SPP samples. The dielectric properties were measured in the 300 to 3000 MHz frequency range, with 541 intermediate frequencies. The system was calibrated using the calibration sequence following the instruction manual provided by the manufacturer (Agilent 1998). The samples (<100 g) were heated in a water bath (Model RTE111, Neslab Instruments Inc, Newington, N.H., United States of America) until the desired temperatures (10° C. to 145° C. in 5° C. intervals) were attained, the samples were then placed in an insulating block to measure the dielectric properties. The temperature was measured again after the dielectric properties were read to ensure that the temperature was within 2° C. of the set point. Three repetitive measurements were performed for each duplicated samples.

Example 3

Rheological Tests

Constant rate measurement of sweetpotato puree viscosity as a function of shear rate was performed at 25° C. with a StressTech rheometer (Reologica Instruments AB, Lund, Sweden) using a cone and plate geometry (C40 4). Apparent viscosity was recorded as shear rates were ramped from 0.1/s to 300/s. Two repeated measurements were performed on each of the duplicated samples.

Example 4

Color Analysis

Objective colors of the samples were measured with a Hunter colorimeter (Hunter Associates Laboratory Inc., Reston, Va., United States of America). Results were expressed as tri-stimulus values: $L^*$ (lightness, 0 for black, 100 for white); $a^*$ ($-a^*$=greenness, $+a^*$=redness); and $b^*$ ($-b$=blueness, $+b$=yellowness). See CIE, 1976. The instrument (45°/0° geometry, D25 optical sensor) was calibrated against a standard white reference tile ($L^*$=92.75, $a^*$=−0.76, $b^*$=−0.07). The puree samples were filled into a 60×15 mm covered Petri dishes (Becton Dickinson Labware, Franklin Lakes, N.J., United States of America). Six measurements were performed for each sample and average values were used in the analysis.

Example 5

Tests in a 5 kW Microwave Unit

A continuous flow microwave-heating unit (Industrial Microwave Systems, Morrisville, N.C., United States of America) was used for processing SPP. The unit included a 5 kW microwave generator operating at 915 MHz, a waveguide of rectangular cross-section, in which a directional coupler was attached, and a specially designed applicator. A tube of 1.5" nominal diameter (0.038 m ID) made of polytetrafluoroethylene (PTFE or TEFLON®) was placed at the center of the applicator. The exposure region to the microwaves was 0.125 m long. The power delivered by the microwave generator and the power reflected back were measured using diodes located in the directional coupler and a software written in LabView software (National Instruments Corp, Austin Tex., United States of America). This software also controls the amount of power the generator delivers to the product.

Ten liters of SPP were pumped using a positive displacement pump (Model MD012, Seepex GmbH+ Co, Bottrop, Germany) at a rate of 0.5 L/min. Temperatures at various radial locations were measured using a thermocouple arrangement described in Coronel et al., 2003 and recorded using a datalogger (Keithley DAS-16, Keithley Metrabyte, Taunton, Mass., United States of America). The power of the generator was adjusted using the control software to ensure that the product attained the required centerline temperature at the exit of the applicator. The product was then cooled in an ice-water bath and samples were taken for further analysis.

Example 6

Test in the 60 kW Microwave Unit

Figure 12:
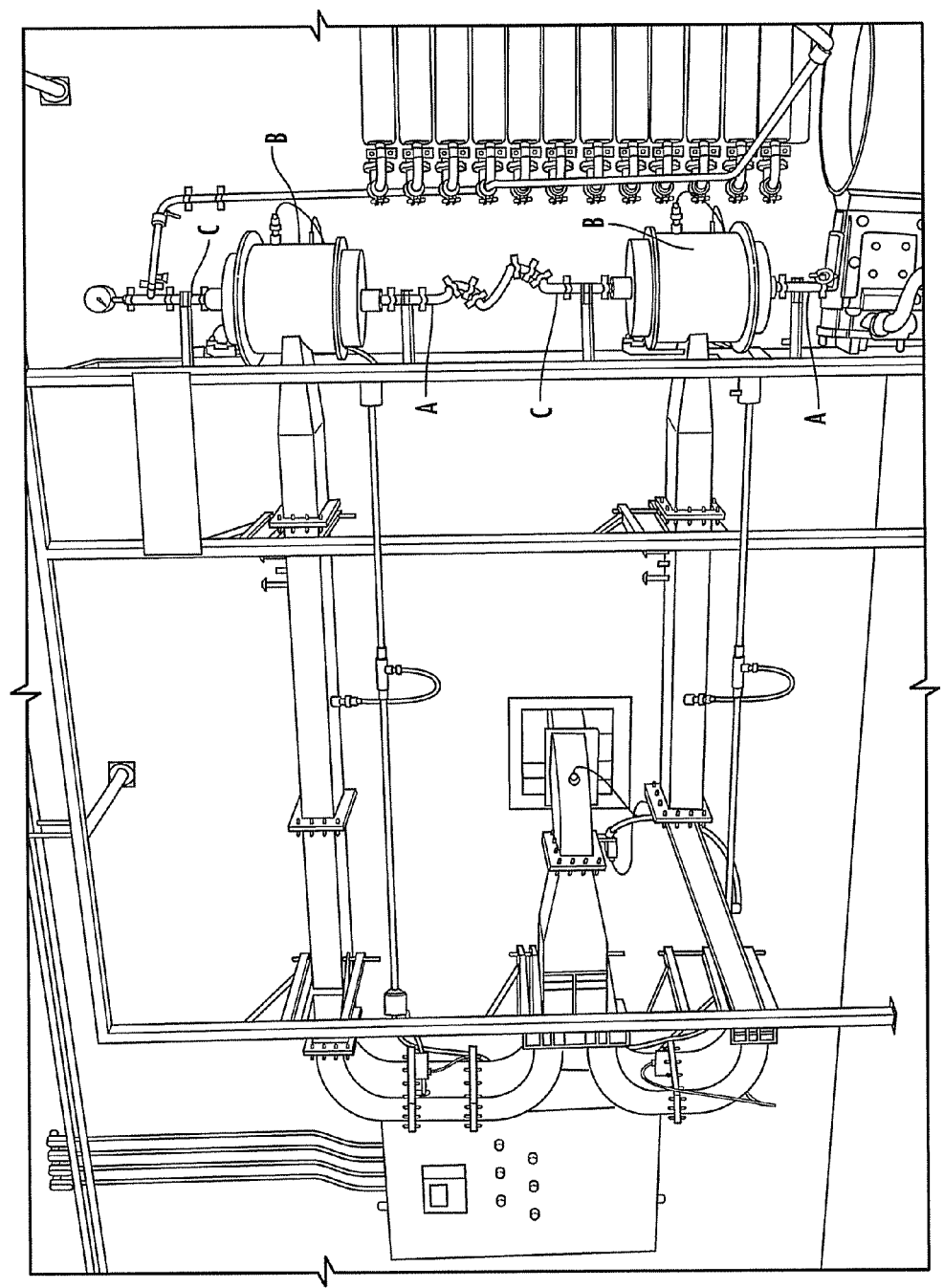
FIG. 12 is a drawing of an installed two-stage continuous flow microwave heater implementing two focused cylindrical microwave heaters/reactors—locations of preceding, concurrent, or subsequent mixing implementation are indicated (A, B, and C; respectively).

Based on the results obtained in the tests in the 5 kW unit, processing conditions were established for a test in a 60 kW continuous flow microwave-heating unit (Industrial Microwave Systems, North Carolina, United States of America) operating at 915 MHz (depicted in FIG. 12). The power delivered by the generator was monitored by a control panel supplied by the manufacturer. The microwaves were delivered to the product by a waveguide of rectangular cross-section, which were split into two sections and geared toward two specially designed applicators, with a directional coupler in each as seen in FIG. 1. A PTFE tube (0.038 m ID) was placed at the center of each applicator and the exposure region was 0.2 m long in each applicator.

A positive displacement pump (Model A7000, Marlen Research Corp., Overland Park, Kans., United States of America) was used to pump the product through the system. Temperatures were measured at the inlet of the system, the inlet and exit of each applicator, and at the holding tube exit. Arrangements of the thermocouples were as described by Coronel et al., 2003. The temperatures were recorded at 4-second intervals using a Datalogging system (HP 3497A, Hewlett Packard, Palo Alto Calif., United States of America). The temperature at the exit of the system was achieved by controlling the power generated by the microwave system.

The system was first sterilized using an aqueous solution of NaCl and sugar, which was heated to 130° C. and recirculated for 30 minutes. The product was heated to 135-145° C., held for 30 seconds, rapidly cooled in a tubular heat exchanger, and then aseptically packaged in aluminum-polyethylene laminated bags (Scholle Corp, Chicago, Ill., United States of America) using a bag-in-box unit (Model PT.A.F., Astepo, Parma, Italy). The puree bags were stored at ambient temperature (22° C.) and two bags were randomly taken for microbiological analysis after 1, 15, and 90 days. A standard plate count assay was used to enumerate total aerobic bacteria in the sweetpotato puree samples. Fifty gram samples were aseptically transferred to sterile filter bags (Spiral Biotech, Bethesda, Md., United States of America) containing 50 ml of sterile physiological saline solution (0.85% NaCl), and the bags were macerated with a Tekmar stomacher (Model TR5T, Tekmar Co., Cincinnati, Ohio, United States of America) on high speed for 160 seconds. Appropriate dilutions of the stomacher filtrate were made using sterile physiological saline solution and spread onto duplicate PCA agar plates using an Autoplate 4000 spiral plater (Spiral Biotech). The PCA plates were inoculated and grown at 37° C. for 48 hours for total aerobic bacterial counts. Sample dilutions were also spread onto plates of yeast/mold agar plates and inoculated for enumeration of yeast and mold colonies. Medium preparation was carried out following standard procedures (DIFCO, 1998).

Data were subjected to the analysis of variance (SAS Institute, Cary, N.C., United States of America). Statistical testing was performed at the 95% ($p<0.05$) confidence level.

Discussion of Examples 1-6

Figure 2:
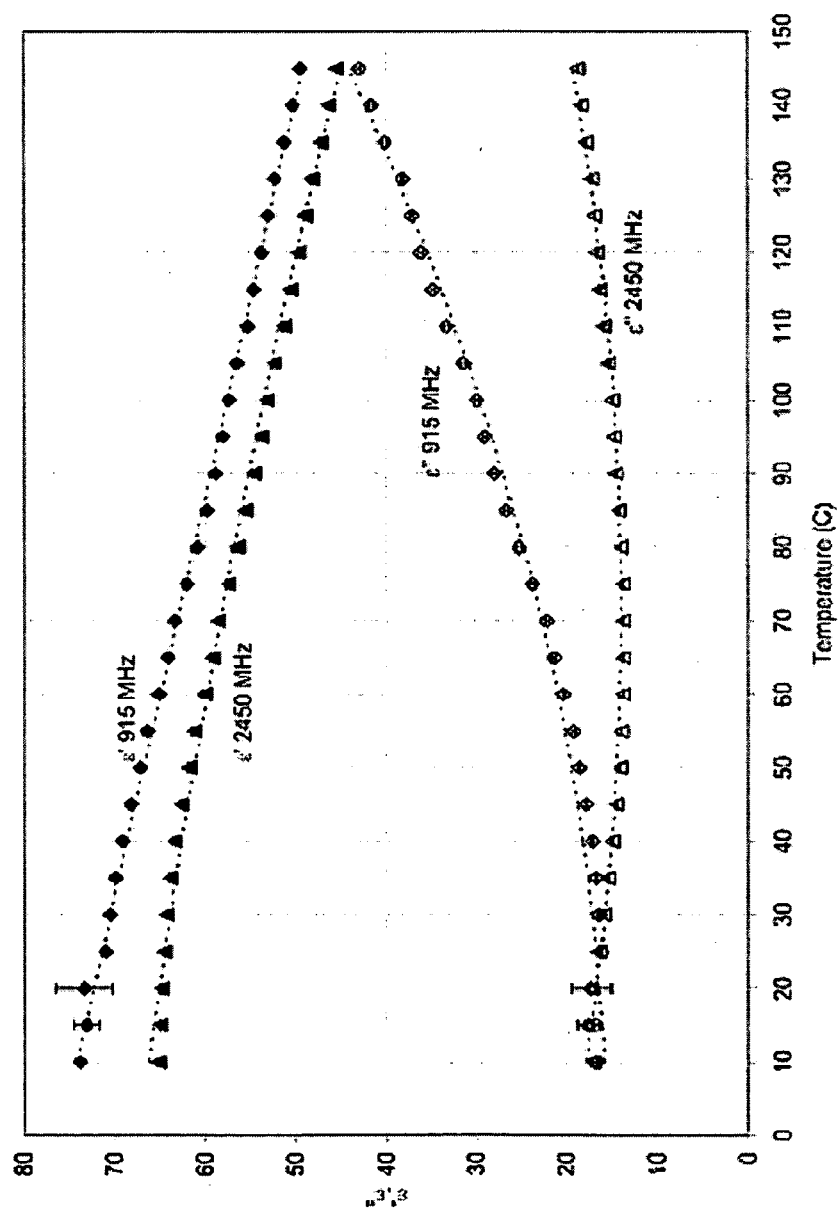
FIG. 2 is a plot depicting the dielectric properties of sweetpotato puree (SPP) at 915 and 2450 MHz.

Dielectric Properties. The dielectric properties of the sweetpotato puree disclosed herein were compared to those reported by Fasina et al., 2003 and shown in FIG. 2. The correlations for dielectric properties provided in Fasina et al., 2003 were in good agreement with the measured values of $\in'$ (dielectric constant) and $\in'$ (loss factor). The differences were more noticeable in the values of $\in''$, which is likely a result of compositional and moisture variations observed in agricultural products (Sipahioglu and Barringer, 2003). The effect of temperature on the dielectric constant was similar for both 915 and 2450 MHz, with $\in'$ decreasing with an increase in temperature, with values of 71.5 at 10° C. and 60.8 at 95° C. for 915 MHz, and with values of 67.1 at 10° C. and 61.1 at 95° C. for 2450 MHz. The loss factors followed a trend of increased $\in'$ with increasing temperature, with values of 18.1 at 10° C. and 26.7 at 95° C. for 915 MHz. However, at 2450 MHz $\in'$ decreased with an increase in temperature with values of 18.4 at 10° C. and 16.1 at 95° C.

Figure 3:
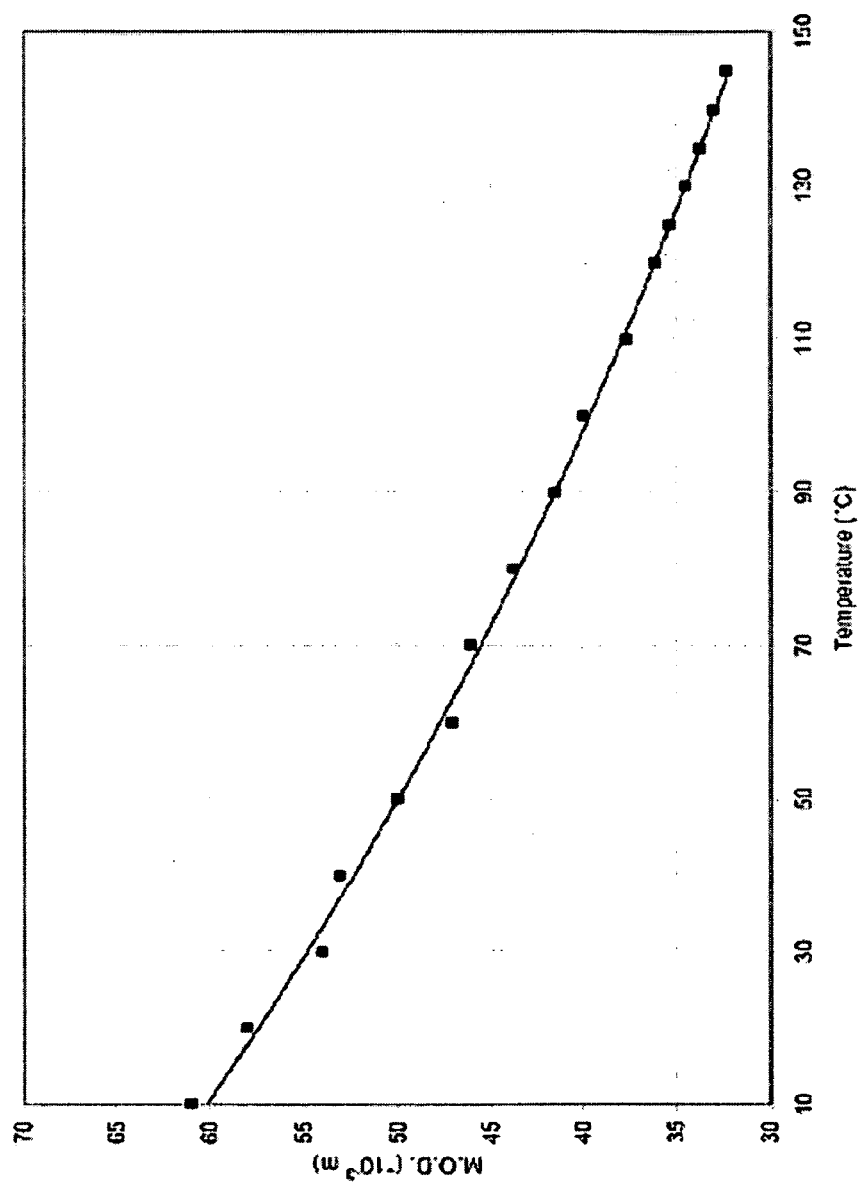
FIG. 3 is a graph showing how maximum operating diameter (M.O.D.) relates to temperature for SPP at 915 MHz.

The maximum operating diameter (MOD) of the tube to be used in the applicator was calculated using the method proposed by Coronel & Simunovic, 2004 that involves a solution of the Helmholtz equation in cylindrical coordinates, and the results are shown in FIG. 3. Briefly, the penetration depth of the microwaves was calculated by solving the penetration equation in cylindrical coordinates considering a constant E field in the outside of a cylinder with a diameter of 38 mm (1.5 inches). The differential equation was a Helmholtz type equation:

$$\nabla^2 E + \gamma^2 E = 0$$

$$\gamma = \alpha + j\beta$$

B.C.

$$r = R \quad E = E_0$$

Where $\gamma$ is the propagation constant and $\alpha$ and $\beta$ are defined as:

$$\alpha = \omega \sqrt{\frac{\mu\varepsilon}{2}\left[\sqrt{1+\left[\frac{\sigma}{\omega\varepsilon}\right]^2} - 1\right]}$$

$$\beta = \omega \sqrt{\frac{\mu\varepsilon}{2}\left[\sqrt{1+\left[\frac{\sigma}{\omega\varepsilon}\right]^2} + 1\right]}$$

The solutions to this equation were given by Bessel functions in the form:

$$E(r) = C_1 J_0(\gamma r) + C_2 Y_0(\gamma r)$$

The value of the constants depended on the dielectric properties of the material and dimensions of the tube. The MOD was considered the diameter in which:

$$E_{r=0}/E_0=1.$$

Thus, the maximum operating diameter (MOD) was defined as the maximum diameter that can be used in continuous flow processing to obtain the necessary heating across the cross-sectional area, and it was calculated at different temperatures. It can be observed that MOD decreases with temperature with values of 0.22 m at 10° C. and 0.12 m at 95° C. for 915 MHz. The increase in the loss factor with temperature makes energy conversion into heat more effective, thus decreasing the penetration depth and hence, the M.O.D. (see FIG. 3)

Tests in a 5 kW Microwave Unit. The product was processed using the 5 kW microwave unit, keeping a constant holding time and changing the centerline exit temperature. The desired centerline exit temperatures were 110, 130, and 140° C. with an exposure time in the heating section of 17 seconds and a holding time of 90 seconds. The product was cooled rapidly in an ice-water bath and samples were taken for analysis of the rheological properties and color.

Figure 4:
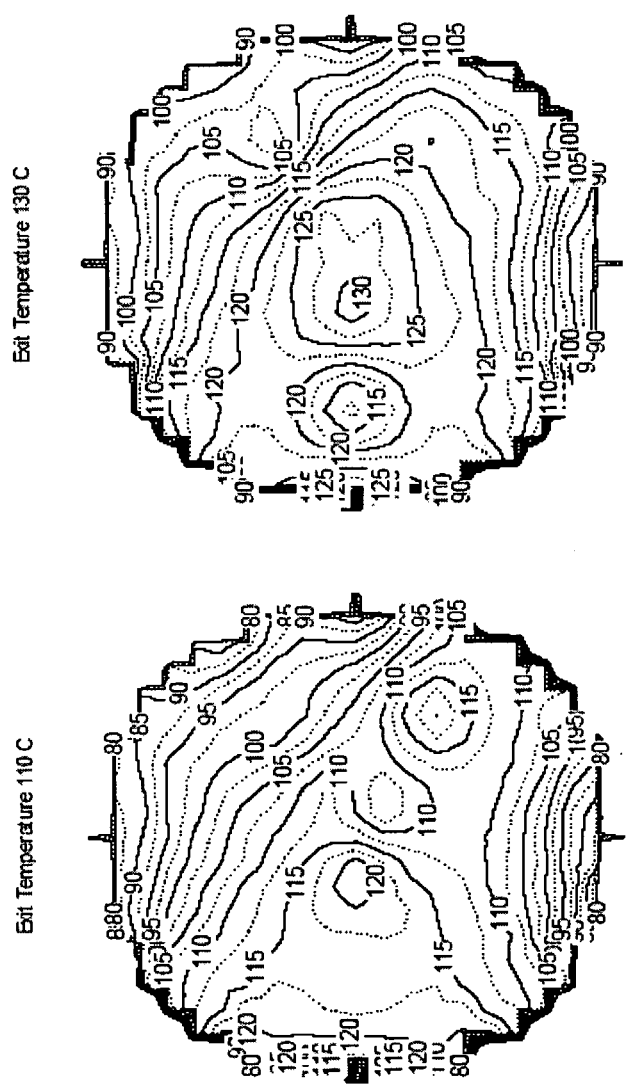
FIG. 4 depicts typical temperature profiles at the exit of the heating section in the 5 kW tests.

Large temperature differences were observed between the walls and the center of the applicator tube. The differences between the maxima and minima were 35, 40, and 43° C. for centerline exit temperatures of 110, 130, and 140° C. respectively with average exit temperatures of 80, 101, and 107° C. respectively. FIG. 4 shows the interpolated temperature profiles in the cross section of the tube at the exit of the heating section for the exit temperatures of 110 and 130° C. It can be observed in FIG. 4 that the highest temperature is achieved close to the center of the tube, and the minimum close to the walls.

Figure 5:
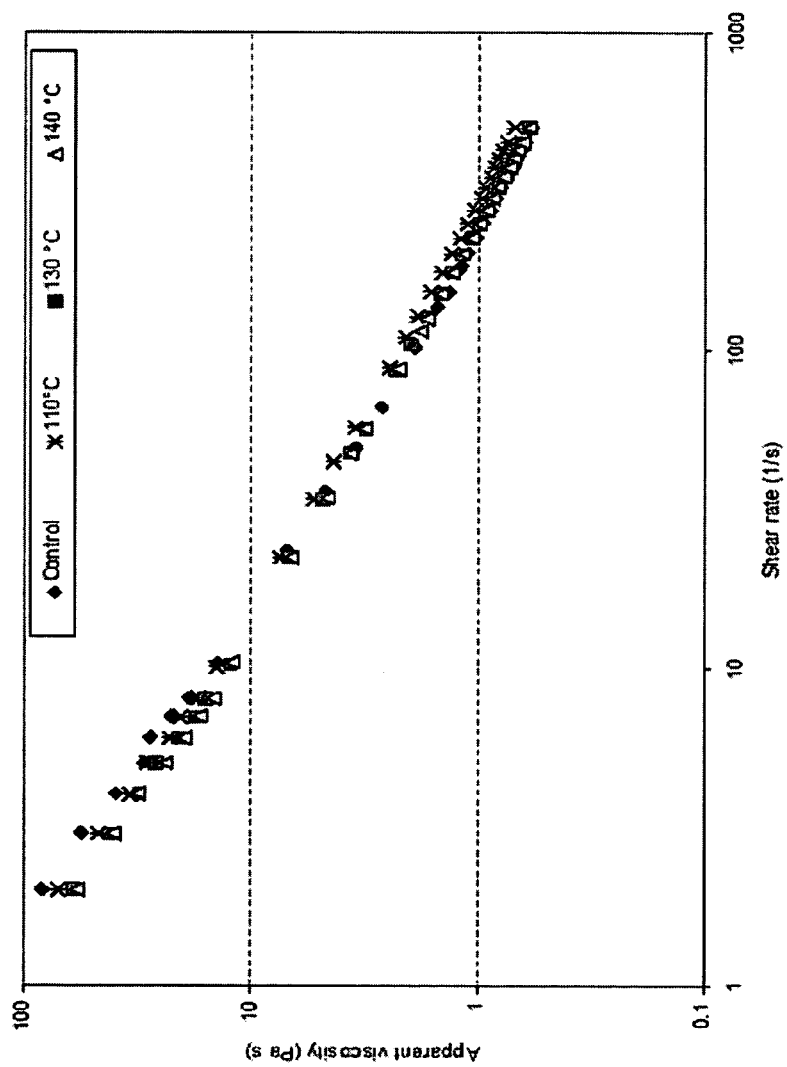
FIG. 5 depicts the rheological properties of SPP samples from the 5 kW tests.

The rheological properties of the samples treated to different centerline exit temperatures are shown in FIG. 5. All the samples exhibited shear-thinning behavior (i.e., lower apparent viscosity at higher shear rates). The rheological behavior was modeled using a Herschel-Bulkley model ($\sigma=\sigma_0+K\gamma^n$), wherein $\sigma$ is sheer stress (Pa), $\sigma_0$ is yield stress, K is the consistency index (Pa s$^n$), $\gamma$ is the shear rate (1/s), and n is the flow behavior index as described in Steffe, 1996. The average values of the parameters were: yield stress ($\sigma_n$) 89.01±2.67 Pa, the consistency index (K) 18.78±1.76 Pa, and the average flow behavior index (n) 0.39±0.07. In FIG. 5 it can be seen that the apparent viscosity of the different SPP samples did not show significant differences between treatments.

Figure 6:
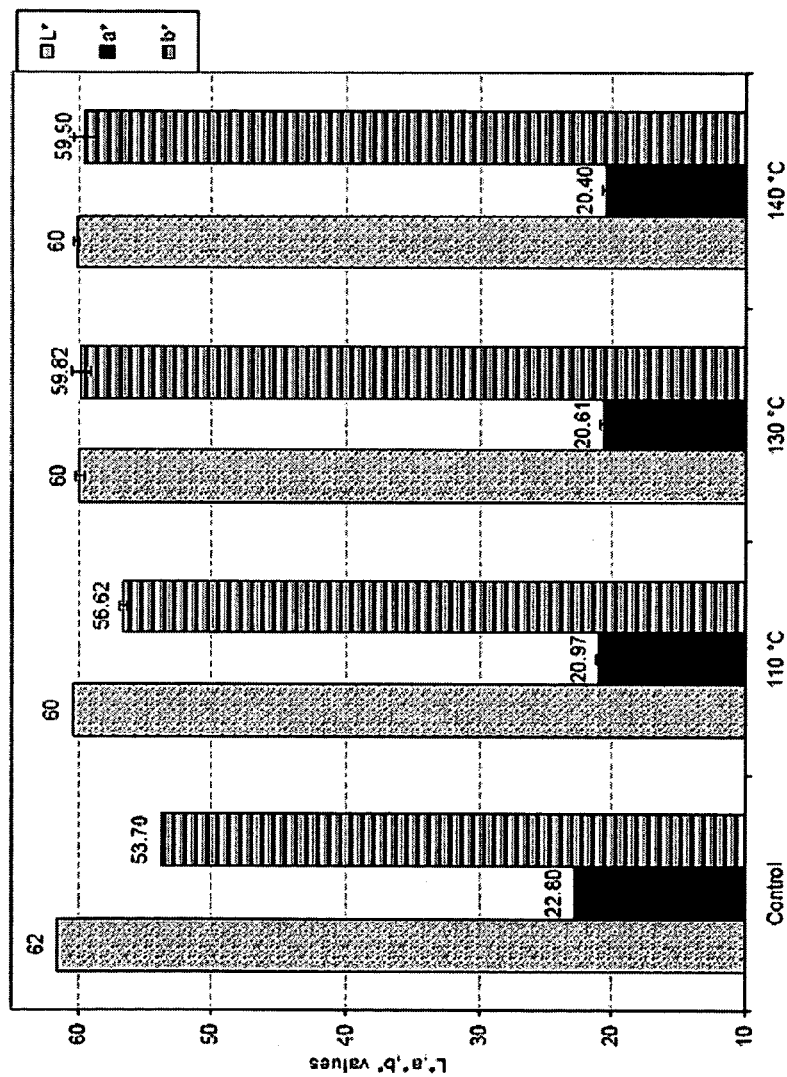
FIG. 6 depicts color measurements of SPP samples from the 5 kW tests.

Color measurements of the samples corresponding to different centerline exit temperatures are shown in FIG. 6. All the samples presented an increase in b* value (yellowness; 5% for the 110° C. treatment and by 10% for the 130° C. and 140° C. treatments) and a decrease in a* value (redness; 9% for the 110° C. treatment, and 10.5% for the 130° C. and 140° C. treatments), while the L* value (lightness) remained changed 2% for all treatments. The total change in color ($\Delta E$) is expressed as the result of the following equation:

$$\Delta E=(\Delta L^{*2}+\Delta a^{*2}+\Delta b^{*2})^{1/2}$$

$\Delta E$ values were 10, 20, and 20 for centerline exit temperatures of 110, 130, and 140° C., respectively.

Tests in a 60 kW Microwave Unit. With the information gathered from the tests on 5 kW microwave unit, the test runs using the 60 kW unit were carried out as a pilot plant experiment aiming to obtain a shelf-stable product. The flow rate was set to 4.0 L/min, and in order to obtain a shelf-stable product the centerline temperature at the exit of the holding tube required was 135° C. with a holding time of 30 seconds ($F_o$=30 minutes). The power generated by the system was adjusted in order to achieve the required centerline exit temperature.

Figure 7:
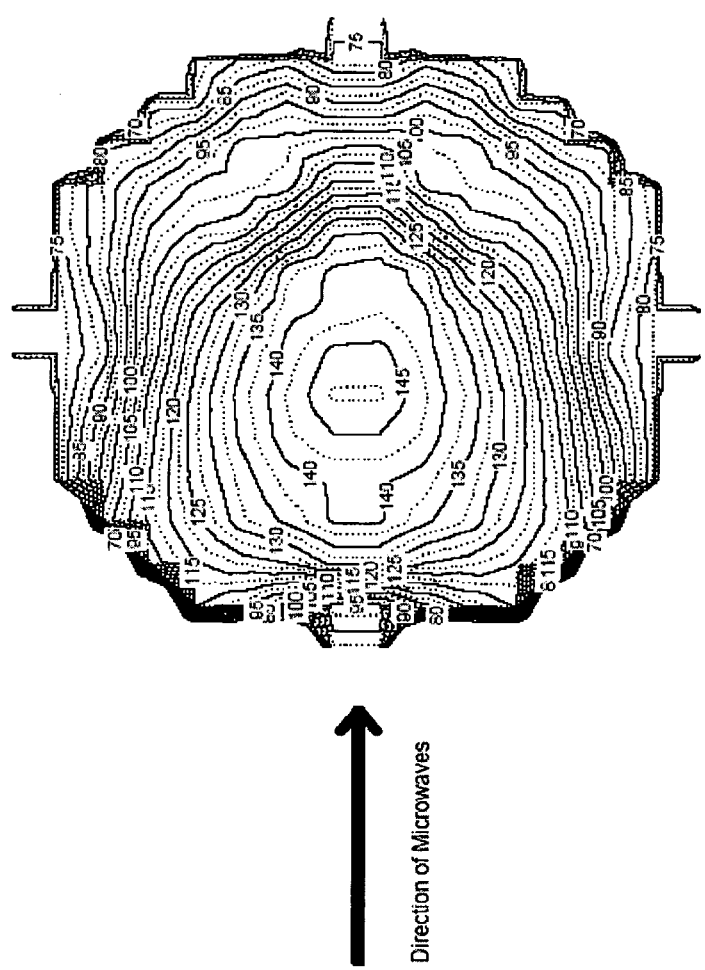
FIG. 7 depicts a typical temperature profile at the inlet of the holding tube during the 60 kW test in the absence of static mixers.

As observed in the 5 kW tests, the temperature differences between the centerline (135° C.) and the walls (70° C.) of the tube were large, as shown in FIG. 7. Because of the high viscosity of the SPP no mixing occurred in the holding tube. Therefore, the product closer to the walls was that which received the least thermal treatment with ($F_o$<0.1 minute). However, the product was kept refrigerated and no microbial growth was detected after 30 days.

In order to minimize the non-uniformity in temperature within the product, static mixers were implemented at the exit of each of the microwave applicators of the system. The mixing at the exit of the heaters would diminish any temperature differences within the product at the exit of the heaters in order to improve the thermal treatment and in consequently the shelf life of the product. The second experiment was carried out with centerline exit temperature of 140° C. at the exit of the second heater, and a holding time of 30 seconds. The centerline temperature was increased in order to achieve a minimum temperature of 135° C. at the end of the holding tube.

Figure 8:
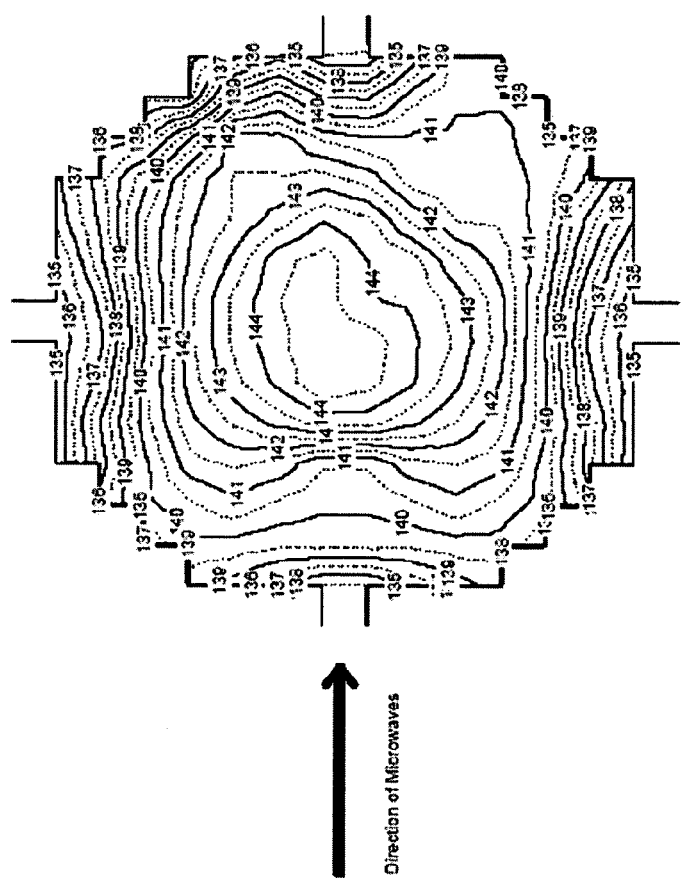
FIG. 8 depicts a typical temperature profile at the inlet of the hold tube during the 60 kW test after static mixers were introduced.

Temperatures throughout the cross-sectional area were more uniform due to the mixing of the product. The temperature differences between center and wall were reduced from 48.4 to 20.1° C. after the first static mixer and from 37.6 to 11.7° C. after the second static mixer. At the inlet of the holding tube, SPP had a temperature profile as shown in FIG. 8, with a minimum temperature of 135° C. and a maximum of 146.7° C. Thus, the fastest particle (at the center of the tube) received the least heat treatment. The fastest fluid elements (center) received a thermal treatment equivalent to $F_o$=23 minutes, which rendered a commercially sterile product, which should be shelf stable. Microbiological tests of the final product were performed in order to confirm the destruction of microorganisms. Microbiological test results on total plate count, molds, and yeast showed no presence of microorganisms after 1, 15, and 90 days.

Conclusions. Aseptically packaged sweetpotato puree was successfully produced using a continuous flow microwave heating system. The resulting product packed in flexible plastic containers had the color and apparent viscosity comparable to the untreated puree, and was shelf-stable. This process can be applied to several other vegetable and fruit purees.

Example 7

Effect of Mixers on Temperature Equalization

Figure 17:
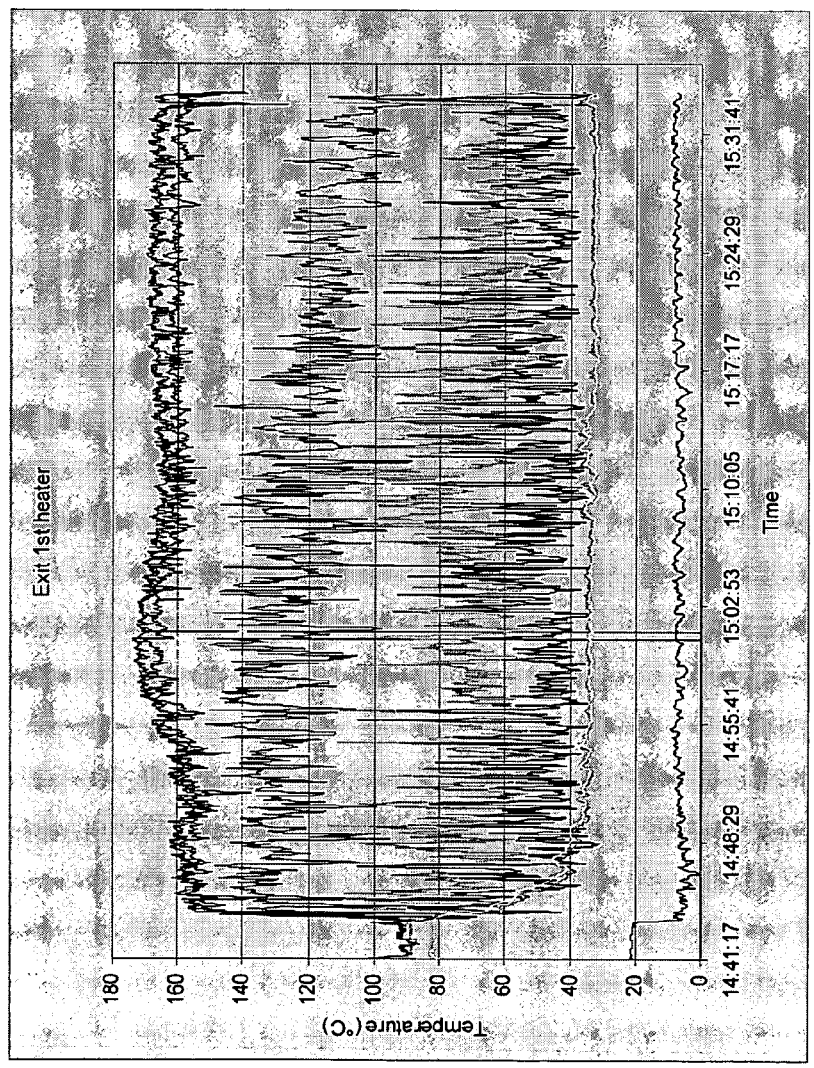
FIG. 17 is a plot depicting the temperature distributions that can be expected and encountered at flow rates and temperature increase conditions approaching the industrial sterilization levels. The graph displays temperatures at the exit of the $1^{st}$ stage of the 60 kW microwave heating installation. Temperature distribution and variations are substantial. If such unfavorably heated flow and temperature distribution were allowed to enter the $2^{nd}$ heating stage in unmodified form, there would be a possibility of developing extreme temperature and pressure conditions and hazardous equipment and installation failures.
Figure 19:
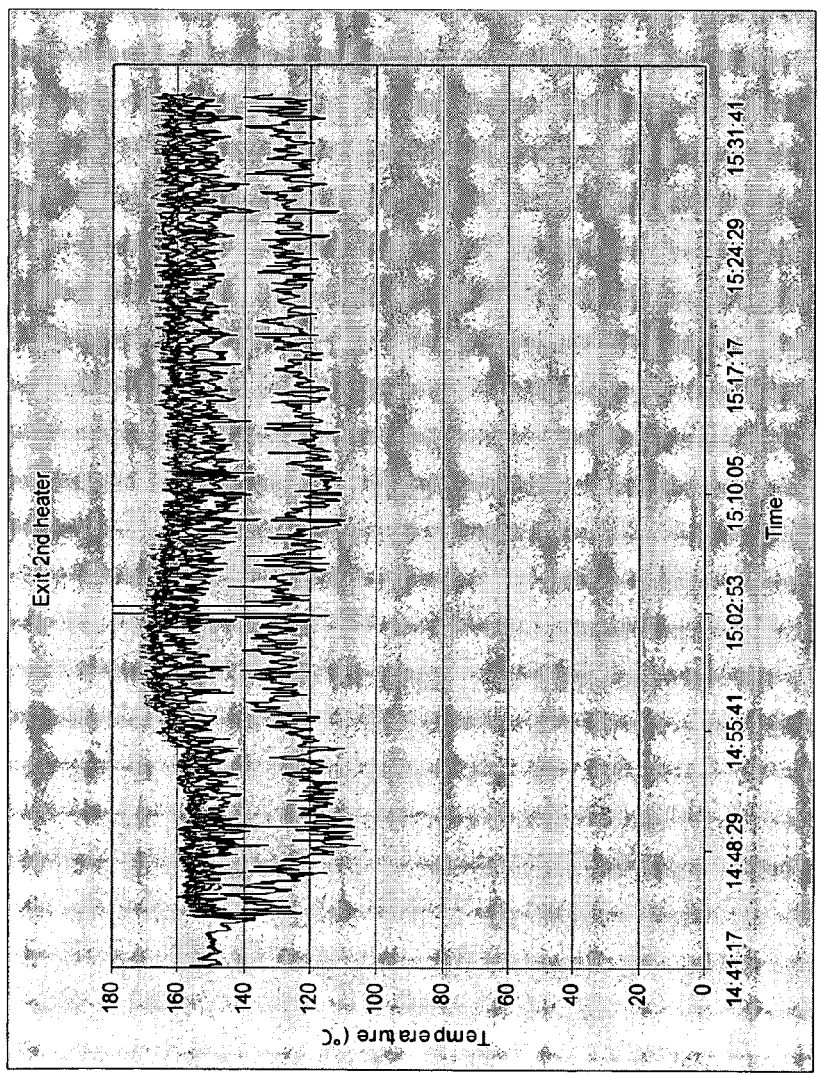
FIG. 19 is a plot depicting the temperature distribution at the cross section of the exit of the second heating stage. While much narrower than the distribution recorded at the exit of the $1^{st}$ heating stage; the distribution is still quite significant. Some regions of the flow profile might not have achieved the intended sterilization-level temperatures, in spite of the on-target delivery of temperature increase for the bulk material flow. If this temperature distribution was introduced into the flow-through hold section without the necessary mixing step, these flow regions (lower temperature) can be and stay in contact with the external (colder) perimeter of the hold tube flow profile and remain inappropriately sterilized, possibly resulting in microbial product spoilage during storage.

SPP was treated in the 60 kW unit as described hereinabove, and the temperature of the material was tested using thermocouples at the exit of the first and second heaters in the absence of any mixing devices. FIGS. 17 and 19 depict the wide variation in heat across the cross section of the flow. The need for a mixing implement subsequent to the heating stage is thus illustrated by temperature distribution measurements and proven by the unsuccessful sterilization results in preceding runs (without the mixing stage).

Figure 18:
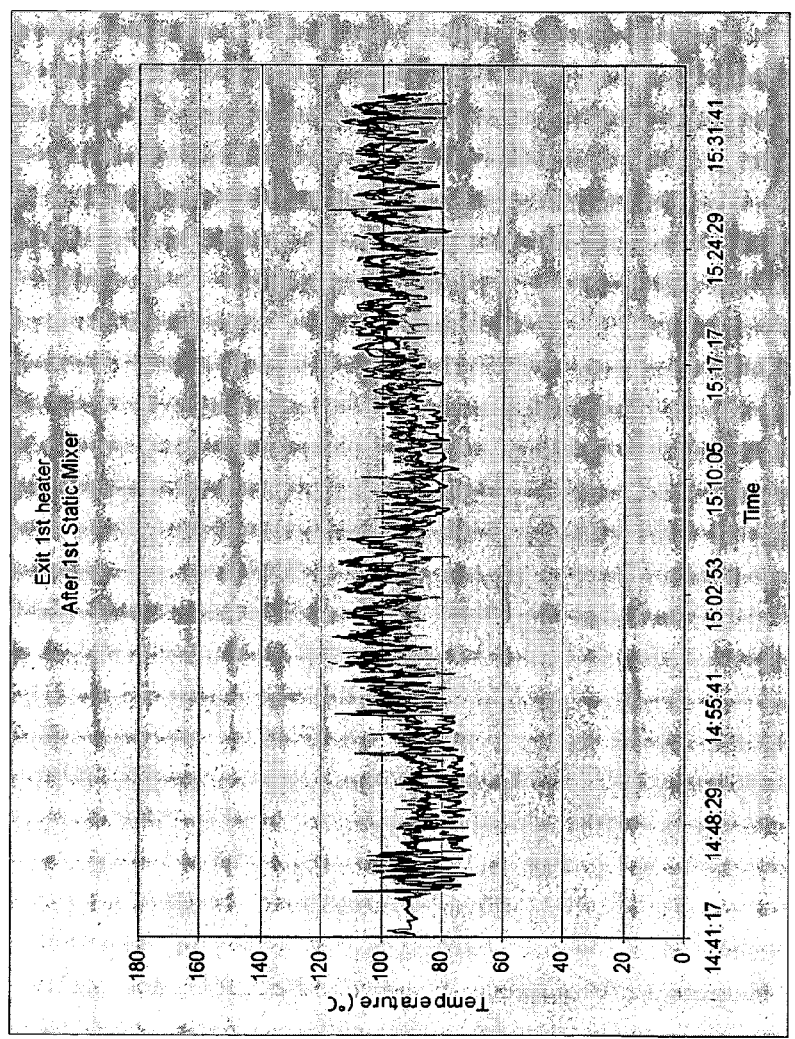
FIG. 18 is a plot depicting the temperature distribution and values of the same flow stream after it has passed through the $1^{st}$ static mixer installation. Temperature distribution is significantly leveled, allowing for the introduction of the material flow into the $2^{nd}$ heating stage without significant concern for possible failures.
Figure 20:
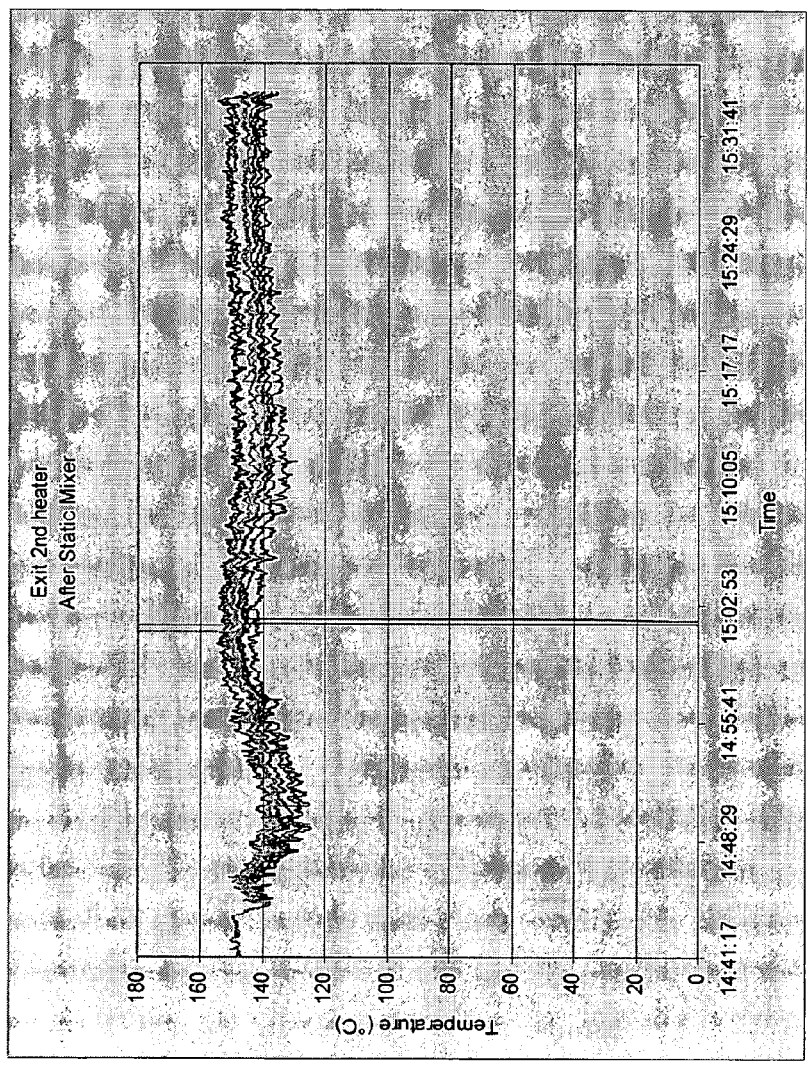
FIG. 20 is a graph of the temperature distributions acquired at the exit cross section of the $2^{nd}$ static mixer, following the $2^{nd}$ heating stage. The distribution is clearly and efficiently minimized and all monitored temperatures across the flow cross-section reach or exceed the intended target sterilization-level temperature. This allows for the safe continuation of processing via entry into the hold tube section and holding the material at a pre-set sterilization level temperature for a pre-determined length of time. Sterility and subsequent shelf-stability of the obtained product is thus achieved.
Figure 21:
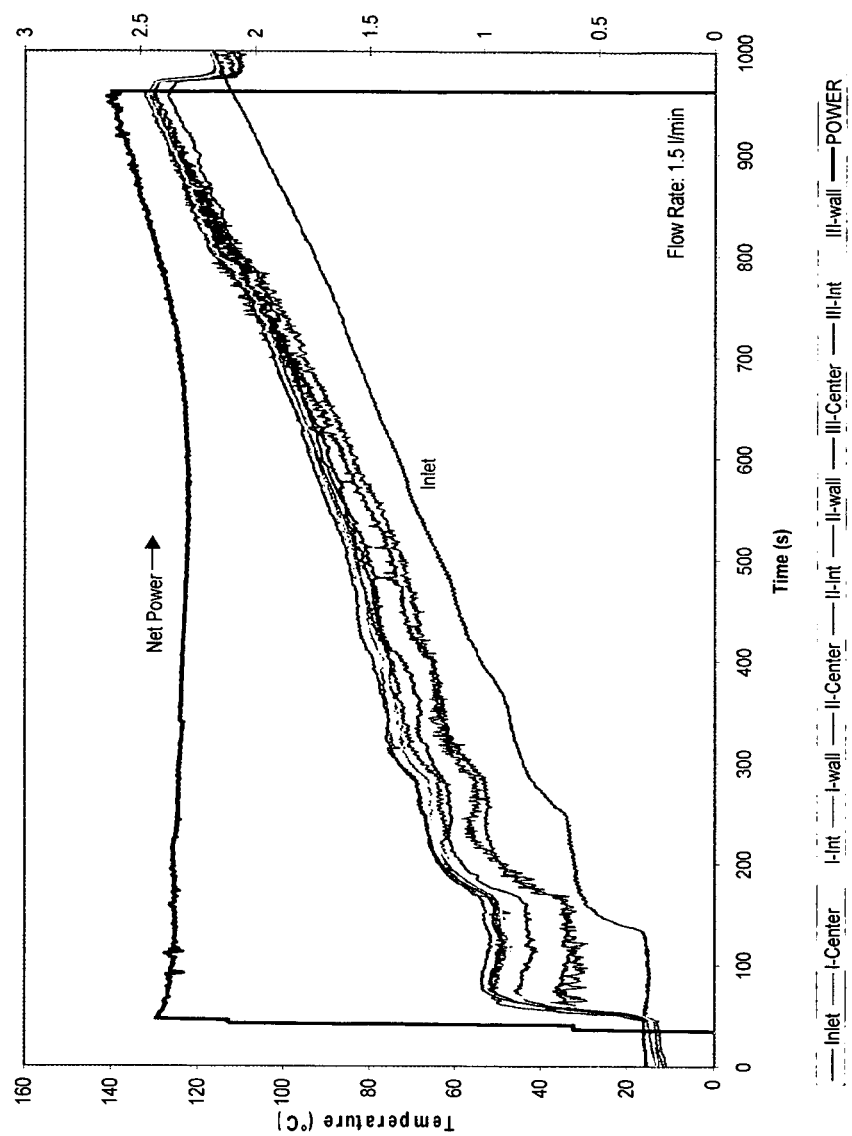
FIGS. 21-25 are plots depicting the equivalent processing and temperature distribution profile sequence for another difficult to process, high-viscosity, poor conductivity product—white (Irish) potato puree (i.e., mashed potatoes). Attached figures are equivalent to figures shown for the sweetpotato product—and cover temperature distribution after recirculated heating using the 5 kW installation (FIG. 21), unacceptably wide temperature distribution at the exit of the $1^{st}$ heating stage of a two-stage 60 kW installation (FIG. 22), positive effect of utilizing a static mixer following the $1^{st}$ heating stage and the resultant significant reduction in temperature variability and distribution (FIG. 23); another relatively wide distribution of temperatures at the exit of the $2^{nd}$ heating stage (FIG. 24), and finally, a near-perfect, very narrow distribution after the implementation of the $2^{nd}$ static mixing device (FIG. 25), allowing the entry of the material into the holding section of the process, under controlled, well-maintained and narrow temperature distribution conditions, providing a superior process and a superior commercially sterile, shelf-stable product.

Static mixers were then installed and the experiment repeated. FIGS. 18 and 20 depict the temperature equalization across the cross section of the flow as shown by the much narrower temperature distribution.

Figure 22:
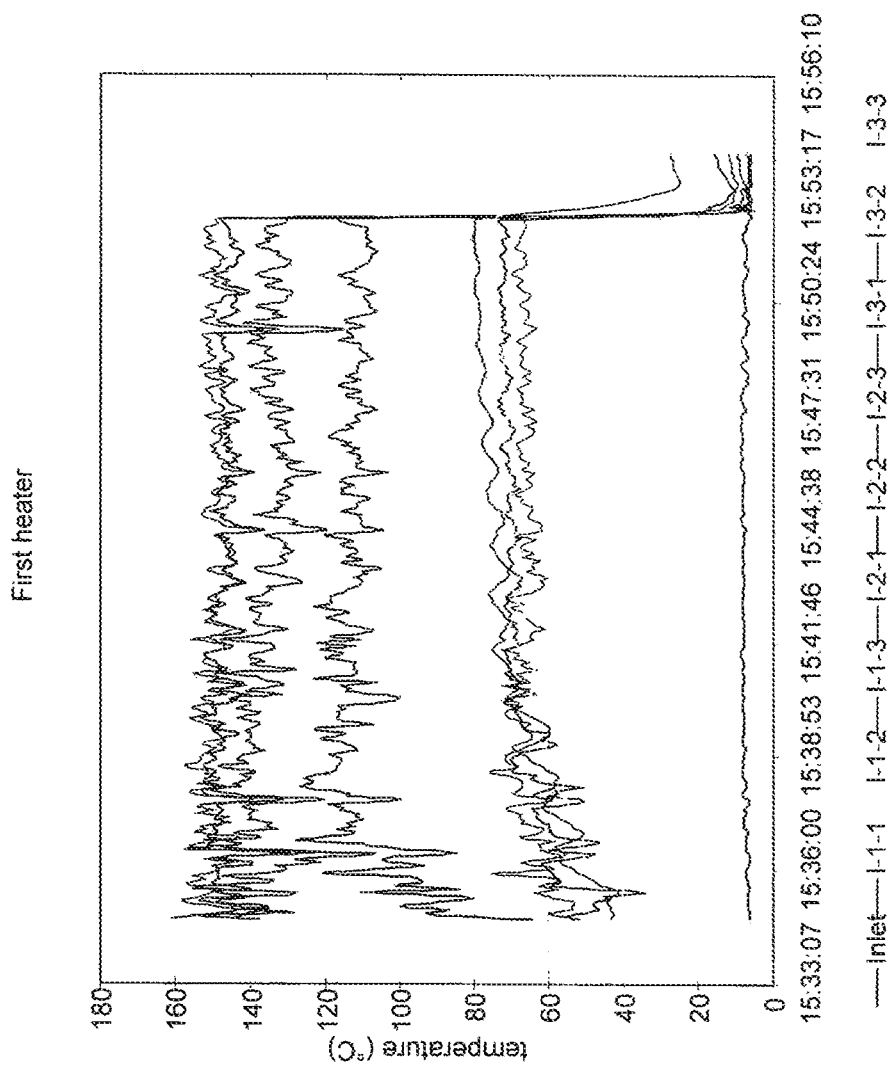
Figure 23:
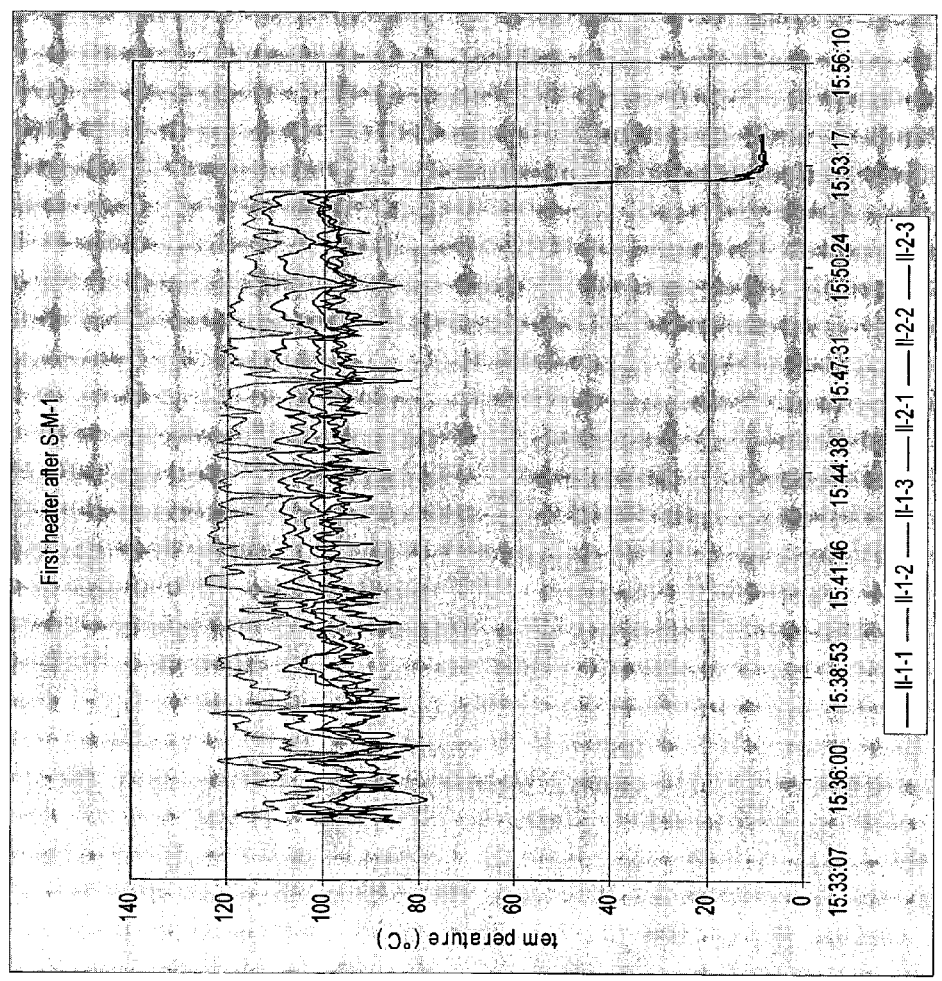
Figure 24:
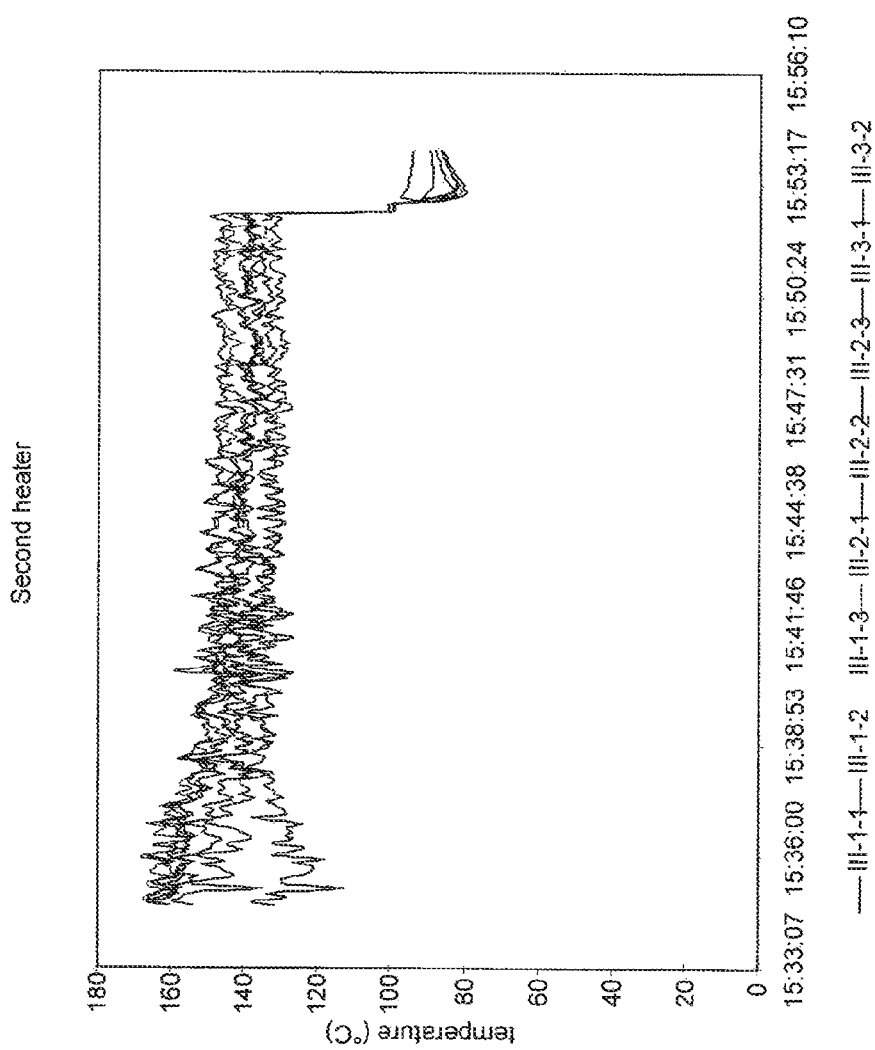
Figure 25:
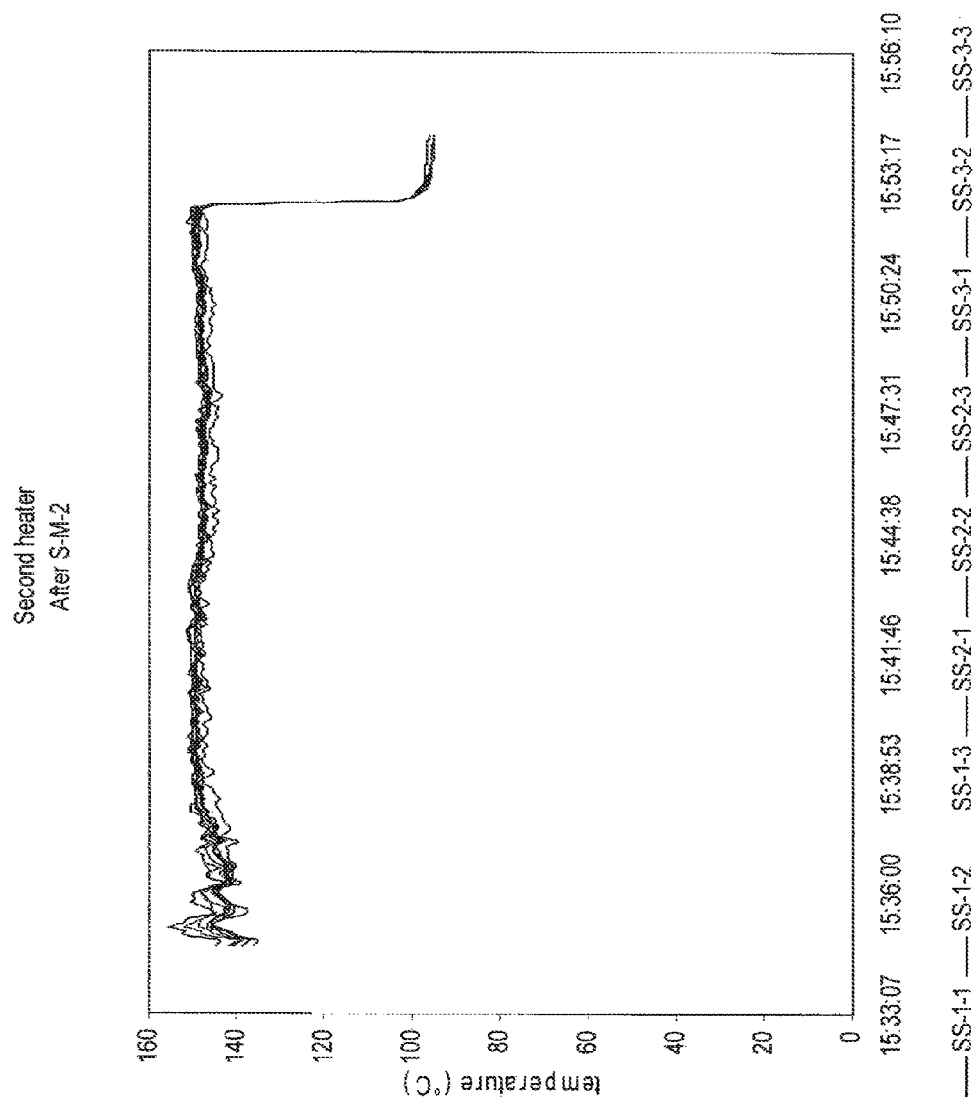

These experiments were repeated using a white potato puree (i.e., mashed potatoes). FIGS. 22 and 24 depict the temperature distribution at the exit of the first and second heaters in the absence of any mixing devices, and FIGS. 23 and 25 depict the temperature equalization across the cross section of the flow as shown by the much narrower temperature distribution.

Example 8

Treatment of Green Pea, Carrot, and White Potato Purees

Sample Preparation. Frozen green peas and carrot purees were purchased from Stahlbush Island Farm Inc. (Corvallis, Oreg., United States of America). Refrigerated mashed potatoes were obtained from Reser's Fine Foods (Beaverton, Oreg., Unites State of America) and made into a purple colored puree by adding 300 grams of anthocyanin solution (San Red YM-EX, San-Ei Gen F. F. I. Inc., New Jersey, United States of America) and 7.5 liters of water per 150 pounds of mashed potato. The materials were thoroughly mixed using a high shear mixer (Rotosolver Mixer model 112RS113 with a Baldor 7.5 HP, 1725 rpm motor controlled by a Woods Model WFC2007-5CHT AC Inverter from Admix, Manchester, N.H., United States of America).

The green pea and carrot purees were passed through a 5 kW microwave unit as described in Example 5. The power of the generator was adjusted using the control software to attain the centerline temperature of the product at 75° C., 100° C., 110° C., 120° C., 125° C. and 130° C. at the exit of the applicator. Samples of the microwave-heated purees were collected and immediately cooled in an ice-water bath, and then stored at 4° C. for further analysis within 3-4 days.

With the 60 kW microwave unit, these vegetable purees (green peas, carrots, and potatoes) were processed as described in Example 6, except that the system was not connected to an aseptic filler. The microwave-heated purees were continuously re-circulated for 6 hrs in the 60 kW system with a centerline exit temperature of 125-130° C. Samples were taken at time intervals, immediately cooled, and stored at 4° C. for further analysis.

Rheological Tests. Dynamic rheological test was conducted using a StressTech rheometer (Reologica Instruments AB, Lund, Sweden) with 20 mm parallel plate geometry at 25° C. Puree samples were transferred onto the plate of the rheometer. The upper plate was lowered onto the gel to a gap of 1.5 mm and excess material was trimmed from the periphery. After the sample was equilibrated at 25° C. on the plate for 1 minute, small strain oscillatory testing was carried out at 25° C. The sample was subjected to oscillatory sweep at a frequency range from 0.01 to 20 Hz. The oscillatory stress was set at 2 Pa, which was within the linear viscoelastic region of the tested purees. The storage modulus G', loss modulus G", and dynamic viscosity $\eta^*$ were examined. Two repeated measurements were performed on each puree sample.

Color Analysis. Color analysis was performed as described in Example 4.

Discussion of Example 8

Figure 26:
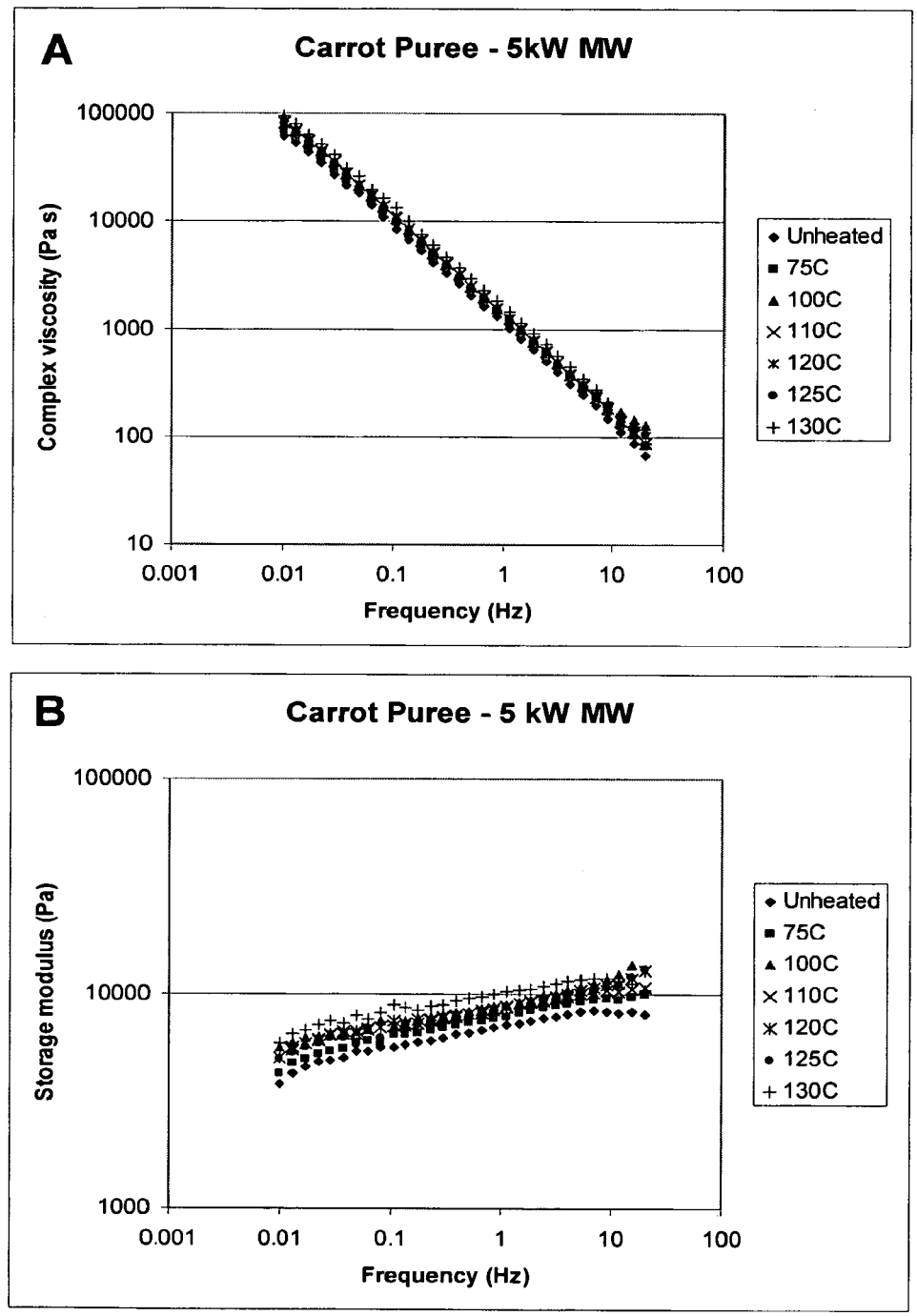
FIGS. 26A and 26B depict the rheological properties of carrot puree samples processed at various temperatures in the 5 kW microwave unit.

Carrot Puree. The rheological properties of carrot puree samples processed at various temperatures in the 5 kW microwave unit are shown in FIGS. 26A and 26B. The dynamic viscosity ($\eta^*$) of all carrot puree samples decreased with increasing frequency (FIG. 26A), showing pseudoplastic behavior. The mechanical spectra of carrot puree exhibited frequency dependency (FIG. 26B) with G' higher than G", indicating that the material can be classified as weak gels. Increasing the microwaving temperature from 75° C. to 130° C. resulted in a slight increase in the dynamic viscosity of carrot puree.

The effect of microwaving temperature was more manifested in gel strength (G') values (FIG. 26B). This phenomenon might be attributable to the dissociation of bound carbohydrate components of the cell debris into the liquid fraction of the puree resulting in more network formation upon cooling. This effect of microwaving temperature in flow behavior and gelling properties of carrot puree can be beneficial to the processors if a product with slightly increased consistency would be desirable. In any circumstance wherein the puree viscosity and gel strength should be maintained as that of the unheated puree, adjusting the water level in the puree prior to microwave processing can be easily carried out.

Figure 27:
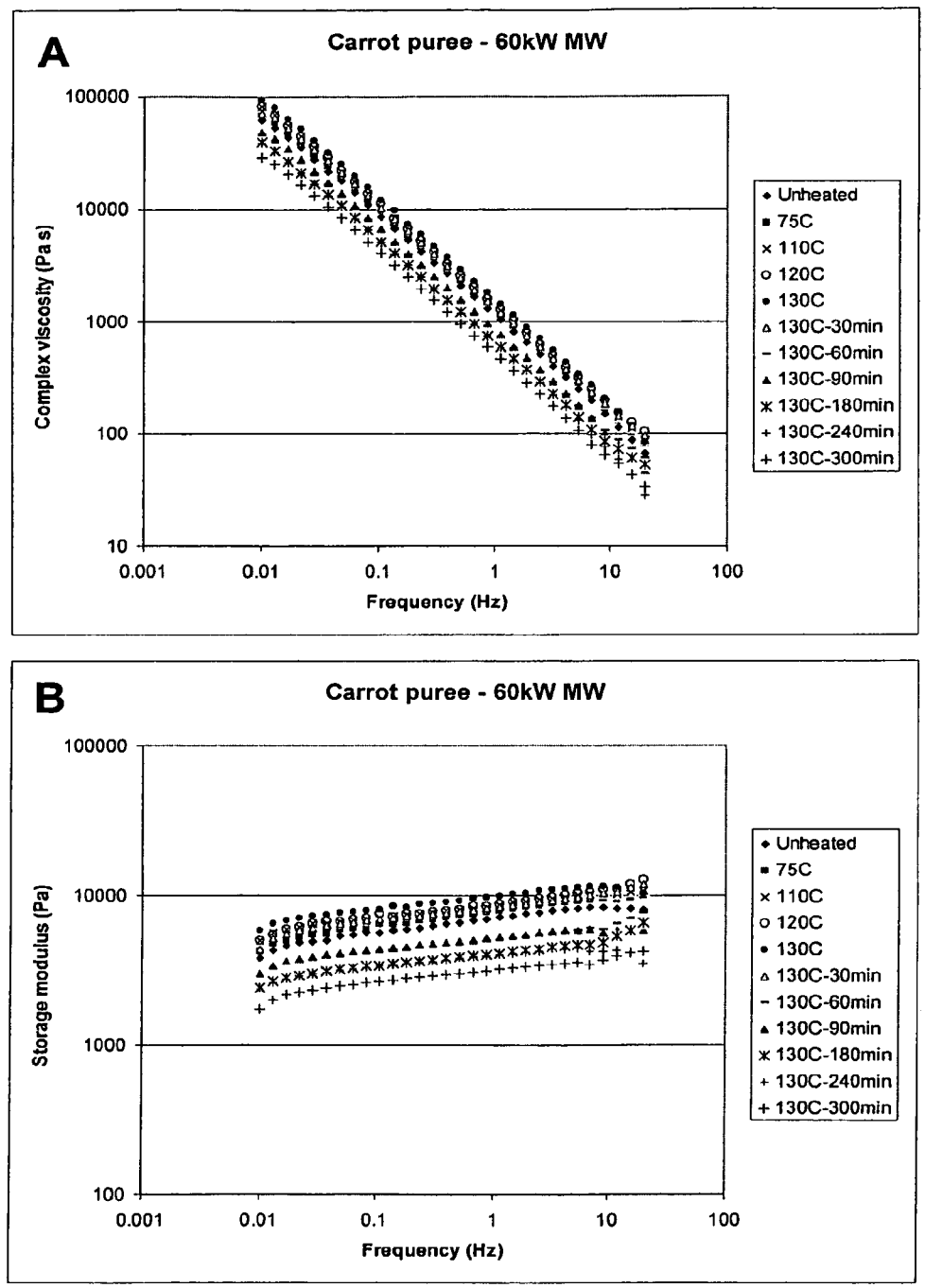
FIGS. 27A and 27B depict the rheological properties of carrot puree samples processed at various temperatures in the 60 kW microwave unit.

Prolonging the microwaving time at 130° C. by re-circulating the carrot puree in 60 kW unit resulted in disrupting the bonding and gel networks as indicated by significant decreases in both $\eta^*$ and G' (FIGS. 27A and 27B). Severe disruptions of the consistency and gel strength of the carrot puree were observed with heating time beyond 30 minutes. The results demonstrated a severe quality loss of carrot puree subjected to the high temperature and long time process required in conventional thermal processing of vegetable purees.

Figure 28:
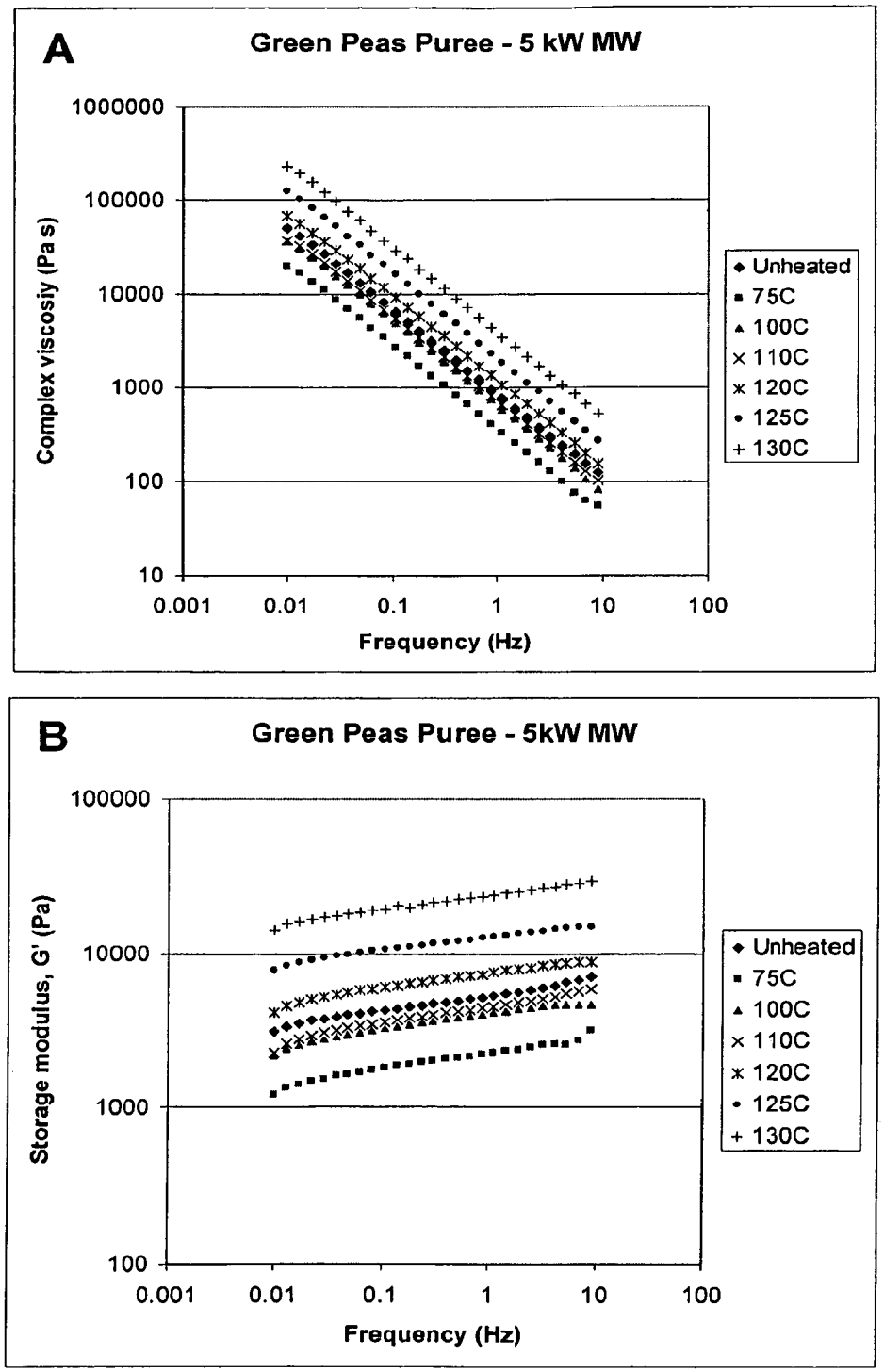
FIGS. 28A and 28B depict the rheological properties of green pea puree samples processed at various temperatures in the 5 kW microwave unit.

Green Pea Puree. The rheological properties of green pea puree samples processed at various temperatures in the 5 kW microwave unit are shown in FIG. 28. The dynamic viscosity ($\eta^*$) of all green pea puree samples also decreased with increasing frequency (FIG. 28A), showing pseudoplastic behavior. The green pea puree can be considered a weak gel since its mechanical spectra exhibited frequency dependency (FIG. 28B) with G' higher than G".

Figure 29:
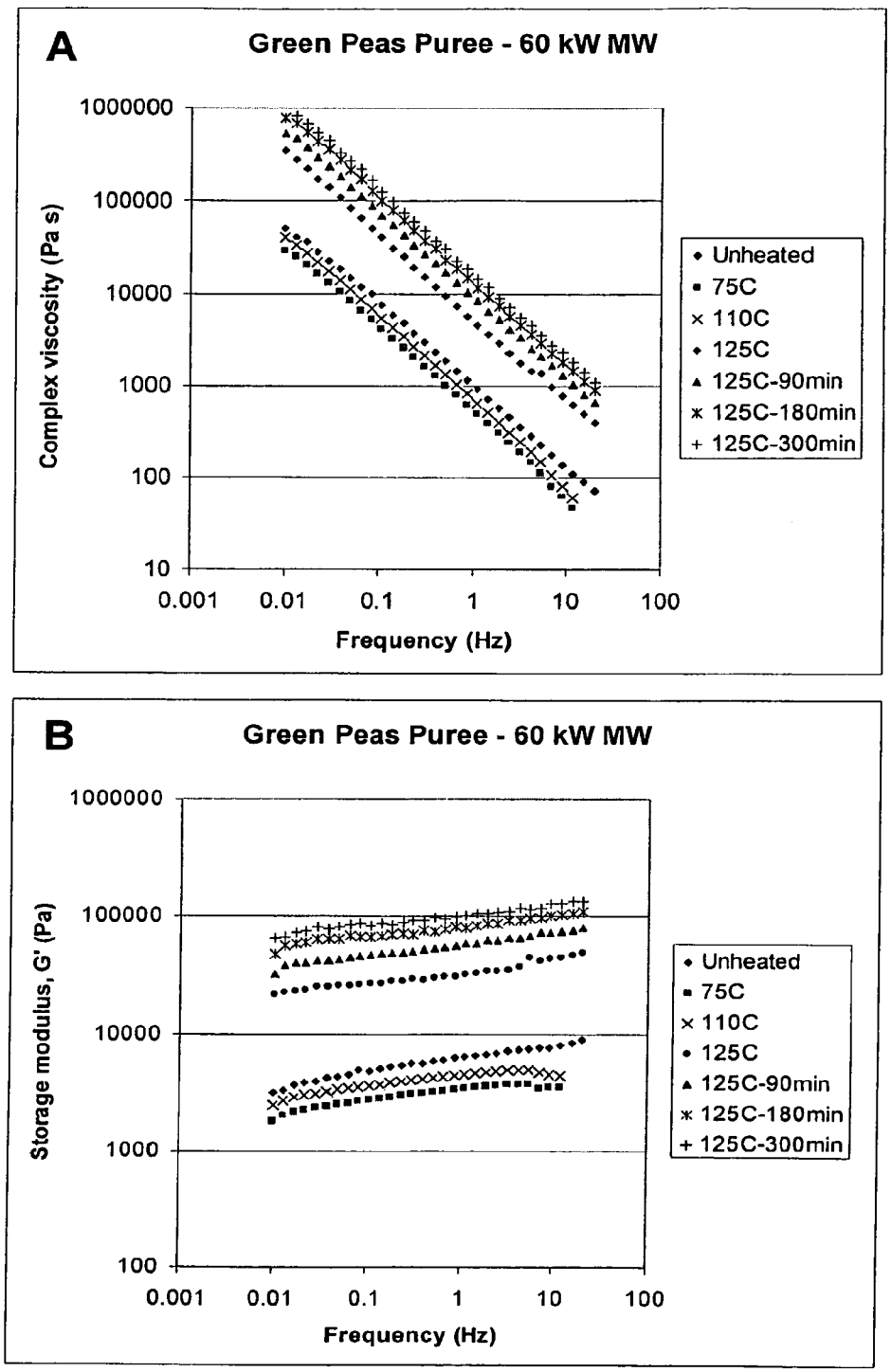
FIGS. 29A and 29B depict the rheological properties of green pea puree samples processed at various temperatures in the 60 kW microwave unit.

In contrast to carrot puree, $\eta^*$ and G' of the green pea puree initially decreased upon heating to 75-110° C., as compared to the unheated sample, and then significantly increased at higher temperatures (120-130° C.). This trend was also exhibited among the samples collected from the 60 kW unit experiments wherein the green peas puree was heated up to 125° C. and re-circulated for 6 hrs (FIG. 29). The phenomenon could be attributed to the high amylose content (35%) of pea starch and its C-type granular structure with high crystallinity and a tight molecular architecture (Bogracheva et al., 1998), which require high energy inputs for gelatinization and melting. A fast heating-high temperature process as the microwaving technique described herein would be beneficial in processing the pea purees into products with desired consistencies and gel properties.

Figure 30:
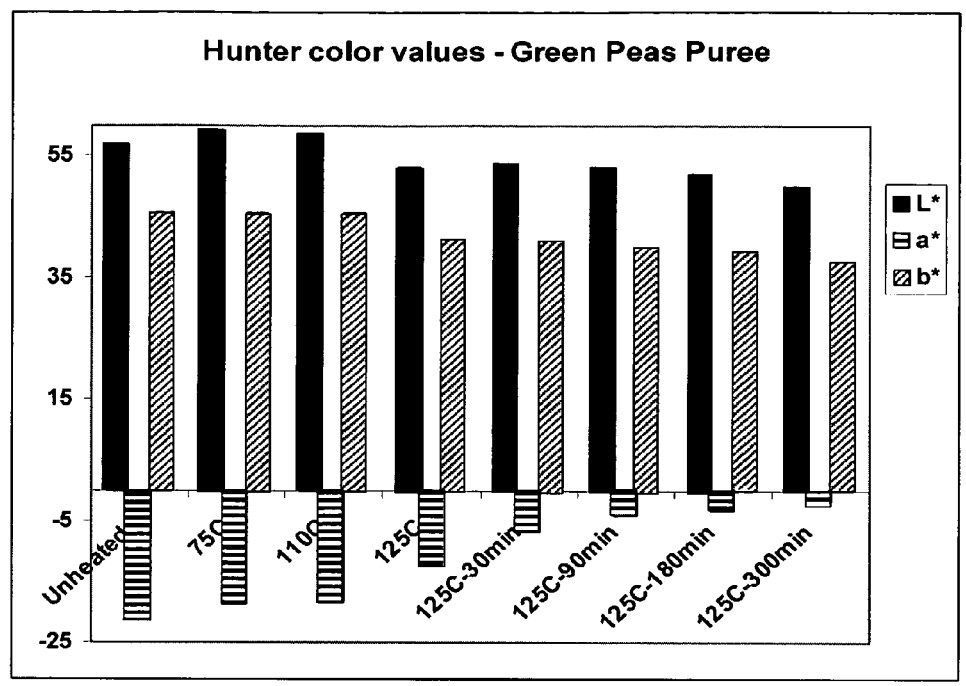
FIG. 30 depicts the color determination for green pea puree samples collected from the 60 kW tests. As depicted in FIG. 30, the L* value (lightness) and the b* value (yellowness) were slightly affected by microwaving temperature and time (<5% decreases). However, the loss in green color (a* values) was about 30% with reference to the unheated sample for the green pea puree heated to 125° C. With increasing heating time at 125° C. as in conventional thermal processing, the green color (a* values) of the puree was further degraded by 38% as compared to the unheated samples.

The color of the green peas samples collected from the 60 kW tests was also determined. As indicated in FIG. 30, the L* value (lightness) and the b* value (yellowness) were slightly affected by microwaving temperature and time (<5% decreases). However, the loss in green color (a* values) was about 30% with reference to the unheated sample for the green peas puree heated to 125° C. With increasing heating time at 125° C. as in conventional thermal processing, the green color (a* values) of the puree was further degraded by 38% as compared to the unheated samples.

Example 9

Shelf Stability of Microwaved SP Purees

Frozen sweetpotato puree from Beauregard cultivar was purchased from Bright Harvest Sweetpotato Company, Inc.

(Clarksville, Ark., United States of America). The thawed puree was sterilized using the 60 kW unit and aseptically packaged as described in Example 6. Packages of aseptic sweetpotato puree were stored at ambient temperature (22° C.), and two bags were randomly taken for microbiological analysis after 1 day, 2 weeks, 3 months, 6 months, and 18 months. Standard plate count assays were used to enumerate total aerobic bacteria, yeasts, and molds in the sweetpotato puree samples (Example 6). Microbiological test results for total aerobic bacteria, yeasts, and molds showed no growth of microorganisms for the puree samples stored for 1 day, 2 weeks, 3 months, 6 months, or 18 months at 22° C.

Figure 31:
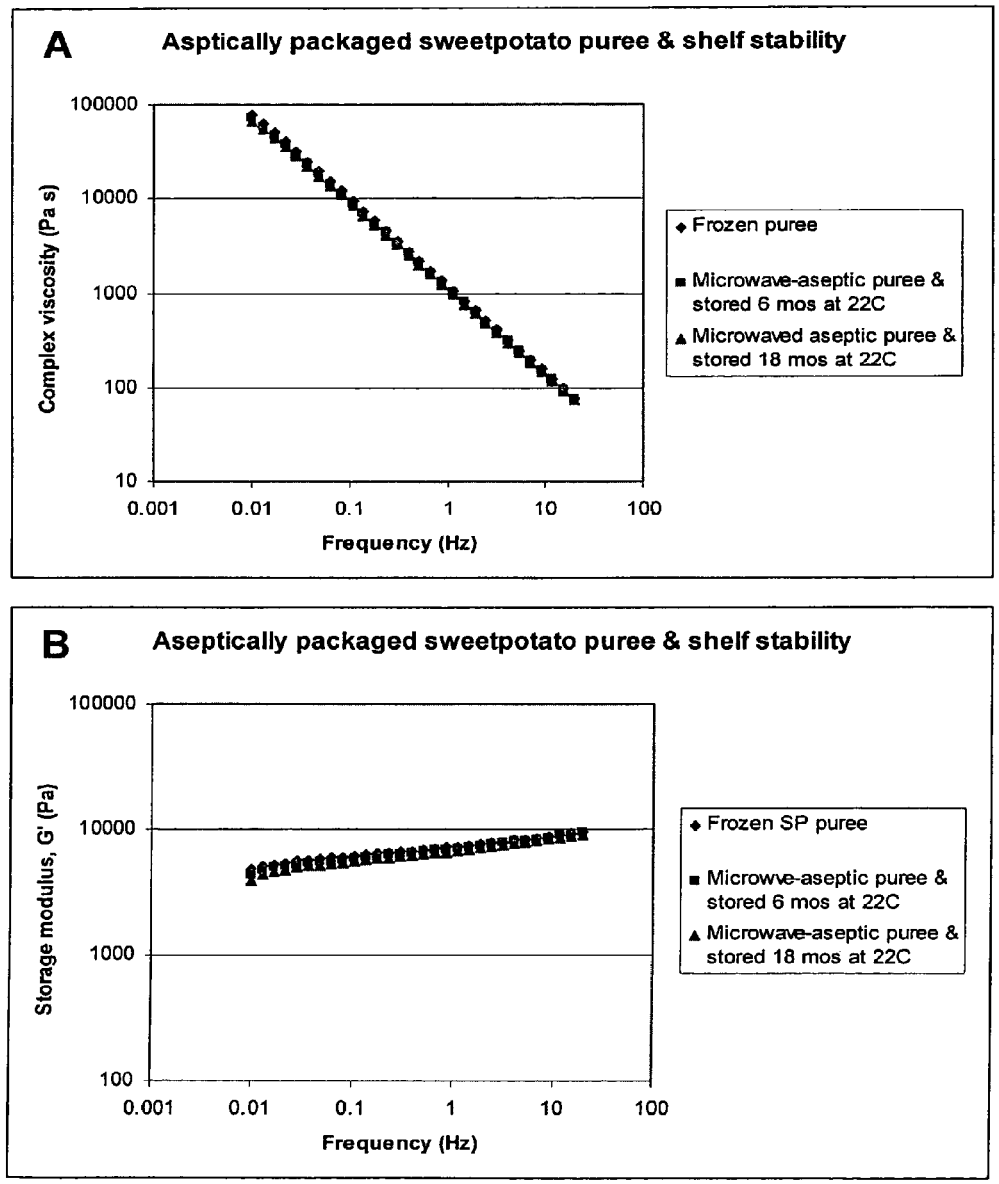
FIGS. 31A and 31B depict the results of rheological testing of sweetpotato puree microwaved to 130° C. and stored in aseptic packages at ambient conditions. Storage at ambient conditions had no effect on the rheological properties of the puree. The stored samples retained the dynamic viscosity and ($\eta^*$) and gel strength (G') comparable to those of the frozen stored puree.

Rheological tests & Hunter color measurements were performed as described in Example 8 for green pea and carrot purees. As indicated in FIG. 31, microwave processing of sweetpotato puree to 130° C. and storing the aseptic packages at ambient conditions had no effect on the rheological properties of the puree. The stored samples retained the dynamic viscosity and ($\eta^*$) and gel strength (G') comparable to those of the frozen stored puree.

Figure 32:
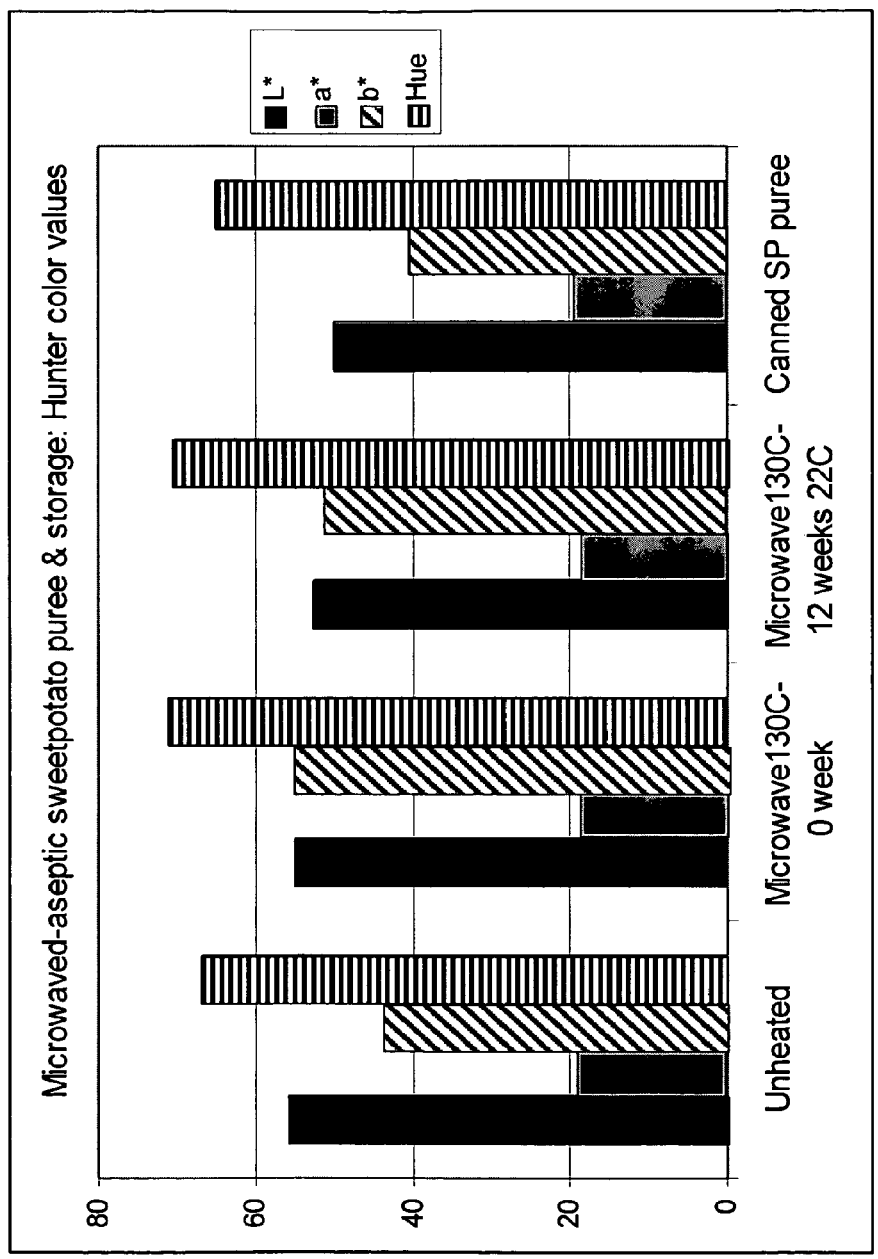
FIG. 32 depicts the color values of the microwaved sweetpotato puree as compared to frozen and canned purees (canned sweetpotato puree; can size no. 10) purchased directly from a local sweetpotato cannery. Microwave processing resulted in an increase of 25% in b* value (yellowness), slight decreases in a* (redness; <1%) and L* values (lightness; <2%), as compared to the frozen puree. Storage of the aseptic puree for 3 months at 22° C. further decreased the a* and L* values by 2.2% and 4.5%, respectively, while the b* value was about 15% higher than that of the frozen puree. The canned puree had dark brown color with L* values about 10.5% and 7.5% lower than those of the frozen puree.
Figure 33:
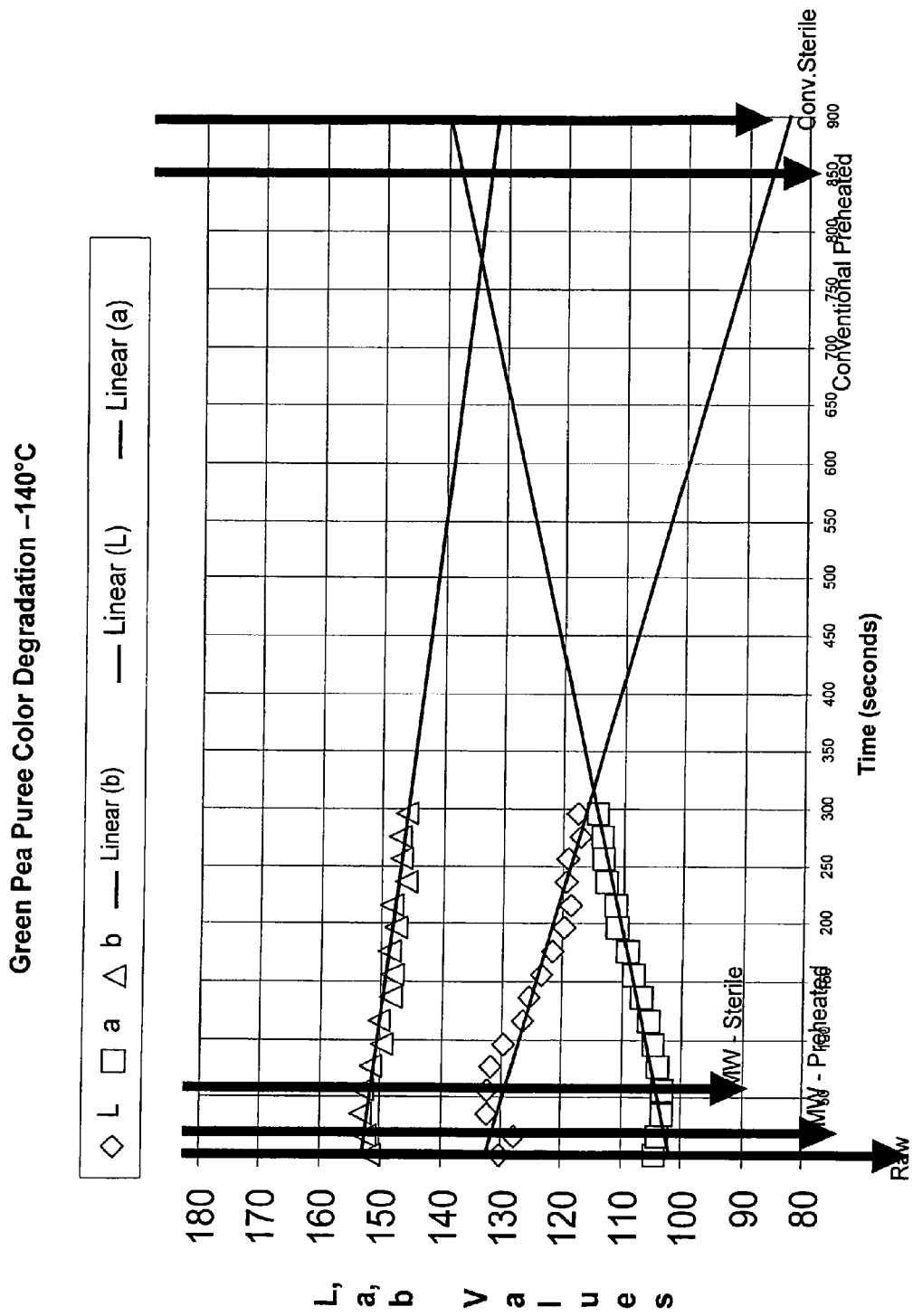
FIGS. 33-36 present color degradation data and projections for worst-case scenario under all conditions compared.
Figure 34:
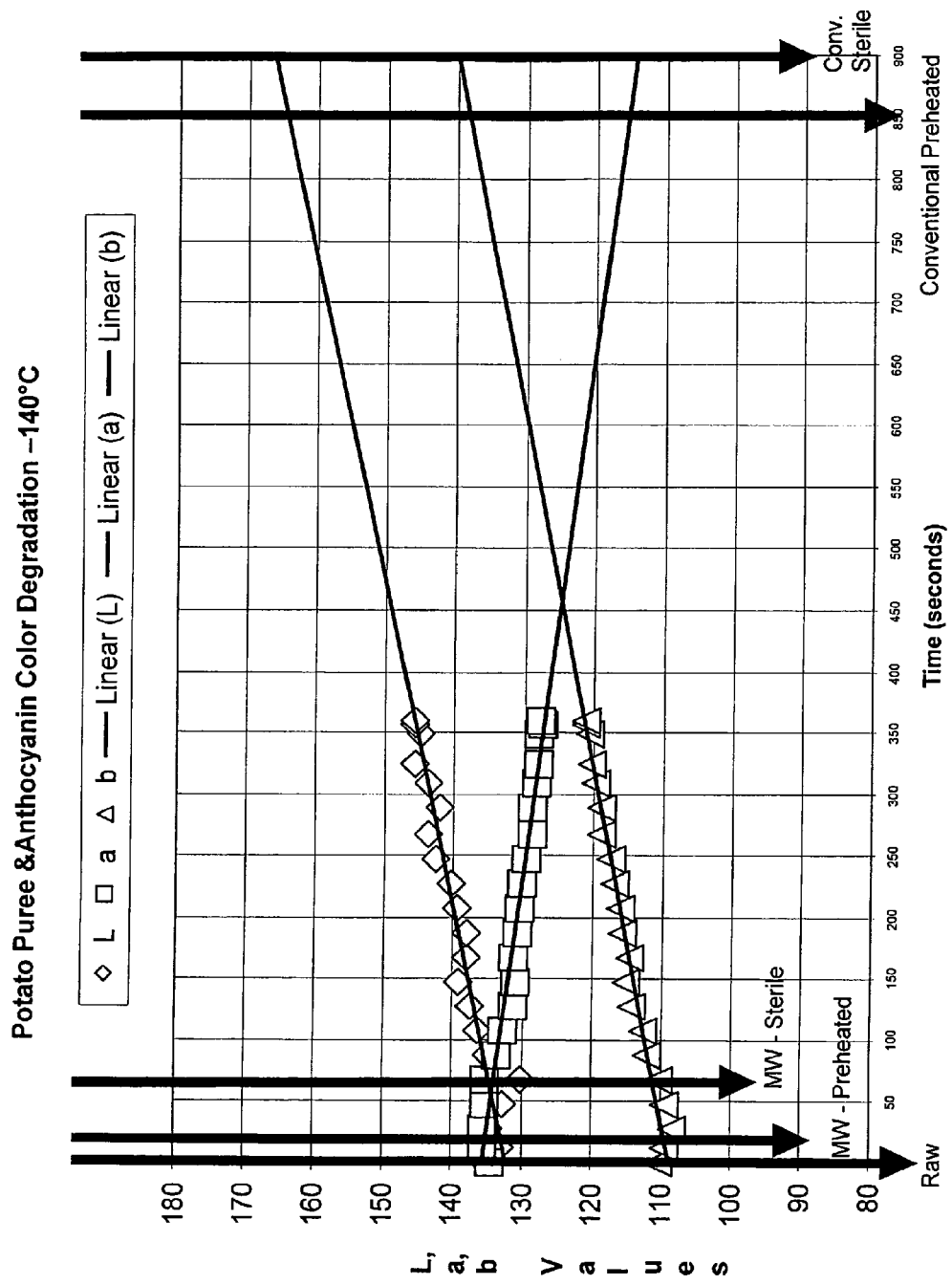
Figure 35:
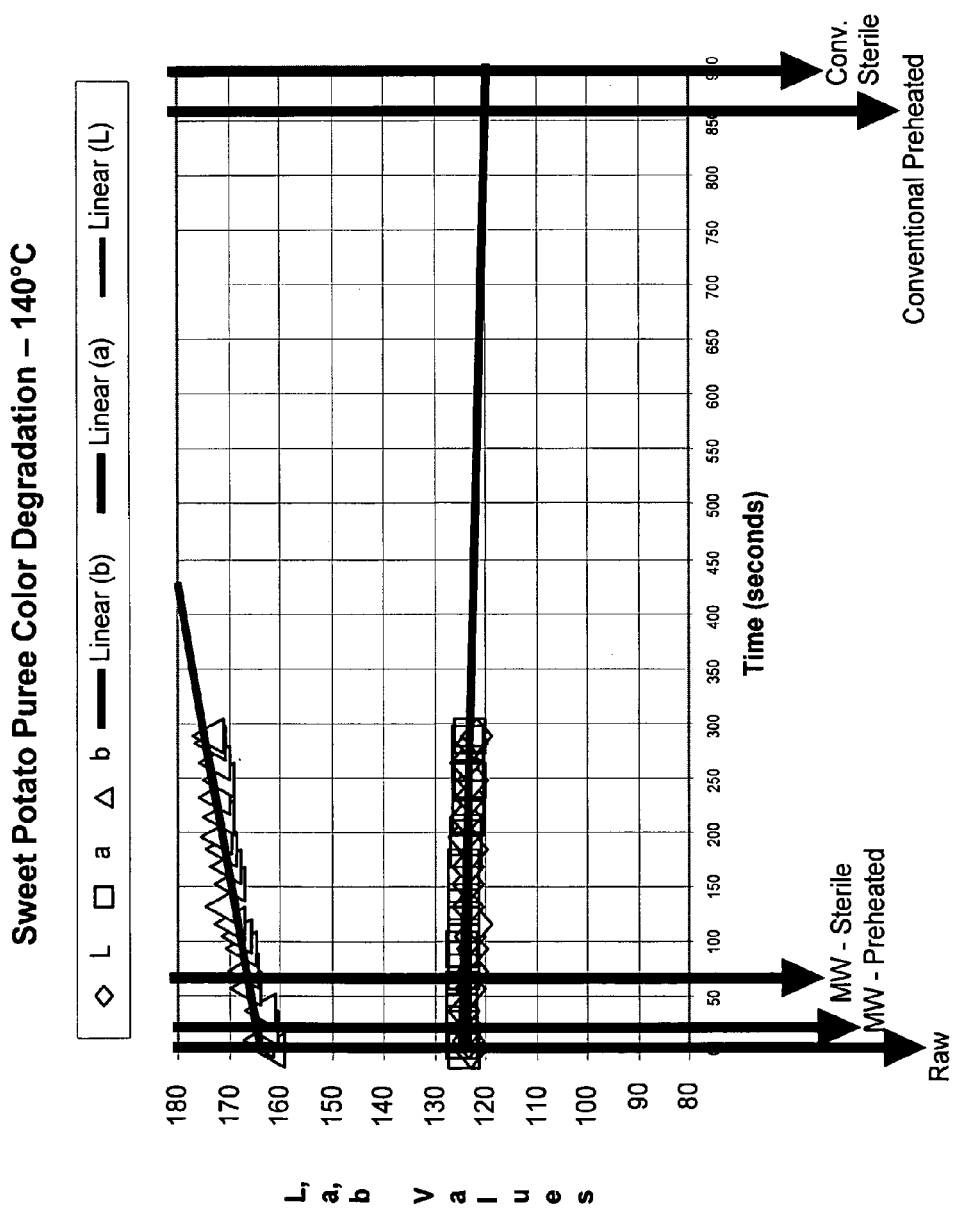
Figure 36:
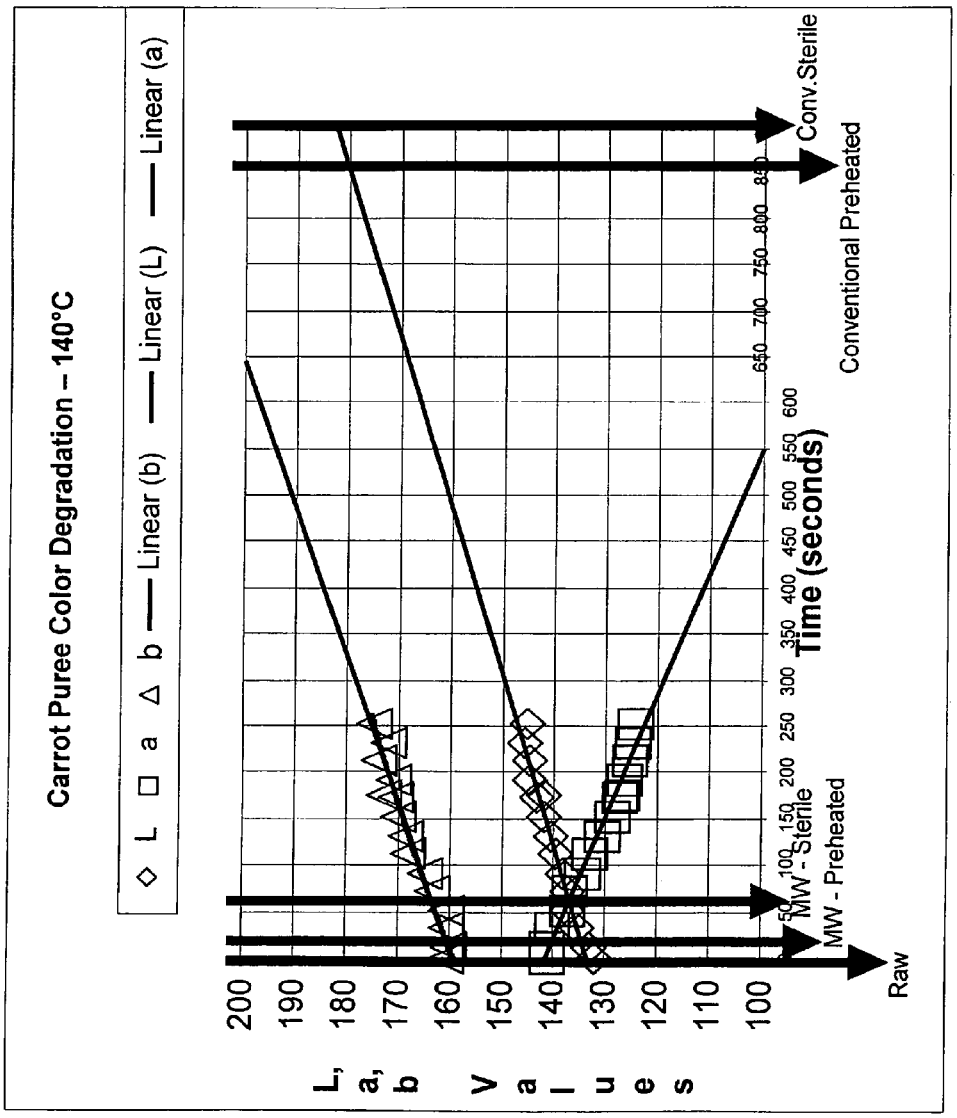

Color values of the microwaved sweetpotato puree as compared to frozen and canned purees (canned sweetpotato puree (can size no. 10) purchased directly from a local sweetpotato cannery: Bruce Foods Corporation, Wilson, N.C., United States of America) are shown in FIG. 32. Microwave processing resulted an increase of 25% in b* value (yellowness), slight decreases in a* (redness; <1%) and L* values (lightness; <2%), as compared to the frozen puree. Storage of the aseptic puree for 3 months at 22° C. further decreased the a* and L* values by 2.2% and 4.5%, respectively, while the b* value was about 15% higher than that of the frozen puree. The canned puree had dark brown color with L* values about 10.5% and 7.5% lower than those of the frozen puree.

Example 10

Color Degradation Data and Projections

In order to illustrate certain advantages of the rapid heating methods and apparatuses disclosed herein, a series of experimental measurements of the most sensitive of quality attributes of these products—color were performed.

Color is the first quality attribute evident to the industrial user, chef, cook and/or consumer available for evaluation upon opening of the package. It is also one of the most process-sensitive attributes for many of the targeted materials (vegetable and fruit purees, homogenates and pulps). This sensitivity is demonstrated by a rapid degradation of color attributes when the target food or biomaterial is exposed to heat at processing-level temperatures. The color, as evaluated by sensory means (human vision) and instrumental means (color measurements) undergoes rapid and often severe degradation upon processing and subsequently during storage, both in hermetically sealed and opened forms.

In order to measure the color degradation at temperature levels representative of temperatures of exposure during conventional aseptic and rapid microwave—assisted thermal sterilization—and to clearly document the advantage provided by the rapidity of thermal treatment achieved using the unique cylindrical microwave heater devices under the conditions disclosed herein and in combination with devices and procedures disclosed herein, a novel method of color measurement, recording and comparison have been devised.

Figure 38:
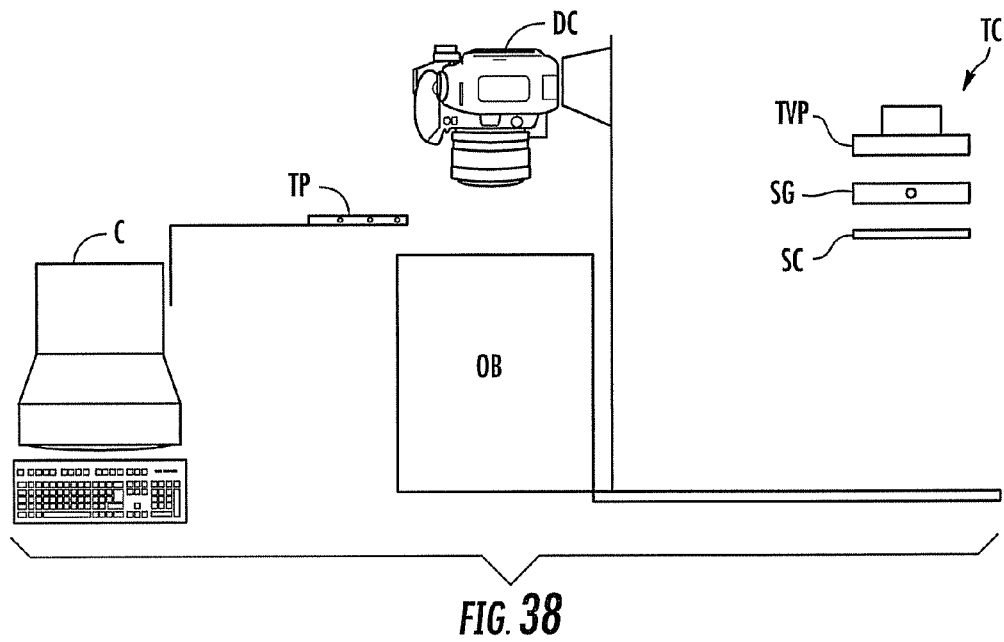
FIG. 38 is a schematic diagram of the high-temperature color degradation assembly employed in Example 10.

The schematic of the high-temperature color degradation assembly is presented in FIG. 38. The left-hand part of FIG. 38 shows the image and temperature control and acquisition installation and the right-hand side of FIG. 38 shows the components used to construct the image acquisition port enabling the acquisition of images and measurement of color values of tested materials in real time and under process-level temperatures.

A circulating oil bath with a digitally-controllable temperature level (Model RTE 111, Neslab Inc., Newington, N.H., USA) was used to preheat the test chamber containing the target material to selected process-level temperatures. The temperature level most representative of actual operating conditions (target temperatures) of both conventional continuous flow aseptic systems as well as the microwave-assisted aseptic sterilization system presented by this application is approximately 140° C. The oil bath system was therefore preheated to a level of 140° C. prior to submersing the test chamber containing the sample into the preheated oil bath.

Figure 39:
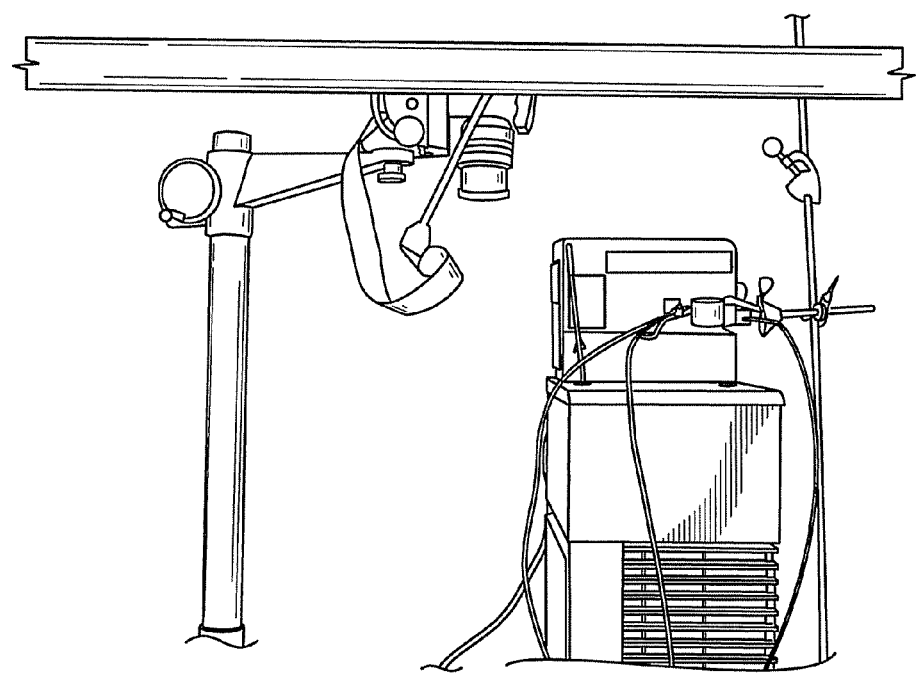
FIG. 39 is a drawing of the experimental setup described in Example 10.
Figure 40:
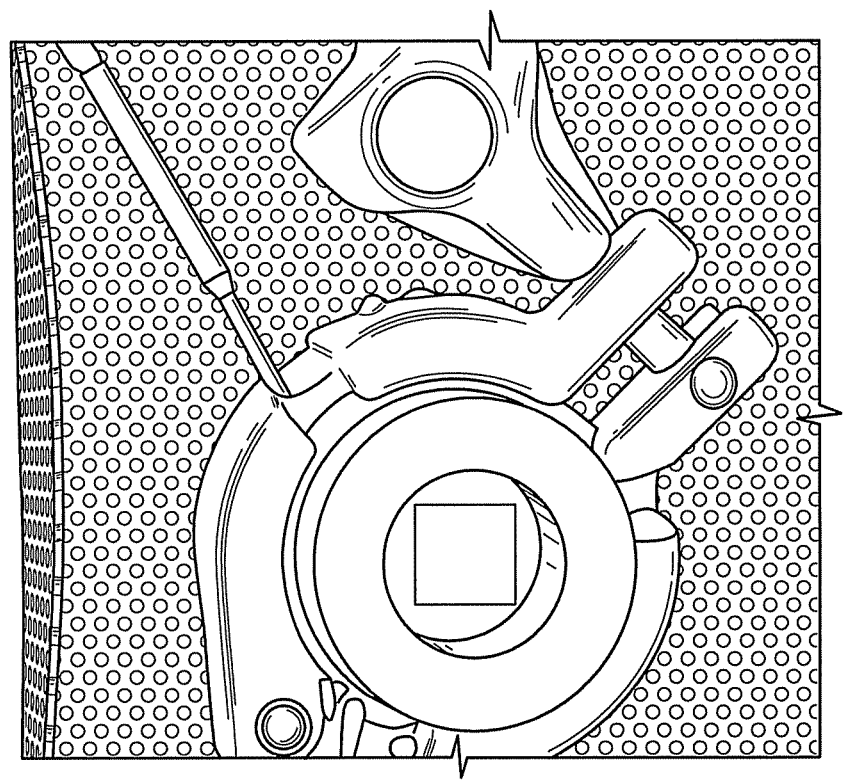
FIG. 40 is a drawing showing a sample chamber assembly, and special tri-clamp with a Smart gasket port containing the 3-point thermocouple probe in contact with the sample material described in Example 10.

The experimental setup described above is also presented by FIG. 39 and FIG. 40.

The test chamber to hold a minimally small quantity of sample (in order to ensure rapid pre-heating) was assembled from a 1.5 inch diameter Smart Gasket (Model G-TH-150-S-1, Rubber Fab, Andover, N.J., USA); which established the volume of the material contained within the test chamber. The gasket was fitted with a hypodermic three-point thermocouple probe (Model MT-23/20(3), Physitemp Instruments, Inc., Clifton, N.J., USA) containing three type T thermocouple leads within a 6 mm space at the tip of the probe, placed in direct contact with the test material itself. The bottom of the chamber was formed by using a 1.5 inch stainless steel sanitary cap with a Tri-clamp gasket groove (Model 16AMP-2-1.5-T316L,Waukesha Cherry-Burrell, Delavan, Wis., USA); whereas the top was fitted with a transparent view port made of fused high temperature glass and steel (Model Fuseview SS-15-FVTRI-FL, J.M. Canty Ltd, Dublin, Ireland) with the diameter of the visible window fitted to the diameter of the contained sample.

Temperatures acquired using the three-point thermocouple probe were measured using a 12-channel scanning thermometer (Model 692-000, Barnant Company, Barrington, Ill., USA), acquired every 4 seconds and recorded using a serial-port connection of a generic laptop computer. The typical image acquired by the system is presented in FIG. 40. The image shows the sample chamber assembly, special tri-clamp with a Smart gasket port containing the 3-point thermocouple probe in contact with the sample material. The 256*256 pixel sub-sample has been painted white to illustrate the imaged part of the sample surface that has been used in the color degradation analyses.

The visible window of the sample chamber was positioned facing up so that the timed images of the target material could be captured using a digital camera (Model D70, Nikon Instruments, Melville, N.Y., USA) every 4 seconds. The images were captured in a raw/digital format uncompressed (Nikon Electronic Format), converted into Adobe Photoshop readable TIF file format without file compression, imported into Adobe Photoshop software version 5.5. and cropped to contain a 256*256 pixel array of exposed target material. The average color values of L, a, and b of these reduced sub-images were measured using the Photoshop Histogram Function. The obtained values were then plotted against time of exposure of the chamber to the temperature of 140° C. using the Chart function of Microsoft Excel Program (Microsoft Office 2000 Software package) to plot the values of color components L, a and b versus time of exposure to process temperature.

Microsoft Excel Chart function Trendline was used to generate the linear regression lines and projected degradation of color components (L, a* and b*) over time of exposure to 140° C. Recorded worst case times of exposure for preheating for the presented process as well as the hold times for the rapid MW-based process were compared with the calculated estimates for the worst-case type of exposure for the conventional aseptic preheating (product pumped through approx. 200 feet of 1.5 inch internal diameter tube in tube heat exchanger at 1 gallon per minute flow rate). Identical hold time and temperatures were assumed for either process (MW-based and conventional preheating).

FIGS. 33-36 illustrate the results of real-time color degradation measurements performed using the equipment and methodology described above at 140° C. temperature of oil bath preheating.

On each of FIGS. 33-36 (Green Pea Puree, Carrot Puree, White Potato Puree colored with Anthocyanin and Sweet Potato Puree) there are five reference color quality/time of processing marked: Raw Material (prior to processing), MW Preheated Material (exiting from the MW heaters and in-line mixers), MW Sterilized Material (exiting from the hold tube segment); conventionally pre-heated (exiting from a typical tube in tube heat exchanger) and conventionally sterilized (exiting from a hold tube after the preheating using conventional heat exchangers).

For all four tested and illustrated materials, it is clearly evident that color degradation commences instantaneously and proceeds rapidly at a significant rate at sterilization level temperatures. The advantage of implemented rapid heating using the proposed MW or RF energy sources is also clearly evident from these plots.

It can be stated that color quality of the material subjected to a rapid MW or RF preheating is minimally degraded and appears to be nearly identical to the original raw material. The time required to hold the product at the final sterilization temperature ads a slight degradative effect to the color quality; however when compared to the worst case scenario for conventional aseptic preheating and holding, both of these degradative changes are minimal.

An advantage of rapid heating using the presently disclosed subject matter is evident regardless of the initial quality of the processed material—i.e. the damage imparted to the color quality of the material by conventional preheating will always be significantly greater than the degradation caused by rapid heating—assuming that the time-temperature exposures during the holding segment are identical, the difference between the two cumulative treatments is demonstrably and consistently in favor of the rapid MW/RF heating described herein.

In other words, the color quality of the product preserved by the proposed MW/RF based treatment at the time of packaging (time zero) will be superior to a conventionally treated product.

Quality degradation in general, as well as color quality degradation specifically, will continue to proceed during the storage of the packaged products. The rate and extent of these degradative processes will generally depend on conditions of storage and transportation prior to opening. Therefore, if both MW/RF sterilized and conventionally aseptically sterilized products are subjected to an identical set of post-packaging storage, transportation and distribution conditions; MW/RF sterilized product will have a consistent quality advantage, since the original color quality component will have been preserved to a much greater extent at the time of packaging.

Therefore, under identical up-stream conditions (quality, exposure and abuse history of the raw material) and identical down-stream conditions (storage, transportation and distribution); product obtained by the described MW/RF sterilization method will have superior quality relative to the product obtained by conventional thermal sterilization regardless and independent of these conditions.

REFERENCES

The references listed below as well as all references, including patents and non-patent literature, cited in the specification are incorporated herein by reference to the extent that they supplement, explain, provide a background for, or teach methodology, techniques, and/or compositions employed herein.

Adey (1989) *Biological effects of radio frequency electromagnetic radiation, In: Electromagnetic Interaction with Biological Systems* (Lin (ed.)) Plenum Press, New York, N.Y., United States of America, pages 109-140.

Bogracheva et al. (1998) 45 *Biopolymers* 323-332.

Campanella & Pelegi (1987) 52 *J Food Sci* 214-217.

Charm (1962) 28 *J Food Sci* 107-113.

CIE (1976). Colorimetry: official recommendations of the International Commission on Illumination. Paris: Commission Internationale de l'Éclairage [International Commission on Illumination], CIE No. 15 (E-1.3.1).

Coronel & Simunovic (2004) Solution of Helmholtz equation to determine the feasibility of continuous flow microwave processing of foodmaterials. Under review.

Coronel et al. (2003) 68 *Journal of Food Science*. 1976-1981.

Coronel et al. (2004) Dielectric properties of pumpable food materials at 915 MHz. Submitted to *Journal of Food Science*. Under review.

De Kee et al. (1980) 10 *J Texture Stud* 281-288.

DIFCO (1998) *Difco Manual,* 11th edition. Difco Laboratories, Division of Becton Dickinson and Company, Sparks, Md., United States of America.

Fasina et al. (2003) 6 *International Journal of Food Properties*. 461-472

Goldblith (1975) *In: Freeze Drying and Advanced Food Technology* (Goldblith, Rey and Rothmayr (eds.)), Academic Press, New York, N.Y., United States of America, pages 691-714.

Kyereme et al. (1999) 22 *Journal of Food Process Engineering* 235-247.

Lopez, A. (1987) A complete course in cannning and related processes. Book, III. Processing procedure for canned products. Baltimore, Mass. The Canning Trade. p. 96.

Missaire et al. (1990) 21 *J Texture Stud* 479-490.

Nakayama et al., (1980) 45 *J Food Sci* 844-847.

Ofoli et al. (1987) 18 *J Texture Stud* 213-230.

PCT International Patent Application Publications WO 0036879, WO 0143508, and WO 0184889.

Qui & Rao (1988)53 *J Food Sci* 1165-1170.

Sipahioglu & Barringer (2003) 68 *Journal of Food Science* 234-239.

Smith et al. (1982) 46 *Journal of Food Science* 1130-1142.

Steffe (1996) *Rheological Methods in Food Process Engineering, Second Edition*. Freeman Press, East Lansing, Mich., United States of America.

Swartzel (1982) 47 *Journal of Food Science* 1886-1891.

Swartzel (1986) 34 *Journal of Agricultural and Food Chemistry* 397.

Toledo et al. (1977) 42 *J Food Sci* 725-727.

Truong et al. (1995) 60 *Journal of Food Science* 1054-1059, 1074.

Truong (1992) In: Hill W A, Bonsi C K and Loretan P A (Eds.). *Sweetpotato Technology for the 21st Century*. Proceedings of the International Symposium, Jun. 2-6, 1991, Tuskegee, Ala., pages 389-399.

Turner & Danner (1957) Alabama Agricultural Experimental Station Circular No. 21.

U.S. Patent Application Publication Nos. 20010035407 and 20030205576

U.S. Pat. Nos. 4,091,119; 4,808,425; 4,975,246; 5,998,774; 6,087,642; 6,121,594; 6,265,702; 6,406,727; 6,583,395; and 6,797,929

Woolfe (1992) *Sweet potato: an untapped food resource*. Cambridge University Press, Cambridge, United Kingdom.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A process for thermally treating a flowable material while passing the flowable material as a continuous stream through a thermal treatment apparatus, the process comprising:
   (a) passing a flowable material continuously through a conduit, wherein at least a portion of the conduit is transparent to electromagnetic radiation;
   (b) heating the flowable material by exposing the at least a portion of the conduit that is transparent to electromagnetic radiation to a source of electromagnetic radiation; and
   (c) mixing the heated flowable material to provide for thermal equalization in at least a portion of the heated flowable material, wherein the mixing is performed by a mixing device within the conduit, the mixing device comprising a mixing bar capable of at least one of radial and rotational movement within the conduit.

2. The process of claim 1, wherein the flowing occurs at a constant flow rate.

3. The process of claim 1, wherein the flowing occurs at a constant heating power input or at a constant mass mean temperature at the heating exit for the flowable material.

4. The process of claim 1, wherein the flowable material is selected based on at least one of rheological, dielectric, and thermophysical properties, or combinations thereof, of the flowable material.

5. The process of claim 1, wherein the flowable material is a biomaterial.

6. The process of claim 5, wherein the biomaterial is a food biomaterial.

7. The process of claim 6, wherein the food biomaterial is selected based on at least one of rheological, dielectric, and thermophysical properties, or combinations thereof, of the food biomaterial.

8. The process of claim 1, wherein the heating results in an average bulk temperature increase rate in the flowable material of at least about 1 degree Fahrenheit per second or 0.5 degrees Celsius per second.

9. The process of claim 8, comprising one or more additional heating steps.

10. The process of claim 9, wherein the one or more additional heating steps precedes, accompanies, or follows the heating that results in an average bulk temperature increase rate in the flowable material of at least 1 degree Fahrenheit per second or 0.5 degrees Celsius per second.

11. The process of claim 1, wherein the heating is substantially free of heating by contacting the flowable material with a surface having a temperature that exceeds a maximum temperature level of the flowable material itself.

12. The process of claim 1, wherein the electromagnetic radiation has a wavelength of about $1 \times 10^{-4}$ meters or greater.

13. The process of claim 1, wherein the electromagnetic radiation has a frequency of about $3 \times 10^{12}$ waves per second or less.

14. The process of claim 1, wherein the mixing occurs before, during or after the heating, and combinations thereof.

15. The process of claim 1, wherein the flowable material is not subjected to a heated surface.

16. The process of claim 1, wherein the mixing bar serves to increase physical contact and heat exchange between regions of the flowable material having a higher temperature level and regions of the flowable material with a lower temperature level, which would not occur in the absence of the mixing bar.

17. The process of claim 16, wherein the mixing provides at least a 10% reduction in temperature distribution variability across the flowable material when compared to temperature distribution variability across the flowable material in the absence of the mixing.

18. The process of claim 16, comprising placing the mixing bar at a location selected from the group consisting of one or more points within, one or more exits, and combinations thereof, of the portion of the conduit that is exposed to the electromagnetic radiation.

19. The process of claim 1, further comprising packaging the flowable material for refrigerated storage.

20. The process of claim 1, wherein the heating and the mixing provide a sufficient temperature for a sufficient time to accomplish one of sterilization and pasteurization of the flowable material.

21. The process of claim 20, further comprising aseptically packaging the flowable material.

22. The process of claim 21, comprising holding the flowable material at a predetermined temperature for a predetermined length of time, and cooling, packaging and hermetically sealing the flowable material under aseptic conditions in a sterilized package.

23. The process of claim 20, where the flowable material is filled at a predetermined temperature level into a non-sterile package under one of atmospheric and increased pressure conditions in order to achieve concurrent sterilization of package surfaces in contact with the flowable material and then hermetically sealing the package.

24. A process for thermally treating a flowable material while passing the flowable material as a continuous stream through a thermal treatment apparatus, the process comprising:
   (a) passing a flowable material continuously through a conduit, wherein at least a portion of the conduit is transparent to electromagnetic radiation, wherein the flowable material is a semi-solid material;
   (b) heating the flowable material by exposing the at least a portion of the conduit that is transparent to electromagnetic radiation to a source of electromagnetic radiation; and
   (c) mixing the heated flowable material to provide for thermal equalization in at least a portion of the heated flowable material, wherein the mixing is performed by a mixing device within the conduit, the mixing device comprising a movable ferromagnetic mixer core and at least one microwave-transparent mixing element attached to the ferromagnetic mixer core.

25. The process of claim 24, wherein the ferromagnetic mixer core concurrently rotatably and orbitably moves within the conduit when exposed to a magnetic field.

26. The process of claim 24, wherein the mixing device further comprises a spacer element attached to a top of the ferromagnetic mixer core, and wherein the spacer element maintains a vertical position of the ferromagnetic mixer core.

* * * * *